US012673093B2

(12) United States Patent
Rowlinson et al.

(10) Patent No.: US 12,673,093 B2
(45) Date of Patent: Jul. 7, 2026

(54) METHOD AND COMPOSITION FOR TREATING ARGINASE 1 DEFICIENCY

(71) Applicant: Immedica Pharma AB, Stockholm (SE)

(72) Inventors: Scott W. Rowlinson, Austin, TX (US); Anthony G. Quinn, Gloucester, MA (US); Ann Lowe, Austin, TX (US); David Lowe, Austin, TX (US)

(73) Assignee: Immedica Pharma AB, Stockholm (SE)

( * ) Notice: Subject to any disclaimer, the term of this patent is extended or adjusted under 35 U.S.C. 154(b) by 208 days.

(21) Appl. No.: 18/344,083

(22) Filed: Jun. 29, 2023

(65) Prior Publication Data

US 2024/0009284 A1     Jan. 11, 2024

Related U.S. Application Data

(62) Division of application No. 16/210,248, filed on Dec. 5, 2018, now Pat. No. 11,717,562.

(60) Provisional application No. 62/745,000, filed on Oct. 12, 2018, provisional application No. 62/725,612, filed on Aug. 31, 2018, provisional application No. 62/594,747, filed on Dec. 5, 2017.

(51) Int. Cl.
| | |
|---|---|
| *A61K 38/50* | (2006.01) |
| *A61K 9/00* | (2006.01) |
| *A61K 38/51* | (2006.01) |
| *A61K 45/06* | (2006.01) |
| *A61K 47/60* | (2017.01) |
| *A61K 48/00* | (2006.01) |
| *A61P 3/00* | (2006.01) |

(52) U.S. Cl.
CPC ............ *A61K 38/50* (2013.01); *A61K 9/0019* (2013.01); *A61K 38/51* (2013.01); *A61K 45/06* (2013.01); *A61K 47/60* (2017.08); *A61K 48/005* (2013.01); *A61P 3/00* (2018.01); *C12Y 305/03001* (2013.01)

(58) Field of Classification Search
CPC ......... A61K 38/50; A61K 38/51; A61K 47/60
See application file for complete search history.

(56) References Cited

U.S. PATENT DOCUMENTS

| | | | |
|---|---|---|---|
| 6,316,199 | B1 | 11/2001 | Vockley et al. |
| 8,398,968 | B2 | 3/2013 | Mayall |
| 8,440,184 | B2 | 5/2013 | Georgiou et al. |
| 9,050,340 | B2 | 6/2015 | Georgiou et al. |
| 9,382,525 | B2 | 7/2016 | Leung et al. |
| RE46,423 | E | 6/2017 | Georgiou et al. |
| 10,098,933 | B2 | 10/2018 | Georgiou et al. |
| 11,717,562 | B2 | 8/2023 | Rowlinson et al. |
| 2002/0119554 | A1 | 8/2002 | Vockley et al. |

| | | | |
|---|---|---|---|
| 2010/0111925 | A1 | 5/2010 | Georgiou et al. |
| 2010/0247508 | A1 | 9/2010 | Leung et al. |
| 2012/0177628 | A1 | 7/2012 | Georgiou et al. |
| 2014/0023628 | A1 | 1/2014 | Leung et al. |
| 2014/0154797 | A1 | 6/2014 | Godfrin |
| 2014/0242060 | A1 | 8/2014 | Georgiou et al. |
| 2014/0363417 | A1 | 12/2014 | Cheng et al. |
| 2016/0095884 | A1 | 4/2016 | Godfrin et al. |
| 2017/0191078 | A1 | 7/2017 | Zhang et al. |
| 2017/0224843 | A1 | 8/2017 | Deglon et al. |
| 2017/0240922 | A1 | 8/2017 | Gill et al. |
| 2017/0283830 | A1 | 10/2017 | Saltzman et al. |
| 2019/0167770 | A1 | 6/2019 | Rowlinson et al. |
| 2021/0189371 | A1 | 6/2021 | Rowlinson |

FOREIGN PATENT DOCUMENTS

| | | |
|---|---|---|
| CN | 1673368 A | 9/2005 |
| CN | 103184208 A | 7/2013 |
| CN | 106456723 A | 2/2017 |
| EP | 1803465 A1 | 7/2007 |
| EP | 2799539 A1 | 11/2014 |
| JP | H02117383 A | 5/1990 |
| WO | WO-03063780 A2 | 8/2003 |
| WO | WO-2004001048 A1 | 12/2003 |
| WO | WO-2012061015 A2 | 5/2012 |
| WO | WO-2015164743 A2 | 10/2015 |
| WO | WO-2016033555 A1 | 3/2016 |
| WO | WO-2017192449 A1 | 11/2017 |
| WO | WO-2019113157 A1 | 6/2019 |
| WO | WO-2023201228 A1 | 10/2023 |

OTHER PUBLICATIONS

Aeglea Biotherapeutics, "Aeglea Biotherapeutics to Present Topline Data from Phase 1 Trial of Aeb11 02 for Treatment of Arginase I Deficiency at 2017 ACMG Annual Clinical Genetics Meeting," Press release, retrieved online at: ir.aegleabio.com/news-releases/news-release-details/aeglea-biotherapeutics-present-topline-data-phase-1-trial, Mar. 23, 2017, 3 pages.

Allen, L. et al., eds., "Ansel's Pharmaceutical Dosage Forms and Drug Delivery Systems," 8th ed. Lippincott, 2005, excerpt, pp. 51, 53, 54, 92-94, 162-164, 169, and 182-184. 16 printed pages.

Amayreh, W. et al., "Treatment of arginase deficiency revisited: guanidinoacetate as a therapeutic target and biomarker for therapeutic monitoring," Dev Med Child Neurol. Oct. 2014; 56(10): 1021-4. Epub May 10, 2014.

Ankudinov, A. L., et al., "Real-space Multiple-scattering Calculation and Interpretation of X-ray-absorption Near-edge Structure," Physical Review B, 58: 7565-7576, 1998.

Aoki S, et al., "Guanidine is a Zn(2+)-binding ligand at neutral pH in aqueous solution," J Am Chem Soc. May 15, 2002; 124(19): 5256-7.

(Continued)

*Primary Examiner* — Sikarl A Witherspoon

(74) *Attorney, Agent, or Firm* — KNOBBE, MARTENS, OLSON & BEAR, LLP

(57)     ABSTRACT

A method and composition to treat a subject with arginase 1 (ARG1) deficiency (ARG1-D) and to rapidly reduce the levels of at least one of arginine and/or a guanidino compound in the subject.

22 Claims, 14 Drawing Sheets

Specification includes a Sequence Listing.

(56)                References Cited

OTHER PUBLICATIONS

Ascierto, P. A., et al., "Pegylated arginine deiminase treatment of patients with metastatic melanoma: results from phase I and II studies," J Clin Oncol. Oct. 20, 2005; 23(30): 7660-8.
Ash, D. E., "Structure and function of Arginases," J Nutr. Oct. 2004; 134(10 Suppl): 2760S-2764S; discussion 2765S-2767S. 5 printed pages.
ATS Committee on Proficiency Standards for Clinical Pulmonary Function Laboratories, "ATS Statement Guidelines for the Six-Minute Walk," Am J Respir Crit Care Med. Jul. 1, 2002; 166(1): 111-7.
Auld, D. S. & Vallee, B. L., "Kinetics of Carboxypeptidase A. The PH Dependence of Tripeptide Hydrolysis Catalyzed by Zinc, Cobalt, and Manganese Enzymes," Biochemistry, 9: 4352-4359, 1970.
Aulton, M., ed., "Pharmaceutics: The Design and Manufacture of Medicines," Elsevier, 2007, excerpt, pp. 4, 5, 286, and 324. 5 printed pages.
Badarau A, et al., "The Variation of Catalytic Efficiency of Bacillus Cereus Metallo-beta-lactamase with Different Active Site Metal Ions," Biochemistry. Sep. 5, 2006; 45(35): 10654-66.
Bansal, V., et al., "Arginine Availability, Arginase, and the Immune Response," Curr Opin Clin Nutr Metab Care. Mar. 2003; 6(2): 223-8.
Beale R N & Croft D., "A Sensitive Method for the Colorimetric Determination of Urea," J. Clin. Pathol., 14: 418-24, 1961.
Bewley et al., "Crystal Structures of Bacillus Caldovelox Arginase in Complex with Substrate and Inhibitors Reveal New Insights into Activation, Inhibition and Catalysis in the Arginase Superfamily," Structure, 7: 435-448, 1999.
Bickmore et al., "Bond-valence Methods for Pka Prediction. Ii. Bond-valence, Electrostatic, Molecular Geometry, And Solvation Effects," Geochimica Et Cosmochimica Acta, 70: 4057-4071, 2006.
Burrage, L.C. et al., "Human recombinant arginase enzyme reduces plasma arginine in mouse models of arginase deficiency," Human Molecular Genetics, vol. 24, No. 22, 2015, pp. 6417-6427.
Cama et al., "Structural And Functional Importance of First-shell Metal Ligands in the Binuclear Manganese Cluster of Arginase 1," Biochemistry. Jul. 1, 2003; 42(25): 774858. 11 pages.
Carvajal et al., "Consequences of Mutations of Metal Ligands in Human Liver Arginase 1," Molecular Biology of the Cell, 13: 546A, 2002. 1 page.
Carvajal et al., "Interaction of Arginase with Metal Ions: Studies of the Enzyme from Human Liver and Comparison with Other Arginases," Camp Biochem Physiol B Biochem Mol Bioi, 112: 153-159, 1995.
Carvalho DR, et al., "Analysis of novel ARG1 mutations causing hyperargininemia and correlation with arginase I activity in erythrocytes", Gene. Nov. 1, 2012; 509(1): 124-30. doi: 10.1016/j.gene. 2012.08.003. Epub Aug. 16, 2012. 7 pages.
Carvalho, D.R., et al., "Clinical features and neurologic progression of hyperargininemia," Pediatr. Neural., 46(6): 369-74 (2012).
Cavalli et al., "Mutagenesis of Rat Liver Arginase Expressed in Escherichia coli: Role of Conserved Histidines," Biochemistry. Sep. 6, 1994; 33(35): 10652-7.
Cederbaum, S. D., et al., "Hyperargininemia with arginase deficiency", Pediatric Research (1979); 13(7): 827-833.
Cederbaum, SD, et al., "Treatment of hyperargininaemia due to arginase deficiency with a chemically defined diet", J Inherit Metab Dis. 1982; 5(2): 95-9. doi: 10.1007/BF01800000. 5 pages.
Chaberek et al., "Stability Of Metal Chelates. II. B-hydroxyethyliminodiacetic Acid," J Am. Chem. Soc., 74: 5057-60, 1952.
Cheng et al., "Enhanced hepatocyte growth factor signaling by type II transforming growth factor-beta receptor knockout fibroblasts promotes mammary tumorigenesis," Cancer Res., 67: 4869-4877, 2007.
Cheng et al., "Pegylated recombinant human arginase (rhArg-peg5,000mw) inhibits the in vitro and in vivo proliferation of human hepatocellular carcinoma through arginine depletion," Cancer Res. Jan. 1, 2007; 67(1): 309-17.

Cheng et al., "Remission of hepatocellular carcinoma with arginine depletion induced by systemic release of endogenous hepatic arginase due to transhepatic arterial embolisation, augmented by high-dose insulin: arginase as a potential drug candidate for hepatocellular carcinoma," Cancer Lett. Jun. 16, 2005; 224(1): 67-80. Epub Dec. 25, 2004.
Christianson and Cox, "Catalysis by metal-activated hydroxide in zinc and manganese metalloenzymes," Annu Rev Biochem. 1999: 68: 33-57.
Christianson and Fierke, "Carbonic anhydrase: evolution of the zinc binding site by nature and by design," Ace. Chem. Res., 29: 331-339, 1996.
Colleluori et al., "Expression, purification, and characterization of human type II arginase," Arch Biochem Biophys. May 1, 2001; 389(1): 135-43.
Cowley, DM, et al., "Adult-onset arginase deficiency", J Inherit Metab Dis. Aug. 1998; 21(6): 677-8. doi: 10.1023/a:1005492819527. 2 pages.
De Deyn, PP, et al. "Hyperargininemia: a treatable inborn error of metabolism", In De Deyn PP, Marescau B, Qureshi IA, Mori A, Guanidino Compounds in Biology and Medicine 2. London: John Libbey & Company Limited. 1997; 53-69. 19 pages.
Deignan et al., "Increased plasma and tissue guanidine compounds in a mouse model of hyperargininemia," Mol. Genet. Metab. 93: 172-178, 2008.
Deshmukh D. R., et al., "Guanidino compound metabolism in arginine-free diet induced hyperammonemia", Enzyme. 1991; 45: 128-136. 9 pages.
Di Costanzo et al., "Stereochemistry of guanidine-metal interactions: implications for L-arginine-metal interactions in protein structure and function," Proteins. Nov. 15, 2006; 65(3): 637-42.
Diez-Fernandez, C, et al., "Mutations and common variants in the human arginase 1 (ARG1) gene: Impact on patients, diagnostics, and protein structure considerations." Hum Mutat. Aug. 2018; 39(8): 1029-1050. doi: 10.1002/humu.23545. Epub Jun. 21, 2018. 22 pages.
Dillon et al., "Biochemical characterization of the arginine degrading enzymes arginase and arginine deiminase and their effect on nitric oxide production," Med Sci Monit. Jul. 2002; 8(7): BR248-53.
Dowling et al., "Evolution of the arginase fold and functional diversity," Cell Mol Life Sci. Jul. 2008; 65(13): 2039-55.
Downs, Stephen, "The Berg Balance Scale", J Physiother. Jan. 2015; 61(1): 46. Epub Dec. 1, 2014. 1 page.
Durante et al., "Arginase: a critical regulator of nitric oxide synthesis and vascular function," Clin Exp Pharmacol Physiol. Sep. 2007; 34(9): 906-11.
Enright et al., "Reference equations for the six-minute walk in healthy adults," Am. J. Respir. Grit. Care Med., 1998 158(5 Pt 1): 1384-1387.
Ensor et al., "Pegylated arginine deiminase (Adi-SS PEG20,000 mw) inhibits human melanomas and hepatocellular carcinomas in vitro and in vivo," Cancer Res. Oct. 1, 2002; 62(19): 5443-50.
Feun et al., "Clinical trial of CP 1-11 and VM-26/VP-16 for patients with recurrent malignant brain tumors," J Neurooncol. Apr. 2007; 82(2): 177-81. Epub Oct. 19, 2006.
Final Office Action for U.S. Appl. No. 16/210,248 dated Apr. 6, 2021, 8 pages.
Franzoi, Aea, et al. "The main neurological dysfunctions in hyperargininemia—literature review." Int J Neurol Neurother. 2018; 5(1). 7 pages.
Geiger et al., "Six-minute walk test in children and adolescents", J Pediatr. Apr. 2007; 150(4): 395-9, 399.e1-2. 6 pages.
Gill and Von Hippel, "Calculation of protein extinction coefficients from amino acid sequence data," Anal Biochem. Nov. 1, 1989; 182(2): 319-26.
Glazer, E., et al., "Bioengineered Human Arginase I with Enhanced Activity and Stability Controls Hepatocellular and Pancreatic Carcinoma Xenografts," Translational Oncology, 2011, 4(3): 138-146.
Haberle et al., "Suggested guidelines for the diagnosis and management of urea cycle disorders", Orphanet J Rare Dis. May 29, 2012: 7: 32. doi: 10.1186/1750-1172-7-32. 30 pages.

(56) References Cited

OTHER PUBLICATIONS

Haberle, J, et al., "Suggested guidelines for the diagnosis and management of urea cycle disorders: First revision." J Inherit Metab Dis. Nov. 2019; 42(6): 1192-1230. doi: 10.1002/jimd.12100. Epub May 15, 2019. 39 pages.

Han et al., "Synthesis and evaluation of alternative substrates for arginase," Bioorg Chem, 30: 81-94, 2002.

Haraguchi et al., "Molecular cloning and nucleotide sequence of cDNA for human liver arginase," Proc Natl Acad Sci USA. Jan. 1987; 84(2): 412-5.

Harris et al., "Pegylation: a novel process for modifying pharmacokinetics," Clin Pharmacokinet. 2001; 40(7): 539-51.

He et al., "Aminoguanidinium hydrolysis effected by a hydroxo-bridged dicobalt (II) complex as a functional model for arginase and catalyzed by mononuclear cobalt (II) complexes," J. Am. Chem. Soc., 120: 105-113, 1998.

Huemer M, et al., "Clinical phenotype, biochemical profile, and treatment in 19 patients with arginase 1 deficiency." J Inherit Metab Dis. May 2016; 39(3): 331-340. doi: 10.1007/s10545-016-9928-y. Epub Apr. 1, 2016. 10 pages.

International Preliminary Report on Patentability for International Application No. PCT/US2018/063982, mailed Jun. 18, 2020, 9 pages.

International Preliminary Report on Patentability for PCT/US2019/062471 dated May 25, 2021, 7 pages.

International Search Report and Written Opinion for International Application No. PCT/US2009/062969, mailed Jun. 17, 2010. 14 pages.

International Search Report and Written Opinion for International Application No. PCT/US2017/050816. mailed Dec. 28, 2017, 17 pages.

International Search Report and Written Opinion for International Application No. PCT/US2018/063982, mailed Feb. 28, 2019, 16 pages.

International Search Report and Written Opinion for International Application No. PCT/US2023/065630 dated Jul. 28, 2023, 9 pages.

Irving and Williams, "Order of stability of metal complexes," Nature, 162: 746-747, 1948.

Izzo et al., "Pegylated arginine deiminase treatment of patients with unresectable hepatocellular carcinoma: results from phase 1/11 studies," J. Clin. Oncol., 22: 1815-1822, 2004.

Jain-Ghai S, et al., "Arginase I deficiency: severe infantile presentation with hyperammonemia: more common than reported?" Mol Genet Metab. Sep.-Oct. 2011;104(1-2): 107-11. doi: 10.1016/j.ymgme.2011.06.025. Epub Jul. 13, 2011. 7 pages.

Jefferis, "Antibody therapeutics: isotype and glycoform selection," Expert Opin Biol Ther. Sep. 2007; 7(9): 1401-13.

Kalnine el al., Database GenBank Accession No. BT0199354, "Synthetic construct *Homo sapiens* arginase, type II mRNA, partial cds," NCBI Protein DB[online], Oct. 28, 2004 [retrieved on Aug. 16, 2013], URL: http://www.ncbi.nim.nih.~ov/nuccore/BT019935. 2 printed pages.

Katusic, Z., "Mechanisms of endothelial dysfunction induced by Aging: Role of Arginase 1", Circ Res. Sep. 28, 2007; 101(7): 640-1.

Khangulov et al., "L-arginine binding to liver arginase requires proton transfer to gateway residue His141 and coordination of the guanidinium group to the dimanganese(II,II) center," Biochemistry. Jun. 9, 1998; 37(23): 8539-50.

Knipp and Vasak, "A colorimetric 96-well microtiter plate assay for the determination of enzymatically formed citrulline," Anal Biochem. Nov. 15, 2000; 286(2): 257-64.

Kuhn et al., "pH-sensitive control of arginase by Mn(II) ions at submicromolar concentrations," Arch Biochem Biophys. Apr. 1991; 286(1): 217-21.

Lambert et al., "Hyperargininemia: intellectual and motor improvement related to changes in biochemical data," J Pediatr. Mar. 1991; 118(3): 420-4.

Lavulo et al., "Subunit-subunit interactions in trimeric arginase. Generation of active monomers by mutation of a single amino acid," J Biol Chem. Apr. 27, 2001; 276(17): 14242-8. Epub Jan. 24, 2001.

Lopez et al., "Insights into the interaction of human arginase II with substrate and manganese ions by site-directed mutagenesis and kinetic studies. Alteration of substrate specificity by replacement of Asn149 with Asp," Febs J. Sep. 2005; 272(17): 4540-8.

Luneburg, N. et al., "Reference intervals for plasmaL-arginine and the L-arginine:asymmetric dimethylarginine ratio in the Framingham Offspring Cohort," J Nutr. Dec. 2011; 141(12): 2186-90. Epub Oct. 26, 2011.

Marescau et al., "Guanidino compound analysis as a complementary diagnostic parameter for hyperargininemia: follow-up of guanidino compound levels during therapy," Pediatr Res. Mar. 1990; 27(3): 297-303.

Marescau et al., "The pathobiochemistry of uremia and hyperargininemia further demonstrates a metabolic relationship between urea and guanidinosuccinic acid," Metabolism. Sep. 1992; 41(9): 1021-4.

Mcgee et al., "Purification and characterization of Helicobacter pylori arginase, RocF: unique features among the arginase superfamily," Eur J Biochem. May 2004; 271(10): 1952-62.

Mora et al., "Implications of the S-shaped domain in the quaternary structure of human arginase," Biochemica. Biophysica. Acta., 1476: 181-90, 2000.

Newville, M., "IFEFFIT: interactive XAFS analysis and FEFF fitting," J Synchrotron Radiat. Mar. 1, 2001; 8(Pt 2): 322-4.

Ni et al., "Arginine deiminase, a potential anti-tumor drug," Cancer Lett. Mar. 8, 2008; 261(1): 1-11. Epub Jan. 7, 2008.

Notice of Allowance Issued in Canadian Patent Application No. 2,742,497, dated Aug. 12, 2019. 1 page.

Oeffinger et al., "Outcome tools used for ambulatory children with cerebral palsy: responsiveness and minimum clinically important differences," Dev Med Child Neurol. Dec. 2008; 50(12): 918-25.

Office Action and Search Report for Chinese Application No. CN201880079119.9 dated May 27, 2023, with English translation, 11 pages.

Office Action for Australia Application No. AU20180378485 dated Mar. 25, 2024, 4 pages.

Office Action for Japanese Application No. JP20200531164 mailed Jul. 25, 2023, with English translation, 4 pages.

Office Action issued in Canadian Patent Application No. 2,742,497, dated Apr. 20, 2018. 3 pages.

Office Action Issued in Canadian Patent Application No. 2,742,497, dated Oct. 30, 2018. 3 pages.

Office Action issued in European Patent Application No. 16163214. 6, dated Jun. 12, 2018. 5 pages.

Office Communication issued in European Patent Application No. 09824219.1, dated Aug. 27, 2013. 5 pages.

Office Communication issued in Japanese Patent Application No. 2011-534855, dated Aug. 22, 2013. (English translation of Japanese text). 11 pages.

Office Communication issued in Japanese Patent Application No. 2011-534855, dated Jun. 5, 2014. (English translation of Japanese text). 5 pages.

Office Communication issued in U.S. Appl. No. 13/863,448, dated Feb. 24, 2014. 6 pages.

Office Communication issued in U.S. Appl. No. 13/863,448, dated Jun. 19, 2014. 24 pages.

Office Communication issued in U.S. Appl. No. 12/610,685, dated Aug. 26, 2011. 9 pages.

Office Communication issued in U.S. Appl. No. 12/610,685, dated Dec. 8, 2011. 22 pages.

Office Communication issued in U.S. Appl. No. 12/610,685, dated May 24, 2012. 14 pages.

Palacios et al., "Studies on the advent of ureotelism. The effects of bivalent cations on the capacity of the hepatic arginase of the Mexican axolotl to hydrolyse endogenous arginine," Biochem J. Sep. 1969; 114(3): 449-54.

Periyannan et al., "Sequential binding of cobalt(II) to metallo-beta-lactamase CcrA," Biochemistry. Jan. 31, 2006; 45(4): 1313-20.

Perrin, "The hydrolysis of manganese (II) ion", Journal of the Chemical Society, pp. 2197-2200, 1962.

Prasad et al., "Argininemia: a treatable genetic cause of progressive spastic diplegia simulating cerebral palsy: case reports and literature review," J Child Neurol. Aug. 1997; 12(5): 301-9.

(56)                    References Cited

OTHER PUBLICATIONS

Ratilla et al., "Terminal and new bridging coordination of methylguanidine, arginine, and canavanine to platinum (II). The first crystallographic study of bonding between a transition metal and a Quanidine ligand", Inorganic Chemistry, 29: 918-926, 1990.

Reczkowski and Ash, "Rat liver arginase: kinetic mechanism, alternate substrates, and inhibitors," Arch. Biochem. Biophys., 312: 31-7, 1994.

Rehner et al., "Effect of manganese cobalt and nickel on the activity of liver arginase in-vitro and in-vivo," Medizin und Ernaehrung, 11 (2): 32-35, 1970. With English summary. 4 pages.

Robins and Shields, "Partial purification of bovine liver arginase," Archives of Biochemistry and Biophysics, 62: 55-62, 1956. (Abstract only). 1 page.

Roopenian and Akilesh, "FcRn: the neonatal Fc receptor comes of age," Nat Rev Immunol. Sep. 2007; 7(9): 715-25. Epub Aug. 17, 2007.

Sabio et al., "Glu-256 is a main structural determinant for oligomerisation of human arginase I," Febs Lett. Jul. 20, 2001; 501(2-3): 161-5.

Santhanam et al., "Inducible NO synthase dependent S-nitrosylation and activation of arginase1 contribute to age-related endothelial dysfunction," Circ Res. Sep. 28, 2007; 101(7): 692-702. Epub Aug. 17, 2007.

Sarkissian and Gamez, "Phenylalanine ammonia lyase, enzyme substitution therapy for phenylketonuria, where are we now?" Mol Genet Metab. Dec. 2005: 86 Suppl 1: S22-6. Epub Sep. 13, 2005. 5 pages.

Savoca et al., "Cancer therapy with chemically modified enzymes. II. The therapeutic effectiveness of arginase, and arginase modified by the covalent attachment of polyethylene glycol, on the taper liver tumor and the L5178Y murine leukemia," Cancer Biochem Biophys. Sep. 1984; 7(3): 261-8.

Schlune et al., "Hyperargininemia due to arginase I deficiency: the original patients and their natural history, and a review of the literature," Amino Acids. Sep. 2015; 47(9): 1751-62. Epub Jun. 27, 2015.

Schrover et al., "Minimal clinically important difference for the 6-min walk test: literature review and application to Morquio A syndrome," Orphanet J Rare Dis. Apr. 26, 2017; 12(1): 78. 11 pages.

Scolnick et al., "Altering the binuclear manganese cluster of Arginase diminishes thermostability and catalytic function," Biochemistry. Aug. 26, 1997; 36(34): 10558-65.

Scott et al., "Single amino acid (arginine) deprivation: rapid and selective death of cultured transformed and malignant cells," Br J Cancer. Sep. 2000; 83(6): 800-10.

Segawa et al., "A long-term survival case of arginase deficiency with severe multicystic white matter and compound mutations," Brain Dev. Jan. 2011; 33(1): 45-8. Epub Apr. 24, 2010.

Segel, "Enzyme Kinetics: behavior and analysis of rapid equilibrium and steady state enzyme systems," New York, John Wiley and Sons, Inc., pp. 914-917, 1975.

Shen et al., "Modulation of Arginine Metabolic Pathways As the Potential Anti-tumor Mechanism of Recombinant Arginine Deiminase," Cancer Lett., 231: 30-35, 2006.

Simmons et al., "Expression of full-length immunoglobulins in *Escherichia coli*: rapid and efficient production of aglycosylated antibodies," J Immunol Methods. May 1, 2002; 263(1-2): 133-47.

Sin, Y. Y., et al., "Arginase-1 deficiency", J Mol Med (Berl). Dec. 2015; 93(12): 1287-96. doi: 10.1007/s00109-015-1354-3. Epub Oct. 14, 2015. 10 pages.

Spector et al., "Properties of fetal and adult red blood cell arginase: a possible prenatal diagnostic test for arginase deficiency," Am J Hum Genet. Jan. 1980; 32(1): 79-87.

Stemmler et al., "EXAFS comparison of the dimanganese core structures of manganese catalase, arginase, and manganese-substituted ribonucleotide reductase and hemerythrin," Biochemistry. Aug. 12, 1997; 36(32): 9847-58.

Stockler-Ipsiroglu et al., "Guanidinoacetate methyltransferase (GAMT) deficiency: outcomes in 48 individuals and recommendations for diagnosis, treatment and monitoring," Mol Genet Metab. Jan. 2014; 111(1): 16-25. Epub Nov. 7, 2013.

Stone et al., "Engineering Human Arginase I As a Novel Cancer Therapeutic Agent," Retrieved from the Internet at http://aiche.conefx.com/aiche/09icbe/preliminaryprogram/abstract_143378.htm, retrieved on Feb. 29, 2012, dated Sep. 6, 2008. 1 page.

Summar, M. L., et al., "The incidence of urea cycle disorders." Mol Genet Metab. 2013; 110(1-2): 179-180. 2 pages.

Supplementary European Search Report and Search Opinion issued in European Application No. 09824219.1, mailed May 31, 2012. 7 pages.

Tao and Morrison, "Studies of aglycosylated chimeric mouse-human IgG. Role of carbohydrate in the structure and effector functions mediated by the human IgG constant region," J Immunol. Oct. 15, 1989; 143(8): 2595-601.

Uchino, T., et al., "Molecular basis of Phenotypic Variation in patients with argininemia," Hum Genet. Sep. 1995; 96(3): 255-60.

U.S. Department of Health and Human Services, Food and Drug Administration Center for Drug Evaluation and Research (CDER), "Guidance for Industry Estimating the Maximum Safe Starting Dose in Initial Clinical Trials for Therapeutics in Adult Healthy Volunteers," Jul. 2005, 30 pages.

Vockley et al., "Loss of functional mutations in conserved regions of the human arginase I gene," Biochemical and Molecular Medicine, 59: 44-51, 1996.

Waisbren, S. E., et al. "Biochemical markers and neuropsychological functioning in distal urea cycle disorders." J Inherit Metab Dis. 2018; 41(4): 657-667.

Webb, "Sixpack: a graphical user interface for XAS analysis using IFEFFIT," Physica Scripta, 115: 1011-1014, 2005.

Wheatley and Campbell, "Arginine catabolismliver extracts and cancer," Pathol. Oncol. Res., 8: 18-25, 2002.

Wheatley, "Arginine deprivation and metabolomics: important aspects of intermediary metabolism in relation to the differential sensitivity of normal and tumour cells," Semin Cancer Biol. Aug. 2005; 15(4): 247-53.

Wu, G. et al., "Arginine metabolism: nitric oxide and beyond," Biochem J. Nov. 15, 1998; 336 (Pt 1): 1-17.

Wyse et al., "In vitro stimulation of oxidative stress in cerebral cortex of rats by the guanidino compounds accumulating in hyperargininemia," Brain Res. Dec. 27, 2001; 923(1-2): 50-7.

Yau et al. "A phase 1 dose-escalating study of pegylated recombinant human arginase 1 (Peg-rhArg1) in patients with advanced hepatocellular carcinoma," Invest New Drugs. Feb. 2013; 31(1): 99-107. Epub Mar. 17, 2012.

Yoon et al., "Renal cell carcinoma does not express argininosuccinate synthetase and is highly sensitive to arginine deprivation via arginine deiminase," Int. J. Cancer, 120: 897-905, 2006.

Yu, JY, Pearl PL., "Metabolic causes of epileptic encephalopathy." Epilepsy Res Treat. 2013: 124934. doi: 10.1155/2013/124934. Epub May 22, 2013. 21 pages.

Zori, Roberto, et al., "Initial Results of a Phase 1 Open Label Study of AEB1102 Enzyme Replacement Therapy in Adult Patients with Arginase I Deficiency," Aeglea BioTherapeutics, Mar. 2017. 1 page.

Zori, R.T., "Once Weekly Intravenous Administration of Pegzilarginase Produces Marked and Sustained Reductions in Plasma Arginine Levels in Adults with Arginase 1 Deficiency: Early Results from a Phase 1/2 Open-label Study of Pegzilarginase," Molecular Genetics and Metabolism, 2018, Embase Database: Xp002788803, Database Accession No. Emb-622060654 [Abstract]. 1 page.

Aeglea, "Aeglea BioTherapeutics Provides AEB1102 Program and Corporate Update." Aeglea BioTherapeutics, Inc, press release May 23, 2017, 2 pages.

Anonymous, "Aeglea begins dosing in Phase I/II trial of AEB1102 for arginase 1 deficiency." Clinical Trials Arena, News Sep. 6, 2017, 2 pages.

patient treated with 0.015 mg/kg        patient treated with 0.03 mg/kg patient treated with 0.015 mg/kg        patient treated with 0.03 mg/kg Standard assessments include safety, arginine, guanidino compounds, neuromotor (6MWT, BBS, GMFM-66), PROMIS, adaptive behavior (ABAS), and pharmacokinetics. Single ascending doses in Part 1 ranged from 0.015 mg/kg to 0.20 mg/kg. Doses in Part 2 and the Open-Label Extension were based on plasma arginine control.

METHOD AND COMPOSITION FOR TREATING ARGINASE 1 DEFICIENCY

CROSS-REFERENCE TO RELATED APPLICATIONS

This application is a divisional of U.S. application Ser. No. 16/210,248 filed on Dec. 5, 2018, which claims the priority benefit of U.S. Provisional Application No. 62/594, 747 filed on Dec. 5, 2017, U.S. Provisional Application No. 62/725,612 filed on Aug. 31, 2018, and U.S. Provisional Application No. 62/745,000 filed on Oct. 12, 2018, the entire contents of which are incorporated herein by reference.

REFERENCE TO A SEQUENCE LISTING

The Sequence Listing associated with this application is provided electronically in XML file format and is hereby incorporated by reference into the specification. The name of the XML file containing the Sequence Listing is IMPH_005_04US_SubSeqList_ST26.xml. The XML file is 8,168 bytes, was created on Jan. 8, 2026, and is being submitted electronically via the USPTO Patent Center.

BACKGROUND

Disclosed are methods of treating arginase 1 deficiency in patients and compositions for treating arginase 1 deficiency (ARG1-D) in a patient.

Arginase 1 deficiency (also known as hyperargininemia or argininemia) is caused by deficiency or loss of activity of the arginase 1 protein due to, for example, a mutation in the arginase 1 (ARG1) gene. ARG1 is a urea cycle enzyme that converts arginine to ornithine. ARG1-D is a rare and progressive disease. It has been estimated to occur once in every 300,000 to 1,000,000 individuals. ARG1-D is an autosomal recessive urea cycle disorder that results in a toxic buildup of arginine and other guanidino compounds (GC). Clinical features of ARG1-D typically manifest in early childhood but can occur shortly after birth in some affected infants. Disease manifestations include spasticity, developmental delay, seizures, protein avoidance, episodic hyperammonemia, nausea and vomiting. In adolescence with disease progression, the patients may lose mobility, be unable to speak or comprehend, suffer from malnutrition and vitamin D deficiency. Further progression of the disease and its associated symptoms includes liver injury as evidenced by elevated transaminases and liver fibrosis, severe spasticity and muscle contractures, mental retardation and a limited lifespan. Unfortunately, dietary restrictions and nitrogen scavengers have been inadequate to prevent disease progression due to chronic marked elevations of arginine and other guanidino compounds and episodic hyperammonemia.

When providing a low protein diet to a patient with ARG1-D, the arginine levels can be reduced to about 265-300 μmon (Schlune et al., "Hyperargininemia due to arginase 1 deficiency: the original patients and their natural history, and a review of the literature," *Amino Acids* 47: 1751-1762, 2015). De novo arginine synthesis, which is influenced by dietary protein intake, accounts for approximately 5-15% of plasma arginine synthesis, and the primary source of arginine is body tissue turnover (Wu, G. et al., "Arginine metabolism: nitric oxide and beyond," *Biochem J,* 336 (Pt 1), 1-17, 1998). Therefore, the impact of dietary protein restriction on plasma arginine levels is limited and the circulating level of arginine in the subjects remains high due to the inability to degrade excess arginine.

Nonclinical studies of most therapies in ARG1-D animal models have not been shown to have a substantial impact on disease outcomes even with reductions in plasma arginine levels. Given that most of these approaches do not address the root cause of the disease, i.e., correct the cytosolic deficiency of ARG1 in the liver, the U.S. Food and Drug Administration (FDA) has questioned whether enhancement of plasma arginase levels may even have the same totality of effect as correcting intracellular ARG1 activity including reductions in arginine-derived guanidino compounds, which may contribute to the disease pathogenesis. Although there is literature evidence that dietary arginine restriction can reduce plasma arginine levels, the beneficial impact of dietary approaches on disease manifestations is limited due to chronic marked elevation of plasma arginine levels well above both the physiological normal range as well as medical guidelines. This is supported by the group that described progression in spasticity in 4 out of 11 patients despite dietary treatment and plasma arginine reduction (Prasad et al., "Argininemia: a treatable genetic cause of progressive spastic diplegia simulating cerebral palsy—case reports and literature review" *J. Child Neurol.* 12: 301-309, 1997). In line with this rationale, others have suggested that high levels of arginine metabolites such as argininic acid, guanidinoacetic acid, beta-guanidinopropionic acid, beta-guanidinobutyric acid, and N-α-acetylarginine may be important in the causation of the neurological sequelae in ARG1 deficient patients (Deignan et al., "Increased plasma and tissue guanidine compounds in a mouse model of hyperargininemia,"*Mol. Genet. Metab.* 93: 172-178, 2008; Segawa et al., "A long-term survival case of arginase deficiency with severe multicystic white matter and compound mutations," *Brain Dev.* 33: 45-48, 2011; Wyse et al., "In vitro stimulation of oxidative stress in cerebral cortex of rats by the guanidino compounds accumulating in hyperargininemia," *Brain Res.* 2001, 923(1-2): 50-7). Given the potential importance of guanidino compounds in ARG1-D, the ability of a low arginine diet to reduce these potentially neurotoxic metabolites has been investigated (Lambert et al., "Hyperargininemia: intellectual and motor improvement related to changes in biochemical data," *J. Pediatr.,* 1991, 118(3): 420-4). Although Lambert et al. were able to show that a low arginine diet was able to reduce blood arginine levels within approximately one month following strict diet control, the levels of guanidinoacetate and α-keto-δ-guanidino valeric acid (GVA) were not changed, indicating that diet does not appear to have the potential to rapidly control GC levels as a therapeutic intervention. Given the disorder and the complex underlying mechanism, new treatments to rapidly reduce and control the high levels of arginine in patients are required to address this unmet medical need.

SUMMARY

What is newly disclosed here are methods, compounds and compositions to treat ARG1-D patients that preferably obtain a rapid response in the patients, wherein the patients are human and can be adults, children, or infants.

A method is provided of treating Arginase 1 (ARG1) deficiency (ARG1-D) in a subject comprising administering an arginase to the subject in an amount sufficient to reduce a plasma level of arginine of the subject to below 200 μmol/L within about 2 to about 4 days after initial administration of the arginase. The plasma level of arginine of the subject may be reduced to within a range of 40 μmol/L to 115 μmol/L after initial administration of an arginase. The subject can be a human adult, human child or human infant (e.g., less than 12 months of age) having ARG1-D.

The arginase can be a wild type arginase 1 (e.g., SEQ ID NO: 2) or arginase II (e.g., SEQ ID NO: 1). The arginase can be a pegylated arginase 1, and it may have a cobalt metal cofactor in lieu of a manganese metal cofactor. The pegylated arginase 1 can be pegzilarginase.

The disclosed methods of treatment can further entail an administration where the plasma level of at least one of N-α-acetylarginine (NAArg), argininic acid (ArgA), GVA, guanidinoacetic acid (GAA), and arginine, is reduced to a normal level at least one time in the subject in less than 7 days, 3 days, 2 days, and/or 1 day, after initial administration. A method of treatment using an arginase can be such that the plasma level of GAA reaches a normal level after administration. A method can be such that the amount sufficient to reduce a plasma level of arginine of in the subject improves one or more characteristics such as resting spasticity, leg cramps related to spasticity, adaptive behavior, and the Patient-Reported Outcomes Measurement Information System (PROMIS) physical function score.

A method of treatment contemplates administering an intravenous dosage of from about 0.005 to about 1.00 mg/kg patient weight. Other ranges or use for intravenous administration can include 0.01 to 0.5 mg/kg, 0.01 to 0.2 mg/kg, 0.015 to 0.25 mg/kg, and 0.015 to 0.075 mg/kg, with every 0.005 increment in between the recited ranges also contemplated.

A method of treatment contemplates administering a subcutaneous dosage of from about 0.01 to about 1.50 mg/kg patient weight. Other ranges or use for intravenous administration can include 0.015 to 0.75 mg/kg, 0.015 to 0.30 mg/kg, 0.015 to 0.25 mg/kg, and 0.015 to 0.075 mg/kg, with every 0.005 increment in between the recited ranges also contemplated.

Another method contemplates administering an arginase to the subject at a dosage sufficient to reduce by at least 2 fold a plasma level of at least one compound selected from the group consisting of: ArgA, NAArg, GVA, GAA, and arginine, in the subject, wherein the plasma level is assayed about 24 to 48 hours after administration. Another method contemplates that the dosage administered reduces the plasma level of NAArg at least 3 fold. Another method contemplates that the dosage administered reduces the plasma level of GAA at least 2 fold. The arginase of the methods of treatment disclosed can be administered intravenously or subcutaneously to the patient or a combination of both. The arginase can be administered to the subject daily, weekly, bi-monthly, or monthly.

A nitrogen scavenger may also be administered to the subject. A disclosed composition having an arginase can comprise a nitrogen scavenger. The disclosed methods of treatment using an arginase can be administered to a subject along with a nitrogen scavenger and optionally the subject can further be on a low arginine diet. Another method of treating the subject with an arginase includes administering a nucleic acid operably linked to an adenoviral vector for delivery into the subject, and the arginase produces arginase in the subject upon administration to the subject. The amount of arginase produced by adenoviral vector delivery may be therapeutically effective to reduce by at least 2 fold a plasma level of at least one compound selected from the group consisting of: ArgA, NAArg, GVA, GAA, and arginine in the subject, wherein the plasma level is assayed about 24 to 48 hours after administration of the arginase.

Another method contemplates improvement of a neuromotor function after the initial administration of the arginase. The neuromotor function can be one or more of, without limitation, step, walking, spasticity, and/or alertness. Another method contemplates that the subject exhibits at least one of less resting spasticity, fewer leg cramps related to spasticity, adaptive behavior, and improved PROMIS T-score after initial administration of the arginase compared to at least one of spasticity, behavior, and PROMIS T-score before administration of the arginase. A method contemplates acute response to treatment with the arginase such that one or more toxic metabolites (e.g., GAA) are reduced to a normal level or cleared.

The method contemplates that a subject is administered at least one repeat dose of the amount of an arginase that reduces a plasma level of arginine to below 200 μmol/L. The plasma level of arginine may be reduced to a level below 200 μmol/L for at least 30 weeks and/or at least 40 weeks. After receiving eight of the at least one repeat doses, the subject may exhibit improvement in at least one of: (a) mobility or (b) adaptive behavior, relative to a baseline to said mobility or adaptive behavior for the subject before therapy. A plasma level of at least one of NAArg, ArgA, GVA, GAA, or arginine may be reduced as compared to the baseline plasma level in the subject. Another method contemplates that a subject has a minimal clinically important difference (MCID) of greater than 1 after 9 days of treatment. The plasma level of arginine is correlated with the MCID.

Also contemplated is a composition comprising pegzilarginase and a pharmaceutically acceptable buffer. The composition can comprise about 10% glycerol and the pharmaceutically acceptable buffer may be phosphate buffered saline in addition to the desired amount of pegzilarginase or other arginase. Use of a composition comprising an arginase (e.g., pegzilarginase) or a nucleic acid encoding an arginase in the manufacture of a medicament for the treatment of ARG1-D is provided.

Also contemplated is an arginase, such as a pegzilarginase is formulated in a red blood cell ghost.

A method for rapidly reducing a plasma level of at least one compound selected from the group consisting of: arginine, N-α-acetylarginine (NAArg), argininic acid (ArgA), α-keto-δ-guanidinovaleric acid (GVA), guanidinoacetic acid (GAA), to a normal level in a subject with Arginase 1 (ARG1) deficiency (ARG1-D) comprising administering to the subject a composition comprising a therapeutically effective amount of a pegylated arginase, wherein the pegylated arginase is administered intravenously initially at 0.005 mg/kg to 1.00 mg/kg, and weekly thereafter either subcutaneously or intravenously to the subject. Another method contemplates a pegylated arginase is administered intravenously initially at 0.005 mg/kg to 0.50 mg/kg. Another method contemplates a pegylated arginase is administered intravenously initially at 0.005 mg/kg to 0.20 mg/kg. Another method contemplates that a pegylated arginase is pegzilarginase. Another method contemplates that a plasma level of at least one compound selected from the group consisting of: ArgA, NAArg, GVA, GAA, and arginine, is reduced to a normal level in the subject in less than 3 days, 2 days, and/or 1 day after initial administration of a pegylated arginase. Another method contemplates that the dosage of a pegylated arginase administered to the subject is sufficient to reduce by at least 2 fold a plasma level of at least one compound from the group selected from: ArgA, NAArg, GVA, GAA, and arginine, wherein the plasma level is assayed about 24 to 48 hours after administration of the pegylated arginase.

A method for rapidly reducing a plasma level of at least one compound selected from the group consisting of: arginine, N-α-acetylarginine (NAArg), argininic acid (ArgA), α-keto-δ-guanidinovaleric acid (GVA), guanidinoacetic acid (GAA), to a normal level in a subject with Arginase 1 (ARG1) deficiency (ARG1-D) comprising administering to the subject a composition comprising a therapeutically effective amount of a pegylated arginase, wherein the pegylated arginase is administered subcutaneously initially at 0.01 mg/kg to 1.50 mg/kg, and weekly thereafter either subcutaneously or intravenously to the subject. Another method contemplates the pegylated arginase is administered subcutaneously initially at 0.015 mg/kg to 0.75 mg/kg. Another method contemplates a pegylated arginase is administered subcutaneously initially at 0.015 mg/kg to 0.30 mg/kg. Another method contemplates that a plasma level of at least one compound selected from the group consisting of: ArgA, NAArg, GVA, GAA, and arginine, is reduced to a normal level in the subject in less than 3 days, 2 days, and/or 1 day after initial administration of the pegylated arginase. Another method contemplates that the dosage of the pegylated arginase administered to the subject is sufficient to reduce by at least 2 fold a plasma level of at least one compound selected from the group consisting of: ArgA, NAArg, GVA, GAA, and arginine, wherein the plasma level is assayed about 24 to 48 hours after administration of the pegylated arginase.

Figure 1A:
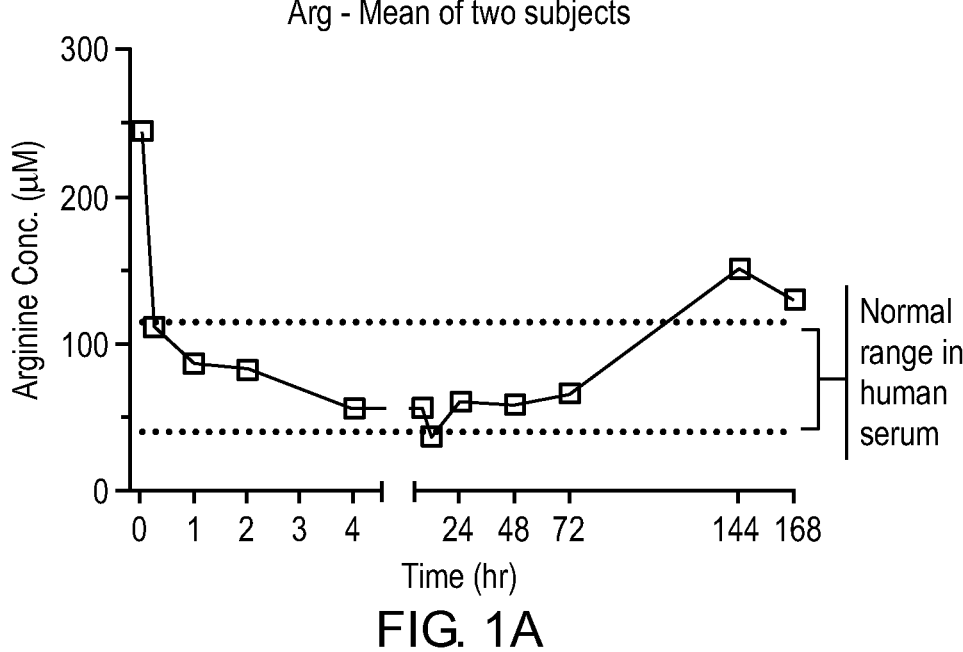
FIG. 1. Plasma concentration of FIG. 1A Arginine, FIG. 1B argininic acid (ArgA), FIG. 1C GVA, and FIG. 1D N-α-acetylarginine (NAArg). Arginine levels are the mean of the values obtained from the two ARG1-D patients treated with 0.03 mg/kg pegzilarginase, using a validated (good laboratory practice, i.e. GLP) assay. ArgA, GVA, and NAArg levels were assayed with a non-GLP assay using pooled samples from the same two ARG1-D patients treated with 0.03 mg/kg pegzilarginase. The normal range in humans are denoted by "*". A normal range of arginine in human serum is 40 µmol/L to 115 µmol/L. See, e.g., Lüneburg, N. et al., "Reference intervals for plasma L-arginine and the L-arginine:asymmetric dimethylarginine ratio in the Framingham Offspring Cohort." *J. Nutr.* 141(12): 2186-2190 (2011). A normal range of ArgA is <0.025 µmol/L to 0.100 µmol/L; a normal range of GVA is <0.050; and a normal range of NAArg is <0.025 µmol/L to 0.255 µmol/L. See, e.g., Marescau et al., "Guanidino compound analysis as a complementary diagnostic parameter for hyperargininemia: Follow-up of guanidino compound levels during therapy," *Pediatric. Res.* 27(3): 297-303 (1990).
Figure 1B:
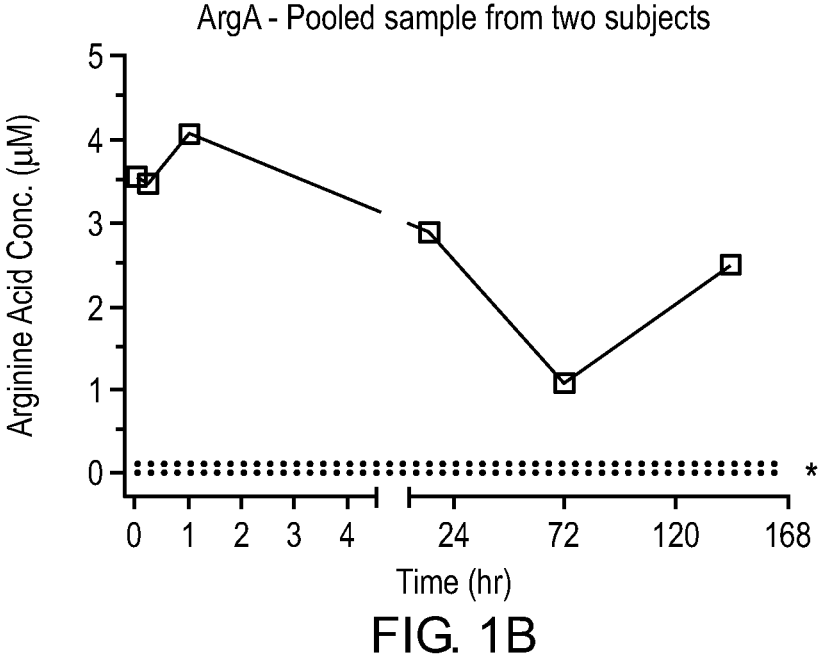
Figure 1C:
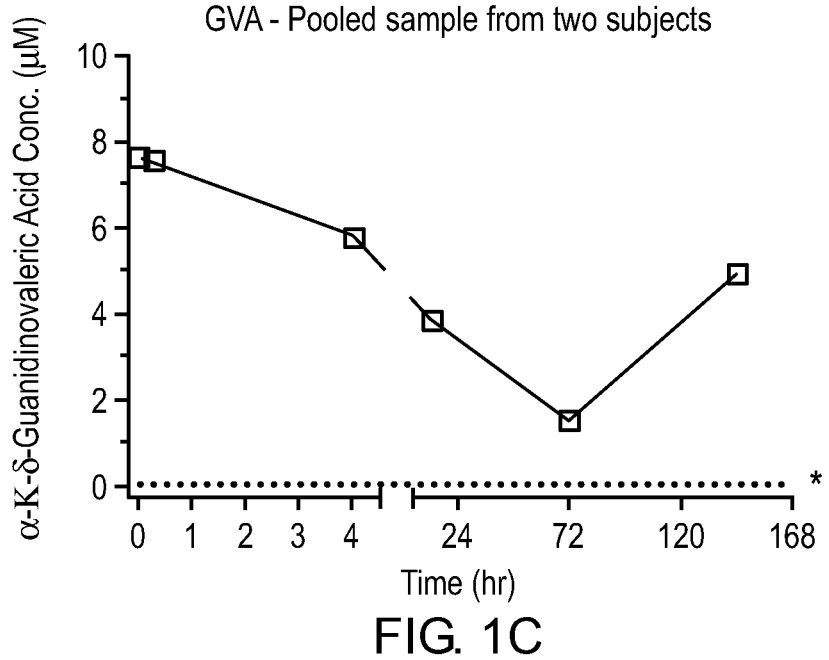
Figure 1D:
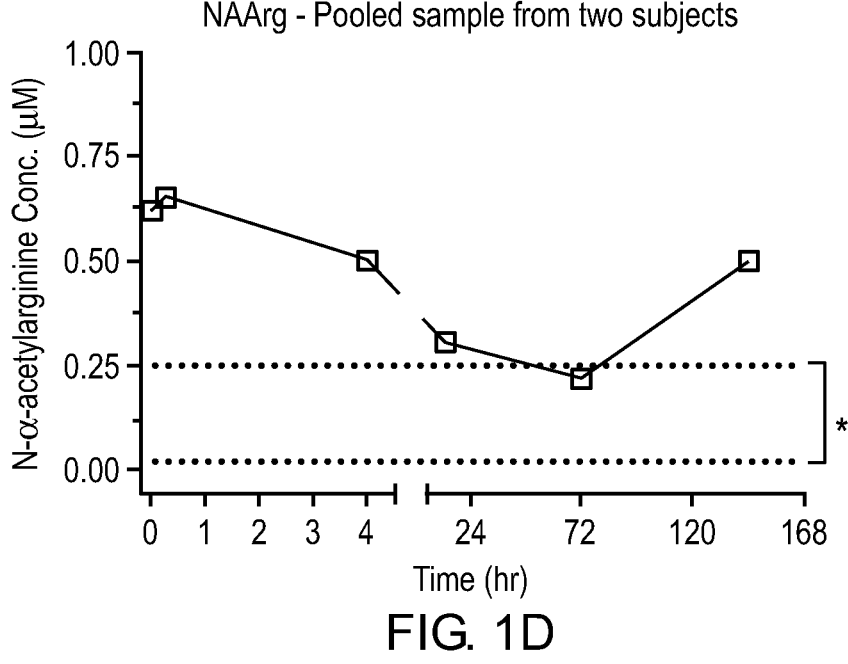

7 indicated by a line "a" and the average of the responder data points is indicated by a line "b."

DESCRIPTION

At time of seeking approval of the study disclosed in the Examples below, the U.S. Food and Drug Administration (FDA) believed that the scientific literature did not support a clear and consistent relationship between lowering plasma arginine levels via dietary arginine restriction and objective improvement in disease progression in ARG1-D patients. Initially, the FDA asserted that they could not see a prospect of direct clinical benefit from administering pegzilarginase in ARG1-D patients. The FDA raised concerns about the ability of pegzilarginase and drugs like it to address the underlying enzymatic defect in ARG1-D patients. The FDA queried whether peripheral circulation of an arginase containing pharmaceutical would have any realistic impact on the metabolism of intrahepatic arginine levels and the generation of related arginine metabolites. As a consequence, the FDA initially delayed testing in pediatric patients until treatment in adult patients could occur before permitting the testing to continue in the pediatric patients.

What has been surprisingly discovered is a method of treating ARG1 deficient patients to rapidly reduce the level of arginine and at least one of the guanidino compound (NAArg) level to within normal levels within 3 days (FIG. 1).

Definitions

As used herein, the terms "treating", "to treat", or "treatment", include restraining, slowing, stopping, reducing, ameliorating, or reversing the progression or severity of an existing symptom, disorder, condition, or disease relating to ARG1-D. A treatment may be applied prophylactically or therapeutically.

The term "effective amount" as used refers to that amount of a wild-type arginase or a pegylated arginase, such as pegzilarginase, being administered that will have the desired effect, such reducing a plasma level of one or more of the following: arginine, argininic acid (ArgA), GVA, N-α-acetylarginine (NAArg), GAA, and homoarginine (HArg). The effective amount may vary with factors such as the weight of the patient. For example, effective amounts can range between 0.005 to 1.00 mg/kg patient weight of patient for intravenous administration of a pegylated arginase (including every 0.005 value in between those ranges). Effective amounts for subcutaneous (s.c.) administration of a pegylated arginase to an ARG1-D patient include 0.01 to 1.50 mg/kg patient weight (including every 0.01 value in between those ranges). One example would be to administer a compound to achieve a range arginine, ArgA, GVA, GAA, and/or NAArg that is equivalent to a normal level of each compound in a normal human who does not suffer from ARG1 deficiency. Effective amounts can also improve muscle strength, ambulatory ability of a patient (i.e., ability to run, walk, ride a bike, climb stairs without support), and improve cognitive ability (for example Wechsler Intelligence Scale for Children (WISC) testing improvement) and/or adaptive behavior (for example Adaptive Behavior Assessment Scale (ABAS) or Vineland Adaptive Behavior Scale (VABS) testing improvement) (Lopata et al., "Comparison of Adaptive Behavior Measures for Children with HFASDs," *Autism Researc and Treatment, Vol.* 2013, pp. 1-10, (2013)). Normal levels of guanidino compounds are provided in the table below. A normal level of arginine is described by Lüneburg, N. et al., (2011).

A plasma level of arginine and/or a guanidino compound may be reduced to a normal range or a normal level, which may mean that at some point subsequent to administration of an initial dose and/or a repeat dose of an arginase, the plasma level of arginine and/or one or more guanidino compounds has a value within the range provided in the table below or 40 μmol/L to 115 μmol/L for arginine as described by Lüneburg, N. et al., (2011). For example, a patient's plasma levels for arginine and/or one or more of the guanidino compounds may oscillate in and out of the normal range during treatment with an arginase as disclosed herein. This patient is considered to have a plasma level of the assayed arginine and/or guanidino compounds that is reduced to the normal level or in the normal range. As another example, a patient may have an average amount of plasma levels of arginine and/or one or more guanidino compounds that is within the normal range (e.g., as provided in the table below or 40-115 μmol/L for arginine as described by Lüneburg, N. et al., (2011)), subsequent to receiving one or more dosages of the arginase as disclosed herein. Thus, the disclosed compositions and methods herein may reduce a subject's plasma level of arginine and/or a guanidino compound to a normal level or to the normal range at least one time after receiving an initial dosage and/or a repeat dosage of the arginase. In some patients, it was observed that plasma levels of arginine and/or a guanidino compound could be maintained, on average, at normal levels or within the normal range according to the disclosed methods herein.

TABLE 1

| Normal ranges of the guanidino compounds in human serum, urine, and cerebrospinal fluid (CSF) | | | |
|---|---|---|---|
| Guanidino compounds | Serum (μM) (n = 107) | Urine (μmol/g creatinine) (n = 30) | CSF (μM) (n = 45) |
| α-keto-δ-guanidinovaleric acid | <0.050 | <DL*-30 | <0.025 |
| Guanidinosuccinic acid | 0.100-0.500 | 15-160 | 0.020-0.150 |
| Creatine | 10-200 | 75-28000 | 35-90 |
| Guanidinoacetic acid | 0.400-3.00 | 100-2050 | 0.015-0.10 |
| N-α-acetylarginine | <0.025-0.255 | 10-100 | 0.030-0.20 |
| Argininic acid | <0.025-0.100 | 1-30 | <0.013 |
| Homoarginine | <0.500-2.80 | <DL-20 | 0.120-0.600 |

\* = Detection limit. Amounts discussed in Marescau et al., (1990).

The wild-type arginase can be based on human Arginase I or Arginase II. Wild type human Arginase II has the following sequence (Uniprot P78540):

(SEQ ID NO: 1)
MSLRGSLSRLLQTRVHSILKKSVHSVAVIGAPFSQGQKRKGVEHGPAAIR

EAGLMKRLSSLGCHLKDEGDLSFTPVPKDDLYNNLIVNPRSVGLANQELA

EVVSRAVSDGYSCVTLGGDHSLAIGTISGHARHCPDLCVVWVDAHADINT

PLTTSSGNLHGQPVSELLRELQDKVPQLPGFSWIKPCISSASIVYIGLRD

VDPPEHFILKNYDIQYESMRDIDRLGIQKVMERTFDLLIGKRQRPIHLSF

DIDAFDPTLAPATGTPVVGGLTYREGMYIAEEIHNTGLLSALDLVEVNPQ

LATSEEEAKTTANLAVDVIASSFGQTREGGHIVYDQLPTPSSPDESENQA

RVRI.

The wild type human Arginase I sequence has the following sequence (Uniprot/P05089):

```
                                        (SEQ ID NO: 2)
MSAKSRTIGIIGAPFSKGQPRGGVEEGPTVLRKAGLLEKLKEQECDVKDY

GDLPFADIPNDSPFQIVKNPRSVGKASEQLAGKVAEVKKNGRISLVLGGD

HSLAIGSISGHARVHPDLGVIWVDAHTDINTPLTTTSGNLHGQPVSFLLK

ELKGKIPDVPGFSWVTPCISAKDIVYIGLRDVDPGEHYILKTLGIKYFSM

TEVDRLGIGKVMEETLSYLLGRKKRPIHLSFDVDGLDPSFTPATGTPVVG

GLTYREGLYITEEIYKTGLLSGLDIMEVNPSLGKTPEEVTRTVNTAVAIT

LACFGLAREGNHKPIDYLNPPK.
```

A pegzilarginase disclosed here has the sequence of Arginase I, SEQ ID NO: 2, and has a cobalt metal cofactor in lieu of a manganese metal cofactor. Pegzilarginase is also pegylated as described in U.S. Pat. No. 8,440,184.

In some embodiments, the native arginase is modified only by the substitution of the metal cofactor. In other embodiments, the arginase is modified by substitution of the metal cofactor in addition to other modifications, such as substitutions, deletions, and truncations. In a particular embodiment, the invention provides a protein comprising a native amino acid sequence of human Arginase I or II and a non-native metal cofactor, wherein the amino acid sequence is lacking part of the native sequence. In particular embodiments, the non-native metal cofactor is cobalt. In some embodiments, the amino acid sequence of human Arginase I comprises SEQ ID NO:13. In other embodiments, the amino acid sequence of human Arginase II comprises SEQ ID NO:14. In yet other embodiments, the arginase lacks a portion of the wild-type sequence. In other embodiments, the amino acid sequence comprises a truncated Arginase I or Arginase II sequence. In a particular embodiment, the arginase is Arginase II and lacks the first 21 amino acids of the wild-type sequence. In another embodiment, the native arginases lack an N-terminal methionine.

By "administering" is meant the injection of a therapeutically effective amount of the compound and compositions containing said compound disclosed. For example without limitation, administration can be intravascular (i.v.) or subcutaneous (s.c.). The compositions of the invention can also be administered intramuscularly (i.m.).

The term "about" will be understood by persons of ordinary skill in the art and will vary to some extent depending on the context in which it is used. As used herein, "about" is meant to encompass variations of ±10%, ±5%, or ±1%.

The term "pegylated" refers to conjugation with polyethylene glycol (PEG), which has been widely used as a drug carrier, given its high degree of biocompatibility and ease of modification (see e.g., Harris et al., Clin. Pharmacokinet. 40(7): 539-51, 2001). PEG can be coupled (e.g., covalently linked) to active agents through the hydroxyl groups at the ends of the chain and via other chemical methods; however, PEG itself is limited to at most two active agents per molecule. In a different approach, copolymers of PEG and amino acids have been explored as novel biomaterials which would retain the biocompatibility properties of PEG, but which would have the added advantage of numerous attachment points per molecule (providing greater drug loading).

The PEGylated arginase variants can be formulated according to known methods to prepare pharmaceutically useful compositions. An ARG1-D patient can be administered a wild-type arginase protein (either arginase I or arginase II) that naturally contains manganese metal cofactor, or a wild-type arginase protein that has been pegylated and contains manganese metal cofactor. In another example, the ARG1-D patient can be administered an arginase that has cobalt metal cofactor in lieu of the native manganese metal cofactor. The cobalt metal cofactor containing arginase can further be pegylated, with an exemplary form being Co-ArgI-PEG (also referred to herein as AEB1102, pegzilarginase, or Co-hArgI) such as that described in U.S. Pat. No. 8,440,184, incorporated herein by reference. An exemplary form, such as pegzilarginase has approximately twelve 5 K (5000 Dalton) PEG units per monomer attached to one or more lysines present in the protein sequence of pegzilarginase. A desired formulation is a stable lyophilized product that is reconstituted with an appropriate diluent or an aqueous solution of high purity with optional pharmaceutically acceptable carriers, preservatives, excipients or stabilizers (see Remington, The Science and Practice of Pharmacy, 19th ed., Gennaro, ed., Mack Publishing Co., Easton, PA 1995). The drug can be formulated to be delivered in red blood cell ghosts (also referred to as engineered red blood cells). Another approach would be to administer arginine deiminase (ADI)-PEG 20 (Polaris Pharma) to an ARG1-D patient via i.m., s.c., or i.v or using described red blood cell ghosts.

As used herein the term "portion" when in reference to a protein (as in "a portion of a given protein") refers to arginase fragments, wherein the fragment has arginase activity in the urea cycle.

As used herein the terms "protein" and "polypeptide" refer to compounds comprising amino acids joined via peptide bonds and are used interchangeably.

As used herein, the term "fusion protein" refers to a chimeric protein containing the protein of interest (i.e., a human arginase or variant thereof) joined (or operably linked) to an exogenous protein fragment (the fusion partner that consists of a non-arginase protein). The fusion partner may enhance serum half-life, solubility, or both. It may also provide an affinity tag (e.g., His-tag) to allow purification of the recombinant fusion protein from the host cell or culture supernatant, or both.

The terms "in operable combination", "in operable order", and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "$K_m$," as used herein refers to the Michaelis-Menton constant for an enzyme and is defined as the concentration of the specific substrate at which a given enzyme yields one-half its maximum velocity in an enzyme-catalyzed reaction.

The term "$k_{cat}$," as used herein refers to the turnover number or the number of substrate molecule each enzyme site converts to product per unit time, and in which the enzyme is working at maximum efficiency.

The term "$K_{cat}/K_m$," as used herein is the specificity constant, which is a measure of how efficiently an enzyme converts a substrate into product.

The term "Mn-hArgI" refers to human Arginase I with a Mn (II) metal cofactor. The term "Co-hArgI" refers to human Arginase I (mutant or native) with a Co (II) metal cofactor.

The term "$IC_{50}$" is the half-maximal (50%) inhibitory concentration (IC) and thus a measure of effectiveness.

The term "gene" refers to a DNA sequence that comprises control and coding sequences necessary for the production of a polypeptide, such as arginase, or a precursor thereof. The polypeptide is encoded by a full-length coding sequence or by any portion of the coding sequence so long as the desired enzymatic activity of the arginase to reduce arginine to ornithine is retained.

The term "subject" refers to animals such as mammals, including humans.

The term "wild-type" refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "variant" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The following abbreviations are used herein:

Abbreviations

ADA Anti-drug antibody
ARG or Arg Arginine
ARG1-D Arginase 1 deficient
Arg1−/− mice Arginase deficient mice
ArgA argininic acid
AUC Area under the plasma concertation-time curve
BQL Below quantification limit
Co-ArgI-PEG Cobalt substituted and pegylated Arginase 1
EOI End of infusion
F/U Follow-up
GC Guanidino compounds
GLP Good laboratory practice
GVA α-keto-δ-guanidinovaleric acid
GAA guanidinoacetic acid
HArg homoarginine
i.v. intravascular or intravascularly (IV)
$K_2$EDTA plasma dipotassium ethylenediaminetetraacetic acid treated tubes to prevent coagulation
LC-MS/MS liquid chromatography-tandem mass spectrometry
NAArg N-acetyl-arginine
PEG Polyethylene glycol
s.c. subcutaneous, subcutaneously, or SC
SOI Start of infusion
wt wild type
Pegzilarginase, a recombinant human arginase enzyme produced in *E. coli*, was studied to see if it could reduce arginine levels to a normal range in a neonatal mouse an adult mouse ARG1 deficiency models. Pegzilarginase is pegylated for stability and half-life and has a cobalt metal cofactor in lieu of the manganese metal cofactor. The cobalt metal cofactor increases catalytic activity and improves stability of arginase. While the treatment with pegzilarginase did reduce plasma arginine and whole brain arginine, administration of the drug failed to treat hyperammonemia in the mice. It was theorized that the lack of arginine level decrease in liver tissue was perhaps because the administered enzyme pegzilarginase does not enter the liver. In the adult mouse models of ARG1-D, administration of pegzilarginase failed to improve animal survival. Pegzilarginase was tested in neonatal arginase I deficient mice (Arg1−/− mice), which is the closest simulation of the human disease in a mouse model (Burrage et al., "Human recombinant arginase enzyme reduces plasma arginine in mouse models of arginase deficiency," *Hum. Mol. Genetics* 24(22): 6417-27 (2015)). The multi-dose studies resulted in a reduction in plasma and brain arginine levels to the normal range; however, liver arginine levels were not beneficially impacted, and there was no improvement in survival compared to untreated Arg1−/− mice, which was unexpected.

Unlike the human clinical presentation of arginase I deficiency, Arg1−/− mice have severe hyperammonemia that appears responsible for their premature death (see e.g., Carvalho, D. R., et al., "Clinical features and neurologic progression of hyperargininemia," *Pediatr. Neurol.,* 46(6): 369-74 (2012)). Hyperammonemia is a complication that is less severe in human patients with this disorder. Given that elevated plasma arginine, rather than hyperammonemia may be the major treatment challenge in human patients with Arginase I deficiency, some postulate that Co-ArgI-PEG may have a therapeutic utility, but the degree of utility and the response cannot be reasonably predicted and even though hypothesized back in 1995, no testing or treatment models have been performed or developed. See, e.g., Uchino, T., et al., "Molecular basis of phenotypic variation in patients with argininemia," *Hum. Genet.* 96(3): 255-60 (1995).

I. Arginase

Wild-type arginase is a manganese-containing enzyme. It is the final enzyme of the urea cycle. Arginase is the fifth and final step in the urea cycle, a series of biophysical reactions in mammals during which the body disposes of harmful ammonia. Specifically, arginase converts L-arginine into L-ornithine and urea.

L-Arginine is the nitrogen donating substrate for nitric oxide synthase (NOS), producing L-citrulline and nitric oxide (NO). Although the K M of arginase (2-5 mM) has been reported to be much higher than that of NOS for L-Arginine (2-20 µM), arginase may also play a role in regulating NOS activity. Under certain conditions Arginase I is Cys-S-nitrosylated, resulting in higher affinity for L-Arginine and reduced availability of substrate for NOS.

Arginase is a homo-trimeric enzyme with an α/βfold of a parallel eight-stranded β-sheet surrounded by several helices. The enzyme contains a di-nuclear metal cluster that is integral to generating a hydroxide for nucleophilic attack on the guanidinium carbon of L-Arginine. The native metal cofactor for Arginase is $Mn^{2+}$. These $Mn^{2+}$ ions coordinate water, orientating and stabilizing the molecule and allowing water to act as a nucleophile and attack L-arginine, hydrolyzing it into ornithine and urea.

Mammals have two Arginase isozymes (EC 3.5.3.1) that catalyze the hydrolysis of L-Arginine to urea and L-ornithine. The Arginase I gene is located on chromosome 6 (6q23), is highly expressed in the cytosol of hepatocytes, and functions in nitrogen removal as the final step of the urea cycle. The Arginase II gene is found on chromosome 14 (14q24.1). Arginase II is mitochondrially located in tissues such as kidney, brain, and skeletal muscle where it is thought to provide a supply of L-Ornithine for proline and polyamine biosynthesis (Lopez et al., *FEBS J.* 272: 4540-48, 2005).

Arginases have been investigated for nearly 50 years as a method for degrading extracellular L-Arginine (Dillon et al., "Biochemical characterization of the arginine degrading enzymes arginase and arginine deiminase and their effect on nitric oxide production,"*Med. Sci. Monit,* 8(7): BR248-253 (2002)). While native arginase is cleared from circulation within minutes (Savoca et al., *Cancer Biochem. Biophys.* 7: 261-268, 1984), a single injection of PEG-Arginase MW 5,000 in rats was sufficient to achieve near complete arginine depletion for about 3 days (Cheng et al., *Cancer Res.* 67: 309-17, 2007).

A bacterial arginine hydrolyzing enzyme, ADI, which displays good kinetics and stability, has been tested in vitro. Unfortunately, ADI is a bacterial enzyme and therefore it induces strong immune responses and adverse effects in most patients and is not suitable for long-term administration in ARG1-D patients who would require regular administration.

For clinical use in patients with ARG1-D, it is essential that an arginase is engineered to allow it to persist for long times (e.g., days) in circulation. In the absence of any modification, human arginase has a half-life of only a few minutes in circulation primarily because its size is not sufficiently large to avoid filtration though the kidneys. Unmodified human arginase is very susceptible to deactivation in serum, and it is degraded with a half-life of only four hours.

II. Arginase Variant PEGylation

In certain aspects of the invention, methods and compositions related to pegylated arginase are disclosed. Specifically, PEGylation of arginase at an engineered Cysteine residue (e.g., substituting the third residue of the N-terminal) may be used to produce a homogenous pegylated arginase composition. Methods for isolation of pegylated arginase based on temporary disruption of polymerization are also disclosed.

PEGylation is the process of covalent attachment of PEG polymer chains to another molecule, normally a drug or therapeutic protein. "PEGylation" can be achieved by incubation of a reactive derivative of PEG with the target macromolecule. An increase the hydrodynamic size (size in solution) of the drug or therapeutic protein that prolongs its circulatory time by reducing renal clearance. PEGylation can also provide water solubility to hydrophobic drugs and proteins.

The first step in PEGylation can be the suitable functionalization of the PEG polymer at one or both terminal domains of the protein or internally to amino acids, such as lysines. PEGs that are activated at each terminus with the same reactive moiety are known as "homobifunctional", whereas if the functional groups present are different, then the PEG derivative is referred as "heterobifunctional" or "heterofunctional." The chemically active or activated derivatives of the PEG polymer are prepared to attach the PEG to the desired molecule.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, and tyrosine. The N-terminal amino group and the C-terminal carboxylic acid can also be used to attach the PEG to the polypeptide.

The techniques used to form PEG derivatives include reacting the PEG polymer with a group that is reactive with hydroxyl groups, typically anhydrides, acid chlorides, chloroformates, and carbonates. PEGylation chemistry can also use functional groups such as aldehyde, esters, amides etc. made available for conjugation. Heterobifunctional PEGs are very useful in linking two entities, where a hydrophilic, flexible and biocompatible spacer is needed. Preferred end groups for heterobifunctional PEGS are maleimide, vinyl sulfones, pyridyl disulfide, amine, carboxylic acids, and H-hydroxysuccinimide (NHS) esters.

The most common modification agents, or linkers, are based on methoxy PEG (mPEG) molecules. Their activity depends on adding a protein-modifying group to the alcohol end. Polyethylene glycol (PEG diol) can be used as the precursor molecule; the diol is subsequently modified at both ends in order to make a hetero- or homo-dimeric PEG-linked molecule (as shown in the example with PEG bis-vinylsulfone).

Proteins are generally PEGylated at nucleophilic sites such as unprotonated thiols (cysteinyl residues) or amino groups. Examples of cysteinyl-specific modification reagents include PEG maleimide, PEG iodoacetate, PEG thiols, and PEG vinylsulfone. All four are strongly cysteinyl-specific under mild conditions and neutral to slightly alkaline pH but each has some drawbacks. The amide formed with the maleimides can be somewhat unstable under alkaline conditions so there may be some limitation to formulation options with this linker. The amide linkage formed with iodo-PEGs is more stable, but free iodine can modify tyrosine residues under some conditions. PEG thiols form disulfide bonds with protein thiols, but this linkage can also be unstable under alkaline conditions. PEG-vinylsulfone reactivity is relatively slow compared to maleimide and iodo-PEG; however, the thioether linkage formed is quite stable. Its slower reaction rate also can make the PEG-vinylsulfone reaction easier to control.

Site-specific PEGylation at native cysteinyl residues is seldom carried out, since these residues are usually in the form of disulfide bonds or are required for biological activity. On the other hand, site-directed mutagenesis can be used to incorporate cysteinyl PEGylation sites for thiol-specific linkers. The cysteine mutation must be designed such that it is accessible to the PEGylation reagent and is still biologically active after PEGylation.

Amine-specific modification agents include PEG NHS ester, PEG tresylate, PEG aldehyde, PEG isothiocyanate, and several others. These amine-specific agents generally react under mild conditions and are very specific for amino groups.

Due to the multiple lysine residues on most proteins, site-specific PEGylation can be a challenge. Fortunately, because these reagents react with unprotonated amino groups, it is possible to direct the PEGylation to lower-pK amino groups by performing the reaction at a lower pH. Generally, the pK of the alpha-amino group is 1-2 pH units lower than the epsilon-amino group of lysine residues. By PEGylating the molecule at pH 7 or below, high selectivity for the N-terminus frequently can be attained. However, this is only feasible if the N-terminal portion of the protein is not required for biological activity. Still, the pharmacokinetic benefits from PEGylation frequently outweigh a significant loss of in vitro bioactivity, resulting in a product with much greater in vivo bioactivity regardless of PEGylation chemistry.

III. Proteins and Peptides

In certain embodiments, the present invention concerns compositions comprising at least one protein or peptide, such as stabilized arginase multimers. These peptides may be comprised in a fusion protein or conjugated to an agent.

A. Proteins and Peptides

As used herein, a protein or peptide generally refers, but is not limited to, a protein of greater than about 200 amino acids, up to a full-length sequence translated from a gene; a polypeptide of greater than about 100 amino acids; and/or a peptide of from about 3 to about 100 amino acids. For convenience, the terms "protein," "polypeptide," and "peptide" are used interchangeably herein.

As used herein, an "amino acid residue" refers to any naturally occurring amino acid, any amino acid derivative or any amino acid mimic known in the art. Exemplary residues of the protein or peptide are sequential, without any non-amino acid interrupting the sequence of amino acid residues. Other exemplary sequences may comprise one or more non-amino acid moieties. For example, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, and may comprise at least one modified or unusual amino acid, including but not limited to those shown below:

| Acronym | Full name |
| --- | --- |
| Aad | 2-Aminoadipic acid |
| Baad | 3-Aminoadipic acid |
| Bala | β-alanine, β-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| Alle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

IV. Nucleic Acids and Vectors

Nucleic acid sequences encoding an arginase polypeptide of interest can be a stabilized multimeric arginase. Depending on which expression system is to be used, nucleic acid sequences can be selected based on conventional methods. For example, human Arginase I and II contain multiple codons that are rarely utilized in *E. coli* that may interfere with expression; therefore, the respective genes or variants thereof may be codon optimized for *E. coli* expression, as described in for example U.S. Pat. No. 8,440,184. Various vectors may be also used to express the protein of interest, such as a fusion multimeric arginase or a cysteine-substituted arginase. Exemplary vectors include, but are not limited to, plasmid vectors, viral vectors, transposon, ghost red blood cells, or liposome-based vectors.

V. Host Cells

Host cells, preferably eukaryotic cells, may be used to transform to allow the expression and secretion of arginase and fusion multimers thereof. The host cells may be bacteria, mammalian cells, yeast, or filamentous fungi. Various bacteria include *Escherichia* and *Bacillus*. Yeasts belonging to the genera *Saccharomyces, Kluyveromyces, Hansenula*, or

*Pichia* can be used as host cell. Various species of filamentous fungi may be used as expression hosts including the following genera: *Aspergillus, Trichoderma, Neurospora, Penicillium, Cephalosporium, Achlya, Podospora, Endothia, Mucor, Cochliobolus*, and *Pyricularia*.

Examples of usable bacterial host organisms include, e.g., *Escherichia coli* MC1061, derivatives of *Bacillus subtilis* BRB1, *Staphylococcus aureus* SAI123, or *Streptococcus lividans*. Exemplary yeasts that can be used as host cells include for example, *Saccharomyces cerevisiae* AH22 and *Schizosaccharomyces pombe*; exemplary filamentous fungi, e.g., *Aspergillus nidulans, Aspergillus awamori*, and *Trichoderma reesei*.

Examples of publically available mammalian host cells include Chinese hamster ovary cells (CHO-K1; American Type Culture Collection (ATCC) No. CCL61), rat pituitary cells (GH$_1$; ATCC CCL82), HeLa S3 cells (ATCC CCL2.2), rat hepatoma cells (H-4-II-E; ATCC CRL 1548), SV40-transformed monkey kidney cells (COS-1; ATCC CRL 1650), and murine embryonic cells (NIH-3T3; ATCC CRL 1658). The foregoing being illustrative but not limitative of the many possible host organisms known in the art.

Mammalian host cells expressing the arginase and/or their fusion multimers are can be under conditions typically employed to culture the parental cell line. Generally, cells are cultured in a standard mammalian cell medium containing physiological salts and nutrients, such as standard Roswell Park Memorial Institute medium (RPMI), Minimum Essential Medium (MEM), Improved Minimum Essential Medium (IMEM) or Dulbecco's Minimum Essential Medium (DMEM), typically supplemented with 5-10% serum, such as fetal bovine serum (FBS). Culture conditions are also standard, e.g., cultures are incubated at 37° C. in stationary or roller cultures until desired levels of the proteins are achieved.

VI. Protein Purification

The protein or polypeptide of interest may be further purified using chromatographic and electrophoretic techniques to achieve partial or complete purification (or purification to homogeneity) unless otherwise specified. Analytical methods particularly suited to the preparation of a pure peptide are ion-exchange chromatography, gel exclusion chromatography, polyacrylamide gel electrophoresis, affinity chromatography, immunoaffinity chromatography, and isoelectric focusing. A particularly efficient method of purifying peptides is fast performance liquid chromatography (FPLC) or even high performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Exemplary protein purification techniques include using ammonium sulphate, PEG, antibodies and the like, or by heat denaturation, followed by: centrifugation; chromatography steps such as ion exchange, gel filtration, reverse phase, hydroxylapatite, and affinity chromatography; isoelectric focusing; gel electrophoresis; and combinations of these and other techniques.

VII. Pharmaceutical Compositions

The arginases described herein can be administered systemically or locally. The arginases and compositions comprising them can be administered intravenously, intrathecally, subcutaneously, intramuscularly, intratumorally, and/or intraperitoneally or a combination thereof. The compounds and compositions comprising them described herein can be administered alone or in combination with arginine scavengers and/or arginine-reduced diets.

Compositions containing an arginase or portion thereof can be provided in formulations together with physiologically tolerable liquid, gel or solid carriers, diluents, and excipients. Such compositions are typically prepared as liquid solutions or suspensions, as injectables. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents. Where clinical applications are contemplated, it may be necessary to prepare pharmaceutical compositions—expression vectors, virus stocks, proteins, antibodies and drugs—in a form appropriate for the intended application. Generally, pharmaceutical compositions of the present invention comprise an effective amount of one or more arginase variants or additional agent dissolved or dispersed in a pharmaceutically acceptable carrier.

The phrases "pharmaceutical or pharmacologically acceptable" refers to molecular entities and compositions that do not produce an adverse, allergic or other untoward reaction when administered to a subject, such as a human, as appropriate. The preparation of a pharmaceutical composition that contains at least one arginase variant, such as a stabilized multimeric arginase or a pegylated arginase isolated by the method disclosed herein, or additional active ingredient will be known to those of skill in the art in light of the present disclosure, as exemplified by REMINGTON'S PHARMACEUTICAL SCIENCES, 18$^{th}$ Ed., 1990. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, dyes, such like materials and combinations thereof, as would be known to one of ordinary skill in the art (see e.g., REMINGTON'S PHARMACEUTICAL SCIENCES, 18$^{th}$ Ed., 1990). 1990). Except insofar as any conventional carrier is incompatible with the active ingredient, its use in the pharmaceutical compositions is contemplated.

The pharmaceutical compositions containing arginase may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intramuscularly, subcutaneously, intratumorally, locally, injection, infusion, continuous infusion, via a catheter, in lipid compositions (e.g., liposomes), or by other method or any combination of the forgoing as would be known to one of ordinary skill in the art (see, e.g., REMINGTON'S PHARMACEUTICAL SCIENCES).

The arginase variants may be formulated into a composition in a free base, neutral or salt form. Pharmaceutically acceptable salts include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions can be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

The compositions for administration can be provided in a pharmaceutically acceptable carrier with or without an inert diluent. The carrier should be capable of assimilating and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the use of preservatives such as various antibacterial and antifungal agents, including but not limited to parabens (e.g., methylparabens, propylparabens), chlorobutanol, phenol, sorbic acid, thimerosal or combinations thereof may improve longevity of the pharmaceutical composition.

The composition can be combined with the carrier in any convenient and practical manner, i.e., by solution, suspension, emulsification, admixture, encapsulation, absorption and the like. Such procedures are routine for those skilled in the art.

A pharmaceutical lipid vehicle can be used for the compositions that include arginase variants. The lipid vehicle compositions can comprise one or more lipids, and an aqueous solvent. As used herein, the term "lipid" will be defined to include any of a broad range of substances that is characteristically insoluble in water and extractable with an organic solvent. Examples include compounds, which contain long-chain aliphatic hydrocarbons and their derivatives. A lipid may be naturally occurring or synthetic (i.e., designed or produced by man). However, a lipid is usually a biological substance. Biological lipids include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

The actual dosage amount of a composition comprising an arginase described herein to a patient can be determined by physical and physiological factors such as body weight, severity of condition, the type of disease being treated, previous or concurrent therapeutic interventions, idiopathy, of the patient and on the route of administration. Depending upon the dosage and the route of administration, the number of administrations of a preferred dosage and/or an effective amount may vary by subject. The dosage will depend on the amount needed for the patient to achieve normal levels of at least one or more of the following: arginine, HArg, ArgA, GVA, GAA, and NAArg. ARG1-D Patient levels of one or more of these five (5) compounds are generally assessed until normal ranges are obtained in the plasma of the patient. Tissue levels of the five (5) compounds can also be assessed, but may not be necessary or may be performed less frequently than plasma level testing.

For an ARG1-D patient, the initial administration may be intravenously of a dosage of 0.005 to 1.00 mg/kg of arginase per kg of patient, as well as any 0.005 amount between the range of 0.005 to 1.00 mg/kg patient weight such as at 0.02 mg/kg or 0.035 mg/kg. An exemplary intravenous dosage or an arginase can be administered daily, weekly, bi-monthly or monthly. Alternatively, arginase compositions can be administered initially or only subcutaneously or in any combination of intravenous or subcutaneous administration. Subcutaneous or intramuscular administration can be at a dosage of 0.01 to 1.50 mg/kg patient weight of an arginase, as well as at 0.01 amount between the range of 0.01 and 1.50 mg/kg patient weight such as at 0.08 mg/kg. The subcutaneous or intramuscular dosing can be daily, weekly, bi-monthly, or monthly.

A pharmaceutical composition may comprise, for example, at least about 0.1% of an active compound. In other embodiments, the active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, and other pharmacological considerations will be contemplated by one skilled in the art of preparing such pharmaceutical formulations, and as such, a variety of dosages and treatment regimens may be desirable. An exemplary formulation of pegzilarginase is formulated in a buffer comprising 5 mM potassium phosphor, 50 mM sodium chloride, and 1.5% glycerol (w/v/) at a pH of 7.4.

VIII. Methods of Treatment

In addition to administering an arginase protein to an ARG1-D patient, other methods of treatment are also contemplated. For example, the patient can be treated via a gene therapy vector, such as an adenovirus-based gene delivery vector comprising the wild-type arginase. The wild-type protein can be directed to specific organs, such as the liver. Various viral packaging systems have been created for reintroducing proteins into patients by gene therapy as for example as described in U.S. Pat. No. 8,398,968.

Another method of treating an ARG1-D patient would be by using a CRISPR (clustered regularly interspaced short palindromic repeats) system, wherein the defective gene on the chromosome is manipulated to edit the errors such that the patient can produce wild-type arginase in normal quantities. As discussed, there are two arginase genes located on different chromosomes that may need to be edited. CRISPR genome engineering is described in for example U.S. Pat. Pub. Nos. 20170240922; 20170283830; 20170224843; and 20170191078.

Another method of delivering the arginase would be encapsulating the arginase protein in a resealed red blood cell (RBC) that can be administered to the patient. Encapsulating the arginase can be performed generally as described in US Pat. Pub. No. 20160095884 and 20140154797. A lysis/resealing process for preparing erythrocytes containing arginase comprises placing a globular concentrate in suspension in an isotonic solution having a hematocrit level which is equal to or greater than 65%, with refrigeration at 1° C. to 8° C.; measuring the osmotic fragility based on a sample of erythrocytes from that same globular concentrate, preferably on a sample of the suspension; lysis and internalization procedure of the active ingredient (i.e. an arginase), inside the same chamber, at a temperature maintained at about 1° C. to 8° C., comprising allowing the erythrocyte suspension having a hematocrit level equal to or greater than 65% and a hypotonic lysis solution which is refrigerated at 1° C. to 8° C., to circulate in a dialysis cartridge; the lysis parameters being adjusted in accordance with the osmotic fragility previously measured; and resealing in a second chamber at a temperature of from 30° C. to 40° C. by means of a hypertonic solution.

EXAMPLE

In an open label phase 1/2 study, the study had an enrollment of 12 adult human and pediatric patients diagnosed with ARG1-D (7 pediatric and 5 adult patients). In Part 1, patients received single ascending doses of pegzilarginase at 2 week intervals. In Part 2, patients received pegzilarginase (AEB1102) intravenously (IV) at weekly intervals for 8 weeks.

Assessments for safety, pharmacokinetics, pharmacodynamics (plasma arginine and GCs (e.g., GVA, ArgA, NAA, GAA)), and standardized clinical measures (e.g., 6-minute walk test (6MWT), Berg Balance Scale (BBS), Gross Motor Function Measure 66 item (GMFM-66), and PROMIS) were made. GMFM-66 is a tool that assesses various aspects of gross motor function from Part A through Part E. Guanidino compounds (GCs) were analyzed both before dosing pegzilarginase and after pegzilarginase dosing to assess therapeutic effect of the pegzilarginase on the patient. GCs chosen for analysis from the patients included α-keto-δ-guanidinovaleric acid (GVA), argininic acid (ArgA), homoarginine, N-α-acetylarginine (NAArg), and GAA in plasma.

Methods. A bioanalytical procedure was developed for the determination of GCs (GAA, GVA, ArgA, and NAArg) from $K_2$EDTA plasma from the patients. Plasma proteins from the patients were precipitated with a 10% trichloroacetic acid solution and separated on a Shimadzu Nexera® using an Imtakt Intrada Amino Acid 50×2 mm (PN: WAA22) column. Analytes were detected by LC-MS/MS using an Applied Biosystems/MDS Sciex API 5500™. Isotope labelled standards of each GC were used to enable quantification of each plasma sample. The detailed method protocol is provided at the end of this example.

Results of Study from Two Adult Female Patients

Two adult female patients, ages 24 and 25 years, were treated with weekly pegzilarginase by IV for 8 weeks. Both patients have moderate to severe neurocognitive and neuromotor deficits, including spasticity. Both patients continued their pre-pegzilarginase treatment standard of care throughout the course of the pegzilarginase administration.

Weekly intravenous (IV) doses of 0.04 mg/kg of pegzilarginase were well tolerated. A time dependent decrease in the concentration of the assayed GCs (e.g., ArgA, NAArg, and GVA) was observed after treatment with pegzilarginase, in addition to the expected decreases in plasma arginine (FIG. 1). The decreases in ArgA, NAArg, and GVA plasma levels occurred within 24 hours of the first infusion and continued to be maintained below baseline levels through the 8 weeks of dosing received by each patient.

Plasma samples from both patients originally used for Arginine/Ornithine sample analysis in the single ascending dose portion of the Phase 1 study (pegzilarginase-101A) were pooled to assist with setting the assay ranges during GC method development. These pooled samples were then used to quantitate GCs after the method development phase was complete. Both patients received pegzilarginase at single doses of 0.015 mg/kg and 0.03 mg/kg patient body weight with a 2-week observation period between doses.

Using these pooled patient samples in the previously described non-GLP assay (detailed method provided at the end of the example), a time-dependent decrease was observed in the concentration of ArgA (approximately 3-fold), GVA (approximately 4-fold), and NAArg (approximately 2-fold) from the ARG1-D patients treated with 0.03 mg/kg of pegzilarginase. The decrease in the GC levels parallels the decrease in plasma arginine, which was determined using a GLP assay (FIG. 1A-D).

As reflected in FIG. 3A-D, the two patients (i.e., 120-101 and 120-102) were administered pegzilarginase at 0.015 mg/kg patient weight or at 0.03 mg/kg patient weight with arginine and guanadino compound levels in plasma being measured as follows:

TABLE 2

| GC levels in two patients at a dosage of 0.015 mg/kg patient. | | | | | |
|---|---|---|---|---|---|
| Time point (hr) | Arginine (μM)* | Argininic acid (μM)** | α-K-δ-guani-dinovaleric acid (μM)** | Homo-arginine (μM)** | α-N-acetyl arginine (μM)** |
| 0 | 240 | 3.11 | 3.92 | 19.1 | 2.22 |
| 0.25 | 193 | 2.45 | 4.69 | 17.7 | 0.588 |
| 1 | 194 | 2.98 | 6.31 | 18.6 | 0.716 |

TABLE 2-continued

| GC levels in two patients at a dosage of 0.015 mg/kg patient. | | | | | |
|---|---|---|---|---|---|
| Time point (hr) | Arginine (μM)* | Argininic acid (μM)** | α-K-δ-guani-dinovaleric acid (μM)** | Homo-arginine (μM)** | α-N-acetyl arginine (μM)** |
| 2 | 151 | | | | |
| 4 | 131 | 3.45 | 7.96 | 21.1 | 0.994 |
| 8 | 82.7 | | | | |
| 12 | 101 | | | | |
| 24 | 111 | | | | |
| 48 | 110 | | | | |
| 72 | 122 | 2 | 2.58 | 22.2 | 0.603 |
| 144 | 176 | | | | |
| 168 | 170 | 2.48 | 4.29 | 22.5 | 0.85 |

*Mean of two subjects;

**pooled sample from two subjects. If no values are listed in Tables 2 and 3, the patient was not tested at that time point as the assays are expensive, and generally blood levels were not believed to change that rapidly.

TABLE 3

| GC levels in two patients at a dosage of 0.03 mg/kg patient weight. | | | | | |
|---|---|---|---|---|---|
| Time point (hr) | Arginine (μM)* | Argininic acid (μM)** | α-K-δ-guani-dinovaleric acid (μM)** | Homo-arginine (μM)** | α-N-acetyl arginine (μM)** |
| 0 | 294 | 3.55 | 7.6 | 14.9 | 0.619 |
| 0.25 | 144 | 3.47 | 7.54 | 13 | 0.653 |
| 1 | 118 | 4.07 | 5.78 | 12 | 0.503 |
| 2 | 96.5 | | | | |
| 4 | 76.4 | 2.89 | 3.86 | 9.83 | 0.308 |
| 8 | 67.7 | | | | |
| 12 | 52.3 | | | | |
| 24 | 78.1 | | | | |
| 48 | 68.3 | | | | |
| 72 | 76.3 | 1.08 | 1.51 | 18.9 | 0.225 |
| 144 | 165 | | | | |
| 168 | 151 | 2.5 | 4.94 | 11.3 | 0.502 |

*Mean of two subjects,
**pooled sample from two subjects.

TABLE 4

| Dosages and testing of concentrations occurred as follows: | | | | | | | |
|---|---|---|---|---|---|---|---|
| Subject | Study Part | Week | Sample Description | Actual Sampling Date | Actual Sampling Time | Dilution Factor | Arginine Concentration μM |
| Screening | | | | | | | |
| 120-101 | Escalation | 0 | Screen 1 | 25 Aug. 2016 | 10:34:00 | 1 | 484 |
| 120-101 | Escalation | 0 | Screen 2 | 29 Aug. 2016 | 08:52:00 | 1 | 408 |
| 120-101 | Escalation | 0 | Screen 3 | 30 Aug. 2016 | 08:00:00 | 1 | 496 |
| Escalation Dose 1 - 0.015 mg/kg | | | | | | | |
| 120-101 | Escalation | 1 | 12-18 Hours Predose | 12 Sep. 2016 | 08:55:00 | 1 | 419 |
| 120-101 | Escalation | 1 | Predose | 13 Sep. 2016 | 09:20:00 | 1 | 390 |
| 120-101 | Escalation | 1 | SOI + 15 minutes | 13 Sep. 2016 | 10:54:00 | 1 | 260 |
| 120-101 | Escalation | 1 | SOI + 1 hour | 13 Sep. 2016 | 11:36:00 | 1 | 295 |
| 120-101 | Escalation | 1 | SOI + 2 hours | 13 Sep. 2016 | 12:39:00 | 1 | 289 |
| 120-101 | Escalation | 1 | SOI + 4 hours | 13 Sep. 2016 | 14:36:00 | 1 | 206 |
| 120-101 | Escalation | 1 | SOI + 8 hours | 13 Sep. 2016 | 18:50:00 | 1 | 213 |
| 120-101 | Escalation | 1 | SOI + 12 hours | 13 Sep. 2016 | 22:39:00 | 1 | 238 |

TABLE 4-continued

| | | | | Actual | Actual | | Arginine |
| | | | Sample | Sampling | Sampling | Dilution | Concentration |
| Subject | Study Part | Week | Description | Date | Time | Factor | μM |
|---|---|---|---|---|---|---|---|
| | | | | Dosages and testing of concentrations occurred as follows: | | | |
| 120-101 | Escalation | 1 | SOI + 24 hours | 14 Sep. 2016 | 10:36:00 | 1 | 250 |
| 120-101 | Escalation | 1 | SOI + 48 hours | 15 Sep. 2016 | 11:18:00 | 1 | 174 |
| 120-101 | Escalation | 1 | SOI + 72 hours | 16 Sep. 2016 | 11:10:00 | 1 | 235 |
| 120-101 | Escalation | 1 | SOI + 120 hours | 19 Sep. 2016 | 11:00:00 | 1 | 284 |
| 120-101 | Escalation | 2 | Week 2 Day 1 | 20 Sep. 2016 | 09:45:00 | 1 | 285 |
| | | | Escalation Dose 2 - 0.03 mg/kg | | | | |
| 120-101 | Escalation | 3 | 12-18 Hours Predose | 26 Sep. 2016 | 14:15:00 | 1 | 306 |
| 120-101 | Escalation | 3 | Predose | 27 Sep. 2016 | 08:56:00 | 1 | 294 |
| 120-101 | Escalation | 3 | SOI + 15 minutes | 27 Sep. 2016 | 10:30:00 | 1 | 144 |
| 120-101 | Escalation | 3 | SOI + 1 hour | 27 Sep. 2016 | 11:11:00 | 1 | 118 |
| 120-101 | Escalation | 3 | SOI + 2 hours | 27 Sep. 2016 | 12:10:00 | 1 | 96.5 |
| 120-101 | Escalation | 3 | SOI + 4 hours | 27 Sep. 2016 | 14:10:00 | 1 | 76.4 |
| 120-101 | Escalation | 3 | SOI + 8 hours | 27 Sep. 2016 | 18:08:00 | 1 | 67.7 |
| 120-101 | Escalation | 3 | SOI + 12 hours | 27 Sep. 2016 | 22:09:00 | 1 | 52.3 |
| 120-101 | Escalation | 3 | SOI + 24 hours | 28 Sep. 2016 | 10:11:00 | 1 | 78.1 |
| 120-101 | Escalation | 3 | SOI + 48 hours | 29 Sep. 2016 | 09:40:00 | 1 | 68.3 |
| 120-101 | Escalation | 3 | SOI + 72 hours | 30 Sep. 2016 | 08:40:00 | 1 | 76.3 |
| 120-101 | Escalation | 3 | SOI + 120 hours | 03 Oct. 2016 | 09:45:00 | 1 | 165 |
| 120-101 | Escalation | 4 | Week 4 Day 1 | 04 Oct. 2016 | 08:40:00 | 1 | 151 |
| | | | Escalation Dose 3 - 0.06 mg/kg | | | | |
| 120-101 | Escalation | 5 | 12-18 Hours Predose | 10 Oct. 2016 | 15:43:00 | 1 | 235 |
| 120-101 | Escalation | 5 | Predose | 11 Oct. 2016 | 09:27:00 | 1 | 268 |
| 120-101 | Escalation | 5 | SOI + 15 minutes | 11 Oct. 2016 | 10:37:00 | 1 | 49.5 |
| 120-101 | Escalation | 5 | SOI + 1 hour | 11 Oct. 2016 | 11:24:00 | 1 | 46.6 |
| 120-101 | Escalation | 5 | SOI + 2 hours | 11 Oct. 2016 | 12:24:00 | 1 | 32.8 |
| 120-101 | Escalation | 5 | SOI + 4 hours | 11 Oct. 2016 | 14:50:00 | 1 | 9.96 |
| 120-101 | Escalation | 5 | SOI + 8 hours | 11 Oct. 2016 | 18:20:00 | 1 | 18.3 |
| 120-101 | Escalation | 5 | SOI + 12 hours | 11 Oct. 2016 | 20:31:00 | 1 | 20 |
| 120-101 | Escalation | 5 | SOI + 24 hours | 12 Oct. 2016 | 10:21:00 | 1 | 23.9 |
| 120-101 | Escalation | 5 | SOI + 48 hours | 13 Oct. 2016 | 10:53:00 | 1 | 25.4 |
| 120-101 | Escalation | 5 | SOI + 72 hours | 14 Oct. 2016 | 09:31:00 | 1 | 40.7 |
| 120-101 | Escalation | 5 | SOI + 120 hours | 17 Oct. 2016 | 10:14:00 | 1 | 134 |
| 120-101 | Escalation | 6 | Week 6 Day 1 | 20 Oct. 2016 | 10:17:00 | 1 | 201 |
| 120-101 | Escalation | 7 | 12-18 Hours Predose | 24 Oct. 2016 | 10:27:00 | 1 | 230 |
| 120-101 | Escalation | 7 | Predose | 25 Oct. 2016 | 09:25:00 | 1 | 206 |
| 120-101 | Escalation | 10 | Week 10 Day 1 | 08 Nov. 2016 | 09:05:00 | 1 | 262 |
| | | | Multi-dose Baseline | | | | |
| 120-101 | Multi-dose | 0 | Baseline 1 | 16 Aug. 2017 | 09:03:00 | 1 | 353 |
| 120-101 | Multi-dose | 0 | Baseline 2 | 17 Aug. 2017 | 09:10:00 | 1 | 377 |
| 120-101 | Multi-dose | 0 | Baseline 3 | 18 Aug. 2017 | 08:45:00 | 1 | 383 |
| | | | Multi-dose Dose 1 - 0.04 mg/kg | | | | |
| 120-101 | Multi-dose | 1 | Predose | 22 Aug. 2017 | 09:10:00 | 1 | 306 |
| 120-101 | Multi-dose | 1 | End of Infusion | 22 Aug. 2017 | 10:57:00 | 1 | 123 |
| 120-101 | Multi-dose | 1 | EOI + 4 Hours | 22 Aug. 2017 | 14:39:00 | 1 | 91.6 |
| 120-101 | Multi-dose | 1 | EOI + 8 Hours | 22 Aug. 2017 | 18:34:00 | 1 | 77.4 |
| 120-101 | Multi-dose | 1 | EOI + 24 Hours | 23 Aug. 2017 | 10:05:00 | 1 | 7.96 |
| 120-101 | Multi-dose | 1 | EOI + 48 Hours | 24 Aug. 2017 | 09:27:00 | 1 | 34.8 |
| | | | Multi-dose Dose 2 - 0.04 mg/kg (single pre-dose measurement) | | | | |
| 120-101 | Multi-dose | 2 | Week 2 Day 1 | 27 Aug. 2017 | 09:50:00 | 1 | 149 |
| | | | Multi-dose Dose 3 - 0.04 mg/kg (single pre-dose measurement) | | | | |
| 120-101 | Multi-dose | 3 | Week 3 Day 1 | 05 Sep. 2017 | 09:28:00 | 1 | 117 |
| | | | Screening | | | | |
| 120-102 | Escalation | 0 | Screen 1 | 25 Aug. 2016 | 10:34:00 | 1 | 325 |
| 120-102 | Escalation | 0 | Screen 2 | 29 Aug. 2016 | 08:52:00 | 1 | 362 |
| 120-102 | Escalation | 0 | Screen 3 | 30 Aug. 2016 | 08:00:00 | 1 | 300 |

TABLE 4-continued

| | | | | | | | |
|---|---|---|---|---|---|---|---|
| | | | | | | Arginine | |
| | | | | Actual | Actual | | |
| | | | Sample | Sampling | Sampling | Dilution | Concentration |
| Subject | Study Part | Week | Description | Date | Time | Factor | μM |

Dosages and testing of concentrations occurred as follows:

| | | | | | | | |
|---|---|---|---|---|---|---|---|
| | | | Escalation Dose 1 - 0.015 mg/kg | | | | |
| 120-102 | Escalation | 1 | 12-18 Hours Predose | 12 Sep. 2016 | 09:00:00 | 1 | 231 |
| 120-102 | Escalation | 1 | Predose | 13 Sep. 2016 | 09:50:00 | 1 | 249 |
| 120-102 | Escalation | 1 | SOI + 15 minutes | 13 Sep. 2016 | 11:35:00 | 1 | 193 |
| 120-102 | Escalation | 1 | SOI + 1 hour | 13 Sep. 2016 | 12:20:00 | 1 | 194 |
| 120-102 | Escalation | 1 | SOI + 2 hours | 13 Sep. 2016 | 13:21:00 | 1 | 151 |
| 120-102 | Escalation | 1 | SOI + 4 hours | 13 Sep. 2016 | 15:13:00 | 1 | 131 |
| 120-102 | Escalation | 1 | SOI + 8 hours | 13 Sep. 2016 | 19:16:00 | 1 | 82.7 |
| 120-102 | Escalation | 1 | SOI + 12 hours | 13 Sep. 2016 | 23:18:00 | 1 | 101 |
| 120-102 | Escalation | 1 | SOI + 24 hours | 14 Sep. 2016 | 11:28:00 | 1 | 111 |
| 120-102 | Escalation | 1 | SOI + 48 hours | 15 Sep. 2016 | 11:29:00 | 1 | 110 |
| 120-102 | Escalation | 1 | SOI + 72 hours | 16 Sep. 2016 | 11:20:00 | 1 | 122 |
| 120-102 | Escalation | 1 | SOI + 120 hours | 19 Sep. 2016 | 11:05:00 | 1 | 176 |
| 120-102 | Escalation | 2 | Week 2 Day 1 | 20 Sep. 2016 | 09:58:00 | 1 | 170 |
| | | | Escalation Dose 2 - 0.03 mg/kg | | | | |
| 120-102 | Escalation | 3 | 12-18 Hours Predose | 26 Sep. 2016 | 14:25:00 | 1 | 227 |
| 120-102 | Escalation | 3 | Predose | 27 Sep. 2016 | 08:26:00 | 1 | 195 |
| 120-102 | Escalation | 3 | SOI + 15 minutes | 27 Sep. 2016 | 09:50:00 | 1 | 79.2 |
| 120-102 | Escalation | 3 | SOI + 1 hour | 27 Sep. 2016 | 10:35:00 | 1 | 55 |
| 120-102 | Escalation | 3 | SOI + 2 hours | 27 Sep. 2016 | 11:35:00 | 1 | 69.8 |
| 120-102 | Escalation | 3 | SOI + 4 hours | 27 Sep. 2016 | 13:44:00 | 1 | 36.5 |
| 120-102 | Escalation | 3 | SOI + 8 hours | 27 Sep. 2016 | 17:28:00 | 1 | 45.9 |
| 120-102 | Escalation | 3 | SOI + 12 hours | 27 Sep. 2016 | 21:22:00 | 1 | 22.6 |
| 120-102 | Escalation | 3 | SOI + 24 hours | 28 Sep. 2016 | 09:17:00 | 1 | 44.4 |
| 120-102 | Escalation | 3 | SOI + 48 hours | 29 Sep. 2016 | 09:34:00 | 1 | 50.5 |
| 120-102 | Escalation | 3 | SOI + 72 hours | 30 Sep. 2016 | 09:30:00 | 1 | 56.9 |
| 120-102 | Escalation | 3 | SOI + 120 hours | 03 Oct. 2016 | 10:00:00 | 1 | 138 |
| 120-102 | Escalation | 4 | Week 4 Day 1 | 04 Oct. 2016 | 08:36:00 | 1 | 110 |
| 120-102 | Escalation | 5 | 12-18 Hours Predose | 10 Oct. 2016 | 15:15:00 | 1 | 177 |
| 120-102 | Escalation | 5 | Predose | 11 Oct. 2016 | 08:45:00 | 1 | 158 |
| 120-102 | Escalation | 10 | Week 10 Day 1 | 25 Oct. 2016 | 09:55:00 | 1 | 228 |
| | | | Multi-dose Baseline | | | | |
| 120-102 | Multi-dose | 0 | Baseline 1 | 16 Aug. 2017 | 08:55:00 | 1 | 307 |
| 120-102 | Multi-dose | 0 | Baseline 2 | 17 Aug. 2017 | 09:20:00 | 1 | 376 |
| 120-102 | Multi-dose | 0 | Baseline 3 | 18 Aug. 2017 | 08:50:00 | 1 | 314 |
| | | | Multi-dose Dose 1 - 0.04 mg/kg | | | | |
| 120-102 | Multi-dose | 1 | Predose | 22 Aug. 2017 | 09:19:00 | 1 | 263 |
| 120-102 | Multi-dose | 1 | End of Infusion | 22 Aug. 2017 | 10:25:00 | 1 | 100 |
| 120-102 | Multi-dose | 1 | EOI + 4 Hours | 22 Aug. 2017 | 14:07:00 | 1 | 53 |
| 120-102 | Multi-dose | 1 | EOI + 8 Hours | 22 Aug. 2017 | 18:10:00 | 1 | 42.6 |
| 120-102 | Multi-dose | 1 | EOI + 24 Hours | 23 Aug. 2017 | 09:45:00 | 1 | 45.4 |
| 120-102 | Multi-dose | 1 | EOI + 48 Hours | 24 Aug. 2017 | 09:17:00 | 1 | 40.6 |
| | | | Multi-dose Dose 2 - 0.04 mg/kg (single pre-dose measurement) | | | | |
| 120-102 | Multi-dose | 2 | Week 2 Day 1 | 29 Aug. 2017 | 09:48:00 | 1 | 141 |
| | | | Multi-dose Dose 3 - 0.04 mg/kg (single pre-dose measurement) | | | | |
| 120-102 | Multi-dose | 3 | Week 3 Day 1 | 05 Sep. 2017 | 09:13:00 | 1 | 155 |

Note that due to patient scheduling, the samples planned for 120 hours were actually drawn at 144 hours

TABLE 5

PK Concentrations (concentration data available
for dose escalation part of trial);
The PK data for the two patients is as follows:

| Subject | Week | Time point | Collection Date | Collection Time | Aliquot Factor | Conc. (μg/mL) |
|---|---|---|---|---|---|---|
| | | | Escalation Dose 1 - 0.015 mg/kg | | | |
| 120-101 | Week 1 | Predose | Sep. 12, 2016 | 8:58 | 1 | BQL |
| 120-101 | Week 1 | Predose | Sep. 13, 2016 | 9:20 | 1 | BQL |
| 120-101 | Week 1 | 15 min | Sep. 13, 2016 | 10:51 | 1 | 0.407 |
| 120-101 | Week 1 | 1 hr | Sep. 13, 2016 | 11:36 | 1 | 0.357 |
| 120-101 | Week 1 | 2 hr | Sep. 13, 2016 | 12:39 | 1 | 0.355 |
| 120-101 | Week 1 | 4 hr | Sep. 13, 2016 | 14:36 | 1 | 0.306 |
| 120-101 | Week 1 | 8 hr | Sep. 13, 2016 | 18:50 | 1 | 0.297 |
| 120-101 | Week 1 | 12 hr | Sep. 13, 2016 | 22:39 | 1 | BQL |
| 120-101 | Week 1 | 24 hr | Sep. 14, 2016 | 10:36 | 1 | BQL |
| 120-101 | Week 1 | 48 hr | Sep. 15, 2016 | 11:11 | 1 | BQL |
| 120-101 | Week 1 | 72 hr | Sep. 16, 2016 | 11:10 | 1 | BQL |
| 120-101 | Week 1 | 120 hr | Sep. 19, 2016 | 11:00 | 1 | BQL |
| 120-101 | Week 2 | During Visit | Sep. 20, 2016 | 9:45 | 1 | BQL |
| | | | Escalation Dose 2 - 0.03 mg/kg | | | |
| 120-101 | Week 3 | Predose | Sep. 26, 2016 | 14:15 | 1 | BQL |
| 120-101 | Week 3 | Predose | Sep. 27, 2016 | 8:56 | 1 | BQL |
| 120-101 | Week 3 | 15 min | Sep. 27, 2016 | 10:30 | 1 | 0.993 |
| 120-101 | Week 3 | 1 hr | Sep. 27, 2016 | 11:10 | 1 | 0.962 |
| 120-101 | Week 3 | 2 hr | Sep. 27, 2016 | 12:10 | 1 | 0.847 |
| 120-101 | Week 3 | 4 hr | Sep. 27, 2016 | 14:10 | 1 | 0.728 |
| 120-101 | Week 3 | 8 hr | Sep. 27, 2016 | 18:08 | 1 | 0.740 |
| 120-101 | Week 3 | 12 hr | Sep. 27, 2016 | 22:09 | 1 | 0.622 |
| 120-101 | Week 3 | 48 hr | Sep. 28, 2016 | 9:34 | 1 | 0.253 |
| 120-101 | Week 3 | 24 hr | Sep. 28, 2016 | 10:11 | 1 | 0.467 |
| 120-101 | Week 3 | 72 hr | Sep. 29, 2016 | 9:36 | 1 | BQL |
| 120-101 | Week 3 | 120 hr | Oct. 3, 2016 | 9:45 | 1 | BQL |
| 120-101 | Week 4 | During Visit | Oct. 4, 2016 | 8:40 | 1 | BQL |
| | | | Escalation Dose 3 - 0.06 mg/kg | | | |
| 120-101 | Week 5 | Predose | Oct. 10, 2016 | 15:43 | 1 | BQL |
| 120-101 | Week 5 | Predose | Oct. 11, 2016 | 9:25 | 1 | BQL |
| 120-101 | Week 5 | 15 min | Oct. 11, 2016 | 10:37 | 1 | 1.98 |
| 120-101 | Week 5 | 1 hr | Oct. 11, 2016 | 11:24 | 1 | 1.88 |
| 120-101 | Week 5 | 2 hr | Oct. 11, 2016 | 12:24 | 1 | 1.86 |
| 120-101 | Week 5 | 4 hr | Oct. 11, 2016 | 14:50 | 1 | 1.68 |
| 120-101 | Week 5 | 8 hr | Oct. 11, 2016 | 18:15 | 1 | 1.54 |
| 120-101 | Week 5 | 12 hr | Oct. 11, 2016 | 22:31 | 1 | 1.34 |
| 120-101 | Week 5 | 24 hr | Oct. 12, 2016 | 10:21 | 1 | 1.02 |
| 120-101 | Week 5 | 48 hr | Oct. 13, 2016 | 10:53 | 1 | 0.598 |
| 120-101 | Week 5 | 72 hr | Oct. 14, 2016 | 9:31 | 1 | 0.388 |
| 120-101 | Week 5 | 120 hr | Oct. 17, 2016 | 10:14 | 1 | BQL |

TABLE 5-continued

PK Concentrations (concentration data available
for dose escalation part of trial);
The PK data for the two patients is as follows:

| Subject | Week | Time point | Collection Date | Collection Time | Aliquot Factor | Conc. (μg/mL) |
|---|---|---|---|---|---|---|
| 120-101 | Week 6 | During Visit | Oct. 20, 2016 | 10:17 | 1 | BQL |
| 120-101 | Week 7 | Predose | Oct. 24, 2016 | 10:27 | 1 | BQL |
| 120-101 | Week 7 | 1 hr | Oct. 25, 2016 | 9:25 | 1 | BQL |
| 120-101 | Week 10 | During Visit | Nov. 8, 2016 | 9:05 | 1 | BQL |
| | | | Escalation Dose 1 - 0.015 mg/kg | | | |
| 120-102 | Week 1 | Predose | Sep. 12, 2016 | 9:00 | 1 | BQL |
| 120-102 | Week 1 | Predose | Sep. 13, 2016 | 9:50 | 1 | BQL |
| 120-102 | Week 1 | 15 min | Sep. 13, 2016 | 11:35 | 1 | 0.331 |
| 120-102 | Week 1 | 1 hr | Sep. 13, 2016 | 12:20 | 1 | 0.366 |
| 120-102 | Week 1 | 2 hr | Sep. 13, 2016 | 13:20 | 1 | 0.329 |
| 120-102 | Week 1 | 4 hr | Sep. 13, 2016 | 15:13 | 1 | 0.301 |
| 120-102 | Week 1 | 8 hr | Sep. 13, 2016 | 19:16 | 1 | 0.252 |
| 120-102 | Week 1 | 12 hr | Sep. 13, 2016 | 23:18 | 1 | BQL |
| 120-102 | Week 1 | 24 hr | Sep. 14, 2016 | 11:28 | 1 | BQL |
| 120-102 | Week 1 | 48 hr | Sep. 15, 2016 | 11:20 | 1 | BQL |
| 120-102 | Week 1 | 72 hr | Sep. 16, 2016 | 11:20 | 1 | BQL |
| 120-102 | Week 1 | 120 hr | Sep. 19, 2016 | 11:05 | 1 | BQL |
| 120-102 | Week 2 | During Visit | Sep. 20, 2016 | 9:58 | 1 | BQL |
| | | | Escalation Dose 2 - 0.03 mg/kg | | | |
| 120-102 | Week 3 | Predose | Sep. 26, 2016 | 14:25 | 1 | BQL |
| 120-102 | Week 3 | Predose | Sep. 27, 2016 | 8:34 | 1 | BQL |
| 120-102 | Week 3 | 15 min | Sep. 27, 2016 | 9:50 | 1 | 0.904 |
| 120-102 | Week 3 | 1 hr | Sep. 27, 2016 | 10:35 | 1 | 0.918 |
| 120-102 | Week 3 | 2 hr | Sep. 27, 2016 | 11:35 | 1 | 0.829 |
| 120-102 | Week 3 | 4 hr | Sep. 27, 2016 | 13:44 | 1 | 0.767 |
| 120-102 | Week 3 | 8 hr | Sep. 27, 2016 | 17:28 | 1 | 0.671 |
| 120-102 | Week 3 | 12 hr | Sep. 27, 2016 | 21:22 | 1 | 0.577 |
| 120-102 | Week 3 | 24 hr | Sep. 28, 2016 | 9:17 | 1 | 0.373 |
| 120-102 | Week 3 | 48 hr | Sep. 28, 2016 | 9:40 | 1 | BQL |
| 120-102 | Week 3 | 72 hr | Sep. 29, 2016 | 9:30 | 1 | BQL |
| 120-102 | Week 3 | 120 hr | Oct. 3, 2016 | 10:00 | 1 | BQL |
| 120-102 | Week 4 | During Visit | Oct. 4, 2016 | 8:36 | 1 | BQL |
| 120-102 | Week 5 | Predose | Oct. Oct. 2016 | 15:15 | 1 | BQL |
| 120-102 | Week 5 | Predose | Oct. 11, 2016 | 8:38 | 1 | BQL |
| 120-102 | Week 10 | During Visit | Oct. 25, 2016 | 9:55 | 1 | BQL |

Note that due to patient scheduling, the samples planned for 120 hours were actually drawn at 144 hours. Additionally, the PK and pharmacodynamics (PD) data were provided by different vendors, thus the formatting of the two datasets will differ.

TABLE 6

Individual and Mean PK Parameters for Pegzilarginase in Hyperargininemia
Patients After a Single IV Infusion (data available for dose escalation only).

| Dose (mg/kg) | Subject | $R^2$ | $T_{1/2}$ (hr) | $T_{max}$ (hr) | $C_{max}$ (μg/mL) | $T_{last}$ (hr) | $AUC_{0-t}$ (hr*μg/mL) | $AUC_{0-168}$ (hr*μg/mL) | $AUC_{0-00}$ (hr*μg/mL) | AUC Extrap. (%) | CL (mL/hr/kg) | $V_{SS}$ (mL/kg) |
|---|---|---|---|---|---|---|---|---|---|---|---|---|
| 0.015 | 120-101 | 0.813 | 24.6 | 0.25 | 0.407 | 8.0 | 2.56 | 12.9 | 12.9 | 80.1 | 1.17 | 41.4 |
| | 120-102 | 1.00 | 15.6 | 1.0 | 0.366 | 8.0 | 2.38 | 8.05 | 8.05 | 70.4 | 1.86 | 42.0 |
| | N | | 2 | 2 | 2 | 2 | 2 | 2 | 2 | 2 | 2 | 2 |
| | Mean | | 20.1 | 0.63 | 0.387 | 8.0 | 2.47 | 10.5 | 10.5 | 75.3 | 1.51 | 41.7 |
| | SD | | NR | NR | NR | NR | NR | NR | NR | NR | NR | NR |
| | Min | | 15.6 | 0.25 | 0.366 | 8.0 | 2.38 | 8.05 | 8.05 | 70.4 | 1.17 | 41.4 |
| | Median | | 20.1 | 0.63 | 0.387 | 8.0 | 2.47 | 10.5 | 10.5 | 75.3 | 1.51 | 41.7 |
| | Max | | 24.6 | 1.0 | 0.407 | 8.0 | 2.56 | 12.9 | 12.9 | 80.1 | 1.86 | 42.0 |
| | CV % | | NR | NR | NR | NR | NR | NR | NR | NR | NR | NR |

TABLE 6-continued

Individual and Mean PK Parameters for Pegzilarginase in Hyperargininemia
Patients After a Single IV Infusion (data available for dose escalation only).

| Dose (mg/ kg) | Subject | $R^2$ | $T_{1/2}$ (hr) | $T_{max}$ (hr) | $C_{max}$ (µg/ mL) | $T_{last}$ (hr) | $AUC_{0-t}$ (hr*µg/ mL) | $AUC_{0-168}$ (hr*µg/ mL) | $AUC_{0-00}$ (hr*µg/ mL) | AUC Extrap. (%) | CL (mL/hr/ kg) | $V_{SS}$ (mL/ kg) |
|---|---|---|---|---|---|---|---|---|---|---|---|---|
| 0.03 | 120- 101 | 1.00 | 27.7 | 0.25 | 0.993 | 48 | 23.9 | 33.5 | 34.0 | 29.8 | 0.883 | 34.9 |
| | 120- 102 | 1.00 | 18.9 | 1.0 | 0.918 | 24 | 14.2 | 24.4 | 24.4 | 41.7 | 1.23 | 33.6 |
| | N | | 2 | 2 | 2 | 2 | 2 | 2 | 2 | 2 | 2 | 2 |
| | Mean | | 23.3 | 0.625 | 0.956 | 36 | 19.0 | 28.9 | 29.2 | 35.7 | 1.06 | 34.3 |
| | SD | | NR | NR | NR | NR | NR | NR | NR | NR | NR | NR |
| | Min | | 18.9 | 0.250 | 0.918 | 24 | 14.2 | 24.4 | 24.4 | 29.8 | 0.883 | 33.6 |
| | Median | | 23.3 | 0.625 | 0.956 | 36 | 19.0 | 28.9 | 29.2 | 35.7 | 1.06 | 34.3 |
| | Max | | 27.7 | 1.0 | 0.993 | 48 | 23.9 | 33.5 | 34.0 | 41.7 | 1.23 | 34.9 |
| | CV % | | NR | NR | NR | NR | NR | NR | NR | NR | NR | NR |
| 0.06 | 120- 101 | 0.997 | 33.4 | 0.25 | 1.98 | 72 | 64.0 | 80.0 | 82.2 | 22.2 | 0.730 | 34.6 |
| | N | | 1 | 1 | 1 | 1 | 1.0 | 1.0 | 1 | 1 | 1 | 1 |
| | Mean | | 33.4 | 0.25 | 1.98 | 72 | 64.0 | 80.0 | 82.2 | 22.2 | 0.730 | 34.6 |
| | SD | | NR | NR | NR | NR | NR | NR | NR | NR | NR | NR |
| | Min | | 33.4 | 0.25 | 1.98 | 72 | 64.0 | 80.0 | 82.2 | 22.2 | 0.730 | 34.6 |
| | Median | | 33.4 | 0.25 | 1.98 | 72 | 64.0 | 80.0 | 82.2 | 22.2 | 0.730 | 34.6 |
| | Max | | 33.4 | 0.25 | 1.98 | 72 | 64.0 | 80.0 | 82.2 | 22.2 | 0.730 | 34.6 |
| | CV % | | NR | NR | NR | NR | NR | NR | NR | NR | NR | NR |

CV: coefficient of variation;
NR: not reported (N < 3).

Data. The relationship observed between plasma arginine and the ArgA, GVA, and NAArg concentrations is generally consistent with the data published by Marescau et al., (1990) in their analysis of patients, who were maintained on a protein restricted diet. In the Marescau et al., (1990) study, the levels of the GCs decreased concomitantly with the decrease in arginine levels.

Figure 2A:
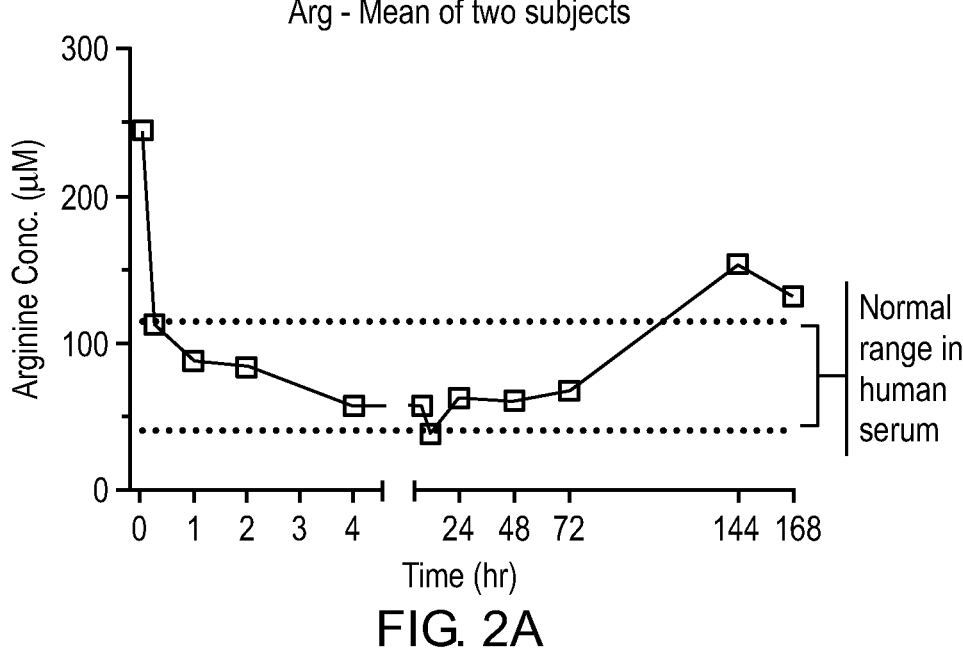
FIG. 2. Plasma concentration of FIG. 2A Arginine and FIG. 2B Homo-arginine (HArg) are shown. Arginine levels are the mean of the values obtained from the two ARG1-D patients treated with 0.03 mg/kg pegzilarginase, using a validated (GLP) assay. HArg values were obtained with a non-GLP assay using pooled samples from the same two ARG1-D patients treated with 0.03 mg/kg pegzilarginase. The "*" indicates the normal range in human serum is as described in Lüneburg, N. et al., (2011), for arginine, or Marescau et al., (1990) for guanidino compounds. The normal range of HArg is <0.500 µmol/L to 2.80 µmol/L.
Figure 2B:
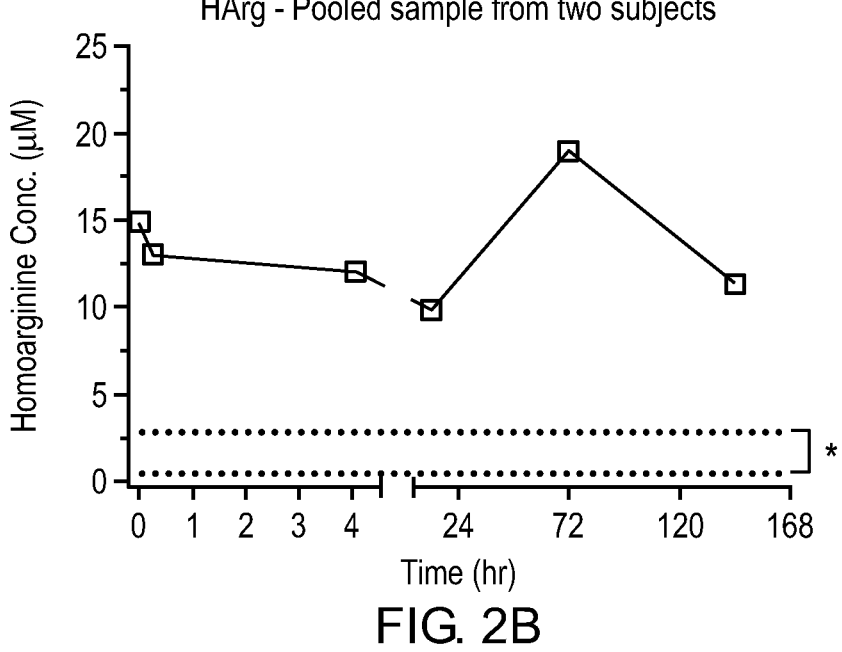
Figure 3A:
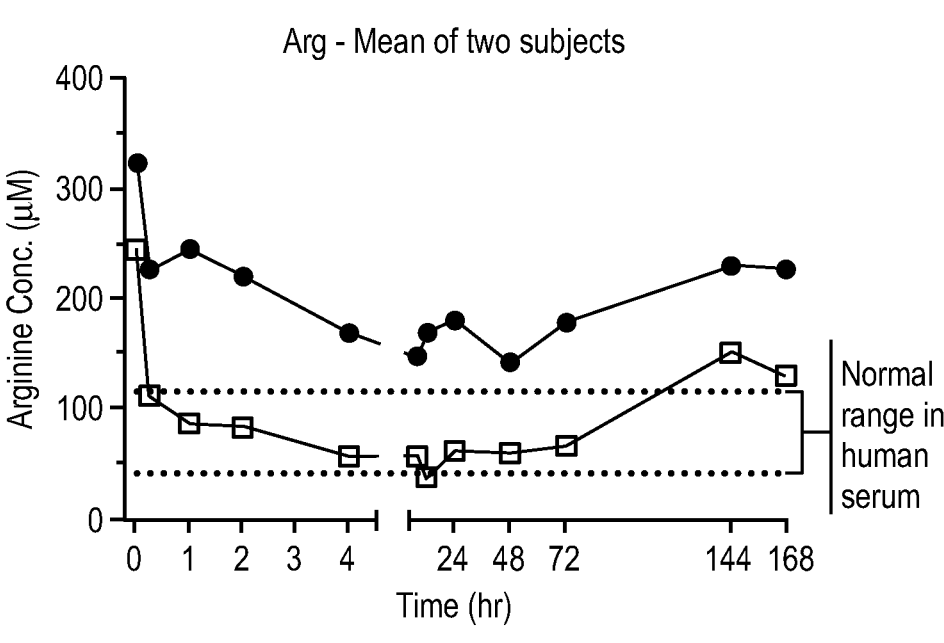
FIG. 3. Plasma concentration of FIG. 3A Arginine, FIG. 3B argininic acid (ArgA), FIG. 3C GVA, and FIG. 3D N-α-acetylarginine (NAArg). Arginine levels are the mean of the values obtained from the two ARG1-D patients treated with 0.015 mg/kg ("●") and 0.03 mg/kg pegzilarginase ("□"), using a validated (GLP) assay. ArgA, GVA, and NAArg levels were obtained using a non-GLP assay using pooled samples from the same two ARG1-D patients treated with 0.015 mg/kg and 0.03 mg/kg pegzilarginase. The "*" indicates the normal range in human serum as described in Lüneburg, N. et al., (2011), for arginine, or Marescau et al., (1990) for guanidino compounds.
Figure 3B:
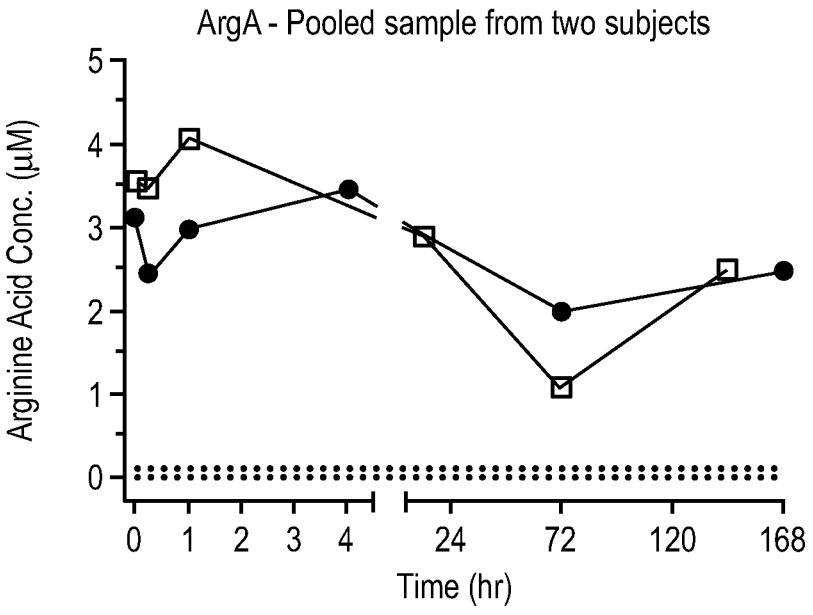
Figure 3C:
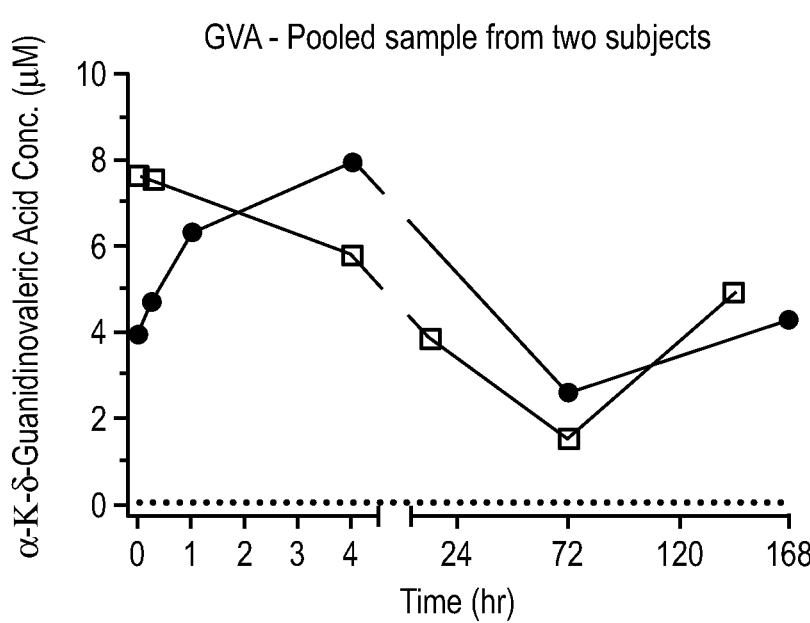
Figure 3D:
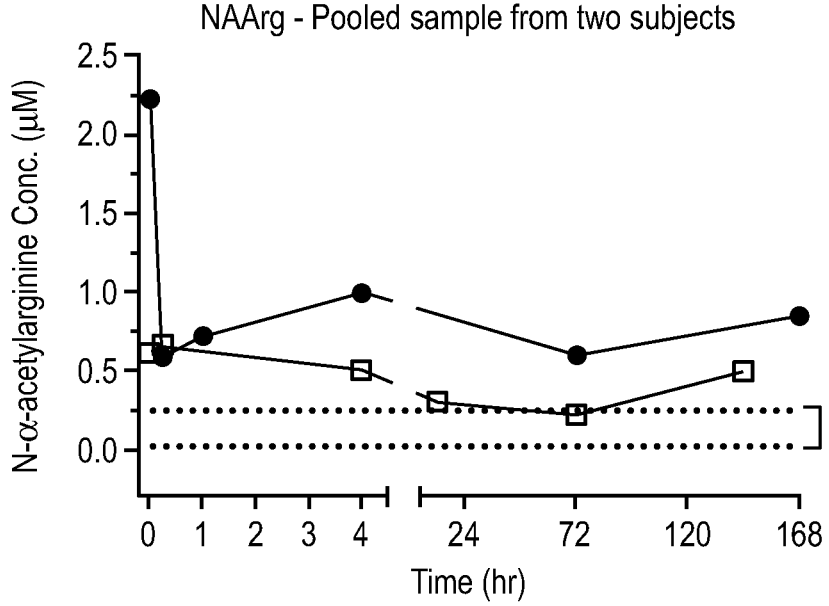

For the data presented herein, not only were the ArgA, GVA, and NAArg levels assayed, but also the homoarginine (HArg) level. HArg levels were examined, because HArg was significantly elevated in the serum of ARG1-D patients in the Marescau et al., (1990) study. HArg levels did not appear to be modulated in the ARG1-D patients treated with pegzilarginase (FIG. 2). This result is consistent with the data reported by Marescau et al. (1990) in that serum HArg levels did not decrease in patients maintained on a protein restricted diet. Additional conditions that can be assessed with patient treatment are improved muscle strength, ambulatory ability of a patient (i.e., ability to run, walk, ride a bike, climb stairs without support), improved cognitive ability (for example WISC testing improvement), or changes in adaptive behavior (for example with ABAS or VABS testing).

GC data was also generated from pooled plasma samples obtained from the two (2) adult patients treated with a lower dose of pegzilarginase, 0.015 mg/kg patient weight. A reduction in the plasma arginine concentration was observed at the lower pegzilarginase dosing; however, this decrease was not as pronounced as the decrease in plasma arginine observed at the 0.03 mg/kg dosage.

Given the findings on these two patients provided above, it was concluded that pegzilarginase administered at a dosage of 0.04 mg/kg intravenously to a patiently weekly was well tolerated in adult ARG1-D patients. The patients had marked reductions of GCs that paralleled arginine level reductions. The effects on arginine and GC levels appear based on these two adult patients to be more scientifically substantial than the effects achieved historically with strict dietary arginine restrictions. One ARG1-D patient in the study was successfully dosed at 0.2 mg/kg. Solid tumor maximum tolerated dose (MTD) was established at 0.33 mg/kg and doses up to 0.48 mg/kg.

Of course, a patient with high arginine levels (e.g., 600-800 µM arginine) may be treated with a higher dose than 0.50 mg/kg of pegzilarginase. A patient with high arginine levels may require administration of the arginase in a range of 0.005 to 1.00 mg/kg subject body weight. A dosing range of 0.005 mg/kg to 0.50 mg/kg and/or 0.005 to 0.20 mg/kg subject body weight are also contemplated.

Bioavailability of a drug can be determined by measuring the amount of the drug in the blood over a specified time period from an IV and/or subcutaneous injection. For purposes of the calculation, 100% of the drug administered intravenously is assumed to enter the blood stream, while not all of the drug administered subcutaneously enters the blood from the subcutaneous space. Bioavailability can be determined by dividing the subcutaneous total over the IV total. Bioavailability of pegzilarginase administered subcutaneously was determined to be approximately 60% of the IV administration based upon a comparison of intravenous and subcutaneous administration in cynomolgus monkey. A patient with high levels of arginine, therefore, may be successfully treated with as much as 1.5 mg/kg of an arginase. Based upon the bioavailability data, a dosing range for subcutaneous administration of pegzilarginase can be for example 0.01 to about 1.5 mg/kg subject body weight; 0.015 mg/kg to 0.75 mg/kg; and/or 0.015 mg/kg to about 0.30 mg/kg subject body weight are used.

Figure 4A:
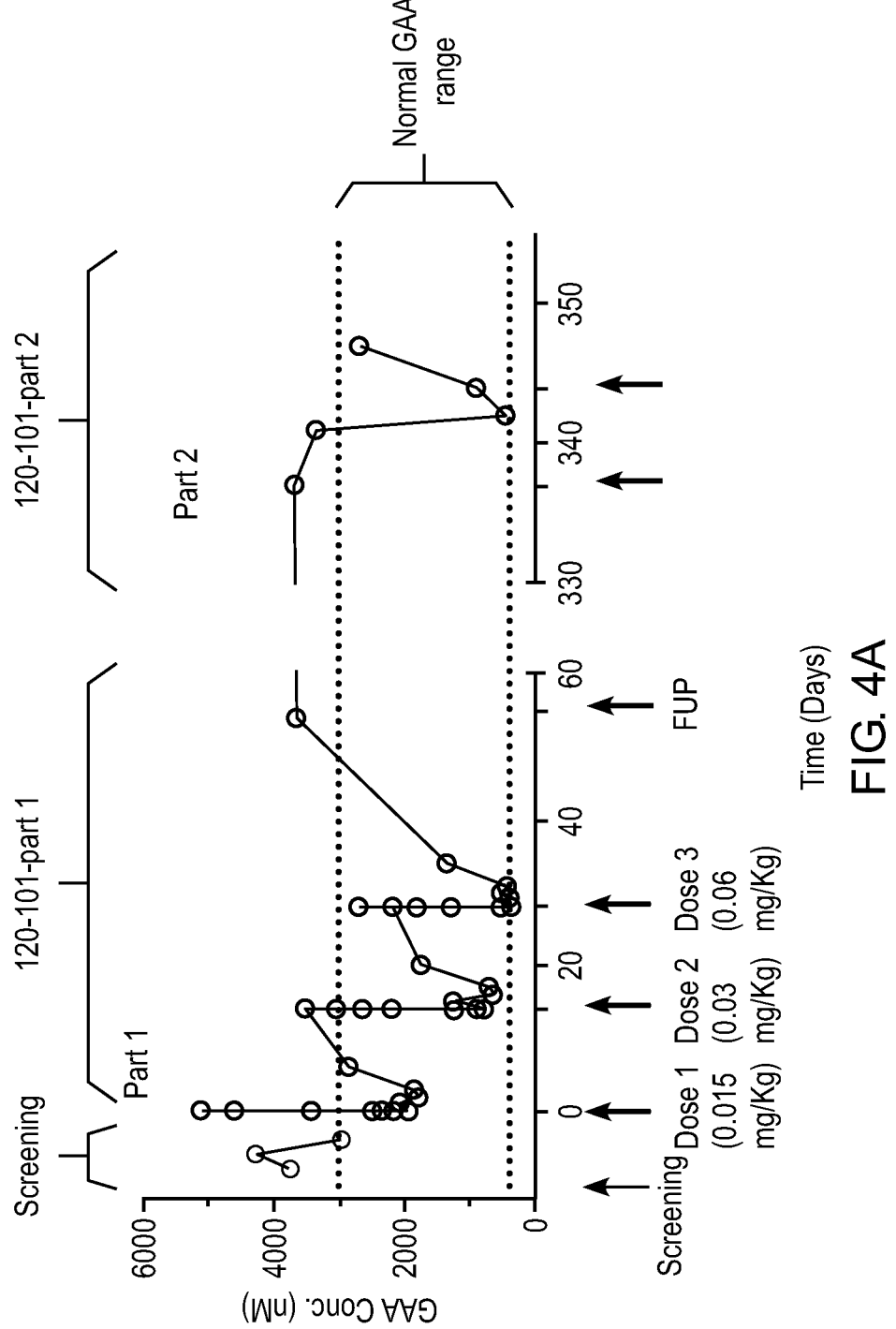
FIGS. 4A and 4B show data for GAA in two patients, patient 120-101 (FIG. 4A) and patient 120-102 (FIG. 4B), before (e.g., at screening) and after treatment with pegzilarginase. In both cases data are shown for GAA levels at the time of screening, and during dosing for parts 1 and 2. "FUP" indicates follow-up. A normal range of GAA is 0.40 µmol/L to 3.00 µmol/L. See, e.g., Marescau et al., (1990).
Figure 4B:
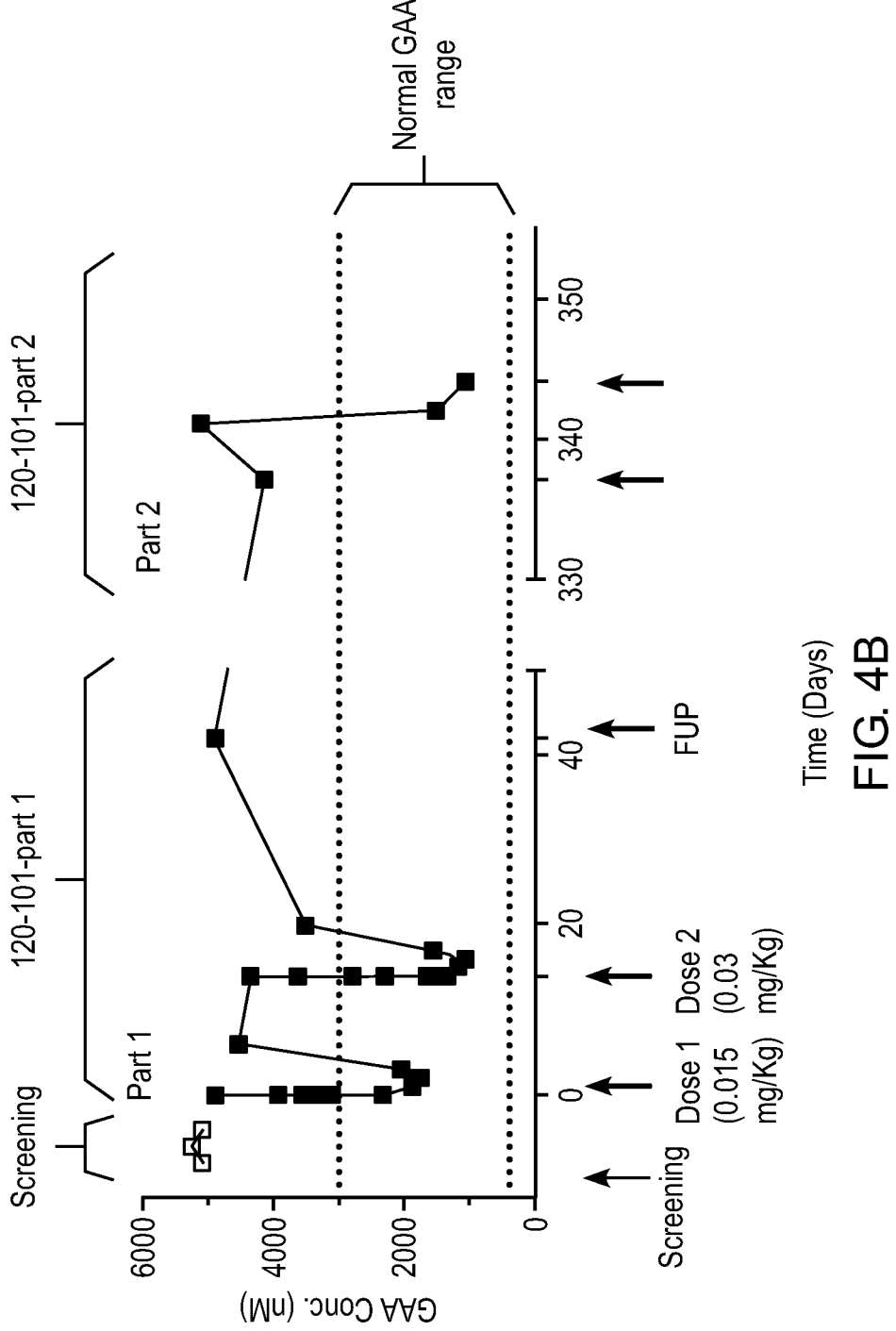

FIGS. 4A and 4B show data for GAA in two patients, patient 120-101 (FIG. 4A) and patient 120-102 (FIG. 4B), before (e.g., at screening) and after treatment with pegzilarginase. In both cases data are shown for GAA levels at the time of screening, and during dosing for parts 1 and 2. In both patients, GAA was reduced after administration of the 0.015 mg/kg subject body weight and a greater effect was observed at higher doses. Notably, a rapid decrease in GAA was observed shortly after administration with pegzilarginase. Furthermore, the initial treatment brought both patients into the normal range of plasma levels of GAA within a 24 hour period after administration. For example, in FIG. 4B, on day 14, the patient's GAA level is 4,350 nM, which is reduced within 24 hours after administration of the arginase to as low as 1,350 nM. Thus, treatment with the arginase can rapidly clear a toxic metabolite such as GAA or GVA and is useful as an acute treatment. Pegzilarginase clears the indicated toxic metabolites at a far faster rate than an arginine-reduced diet alone.

Patient Characteristics and Safety

Baseline assessments were performed for the patients in the phase 1/2 study. Baseline assessments, provided in the table below, showed a substantial disease burden for patients in the study. Patients were on a protein restricted diet.

For Berg Balance, a deficit balance is defined as medium or high risk of fall (i.e., score≤40). For 6MWT, a deficit is defined as below the age-adjusted range for normal individuals in Geiger et al., "Six-minute walk test in children and adolescents," *J. Pediatr.,* 2007 April; 150(4):395-399, and Enright et al., "Reference equations for the six-minute walk in healthy adults,"*Am. J. Respir. Crit. Care Med,* 1998 November; 158(5 Pt 1):1384-1387. For GMFM Part E, a deficit is defined as <68 based on the minimal clinically important difference (MCID) in Oeffinger et al., "Outcome tools used for ambulatory children with cerebral palsy: responsiveness and minimum clinically important differences," *Dev. Med. Child Neurol.,* 2008 50(12): 918-925. If multiple baseline laboratory assessments were available, the assessment immediately prior to dosing is reported. For PROMIS, a deficit baseline is defined as a T-Score<40.

TABLE 7

| Baseline assessments performed for the patients in the phase 1/2 study. | | |
|---|---|---|
| Characteristic/ Assessment (N = 12) | Median (range) or n (%) | Deficit baseline (%) |
| Disease Characteristics and Medical History | | |
| Age (years) | 16.5 (5-31) | |
| Female | 8 (67%) | |
| History of Spasticity (≥moderate) | 7 (58%) | |
| History of seizures | 7 (58%) | |
| History of Hyperammonemia | 6 (50%) | |
| Developmental Delay | 8 (67%) | |
| Ammonia Scavenger | 11 (92%) | |
| Baseline Disease Manifestations | | |
| Arginine (μmol/L) | 397 (203 to 531) | 100% |
| Baseline alanine transaminase (ALT) (U/L) | 37.5 (21 to 171) | 58% |
| Baseline Ammonia (μmol/L) | 37 (9 to 77) | 50% |
| Height Centile (based upon Centers for Disease Control and Prevention growth chrarts) | 4.4% (<0.1% to 22.9%) | 92% |
| 6MWT (m) | 266.5 (102 to 602) | 92% |
| Berg Balance (Score 0-56) | 47 (11 to 56) | 42% |
| GMFM Part E (Score 0-72) | 48.5 (12 to 72) | 67% |
| PROMIS physical function domain | 38 (28.3 to 57.1) | 58% |

Most-treatment-related adverse events ("AEs") were mild as shown in the table below. Treatment-related AEs that occurred in ≥2 patients were hypersensitivity (n=3, all moderate), pruritus (n=3, all mild), and dry skin (n=2, both mild). In sum, over 130 infusions were administered among all of the patients in the study. Four moderate hypersensitivity reactions in three patients (2 considered serious adverse event (SAE)) were observed. These AEs were managed with infusion rate adjustments and the administration of antihistamines, and in some cases corticosteroids. There was one SAE of hyperammonemia assessed as not related to treatment with pegzilarginase.

TABLE 8

| Adverse events. | | |
|---|---|---|
| Patients With | Part 1 (n = 12) | Part 2 (n = 4) |
| Any Related AE | 6 (50%) | 3 (75%) |
| Any SAE | 3 (25%) | 0 |
| Any Related SAE | 2 (17%) | 0 |

Pegzilarginase ADA effects were studied. A bridging assay that employs the Meso Scale Discovery electro-chemiluminescent method was validated to detect antibodies to AEB1102 (Co-Arg1-PEG) in rat, monkey, and human serum. The method used biotinylated AEB1102 (B-AEB1102 or B-Co-ArgI-PEG) to capture ADA and ruthenium labeled AEB1102 (Ru-AEB1102 or Ru-Co-ArgI-PEG) to detect the antibodies.

During validation, a Master Mix (MM) of B-Co-ArgI-PEG and Ru-Co-ArgI-PEG was prepared in assay buffer to final concentrations of 1.0 μg/mL B-AEB1102 and 1.0 μg/mL Ru-AEB1102. Diluted samples and controls were added to Master Mix in the wells of a streptavidin-coated plate. Subsequent to incubation and washing, 150 μL, of 2× Read Buffer T (from Meso Scale Discovery) was added to each well. The samples were read on the Sector Imager 6000. This method was used for screening, titering, and confirmation, noting that the confirmatory assays were pre-incubated with 150 μg/mL AEB1102 (drug). High, mid, low concentrations of the positive control and negative controls were included in each run. Cut points, screening, and confirmation were statistically assigned to afford approximately a 5% and 1% false positive rate, respectively. The positive control was the anti-Co-ArgI-PEG affinity purified polyclonal antibody and the Negative Control (NC) was aliquoted pooled normal rat, cynomolgus monkey, or human serum. The positive and non-specific binding (NSB) controls were used to monitor assay performance.

A direct binding assay was validated to detect antibodies against PEG, to allow detection of anti-PEG antibodies that may be pre-existing or treatment emergent after administration with AEB1102.

Wells of a Starwell C8 Maxisorp (a 96-well format plate) were coated with 100 μL of 2 μg/mL mono-pegylated bovine serum albumin (BSA) (BSA-mPEG) 5 kDa (Life Diagnostics), or 500 ng/mL Human IgG (Jackson ImmunoResearch Laboratories), or 500 ng/mL human IgM (Jackson ImmunoResearch Laboratories) in carbonate coating buffer (Bio-World). Controls and samples diluted to the minimum required dilution (MRD) of 50-fold in Diluent Buffer were added to the plate in duplicate (100 μL/well). Diluent buffer comprises 4% bovine gamma globulin in 1× phosphate buffered saline (PBS). 100 μL of detection antibodies were added to the appropriate wells. The mouse anti-PEG antibody (Jackson ImmunoResearch Laboratories) was detected using a goat anti-Mouse IgG-Fc-HRP (Jackson ImmunoResearch Laboratories) that was diluted 1:5,000, and anti-Human antibodies were detected using rabbit anti-Human IgG/A/M (Jackson ImmunoResearch Laboratories) that was diluted 1:30,000 in diluent buffer and added to the appropriate wells. Followed by the addition of 100 μL per well of 3,3',5,5'-tetramethylbenzidine (TMB) substrate, the reaction was stopped after approximately 10 to 20 minutes by adding 100 μL of stop solution per well. The plate(s) were read on a Synergy 2 plate reader at 450 (detection) and 620 (background). Cut points, screening, and confirmation were statistically assigned to afford approximately a 5 and 1% false positive rate, respectively. This method was used for screening, titering, and confirmation. Samples to be titered were subjected to a minimum of seven 2-fold serial dilutions in a negative pooled human serum.

Transient, low-titer anti-PEG ADAs (anti-drug antibodies) were detected in the Part 1 portion of the patient study (see table below). There was no detectable ADA detected in 6/7 patients at the start of repeat dosing. Tolerization to the pegzilarginase was unexpectedly rapid as noted in Table 9 below.

TABLE 9

| ADA assessment for pegzilarginase and PEG. | | | | |
|---|---|---|---|---|
| ADA Type | Part 1 Prior to Treatment (n = 10) | Part 1 Treatment-Emergent (n = 10) | ADA At Start of Part 2 (n = 7*) | Titer Range |
| Anti-PEG | 10% | 40% | 14% | 50-400 |
| Anti-Pegzilarginase | 10% | 30% | 0 | 10-160 |

*One patient with anti-PEG ADA prior to treatment had declining titer during Part 1 and no detectable ADA at the final Part 1 dose. However, this patient did not continue in Part 2 of the study for reasons unrelated to the study; this patient is not included in the n = 7.

Figure 5A:
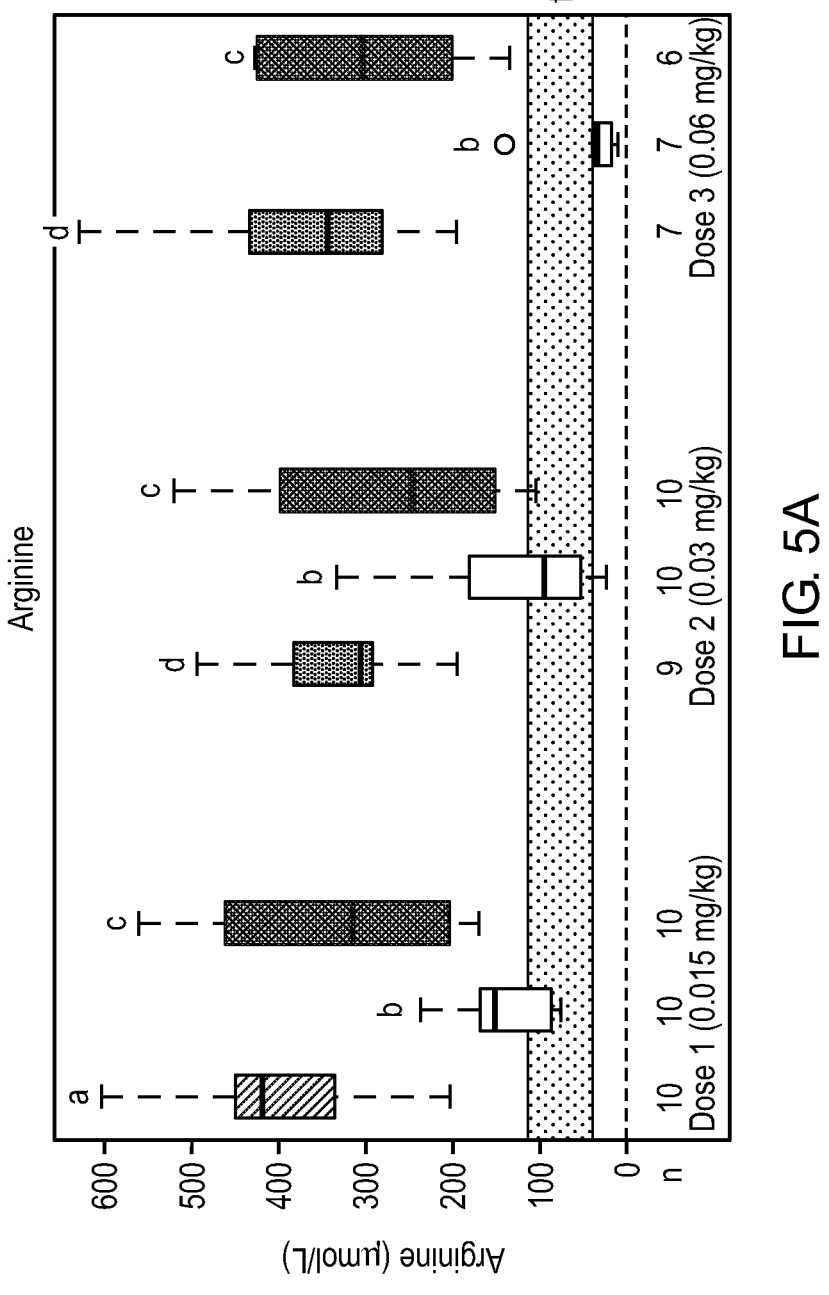
FIG. 5A. The effect of arginase treatment on the plasma levels of arginine and GCs was examined in Part 1 of the clinical study, which utilizes a single dose (NAA refers to NAArg).
Figure 5B:
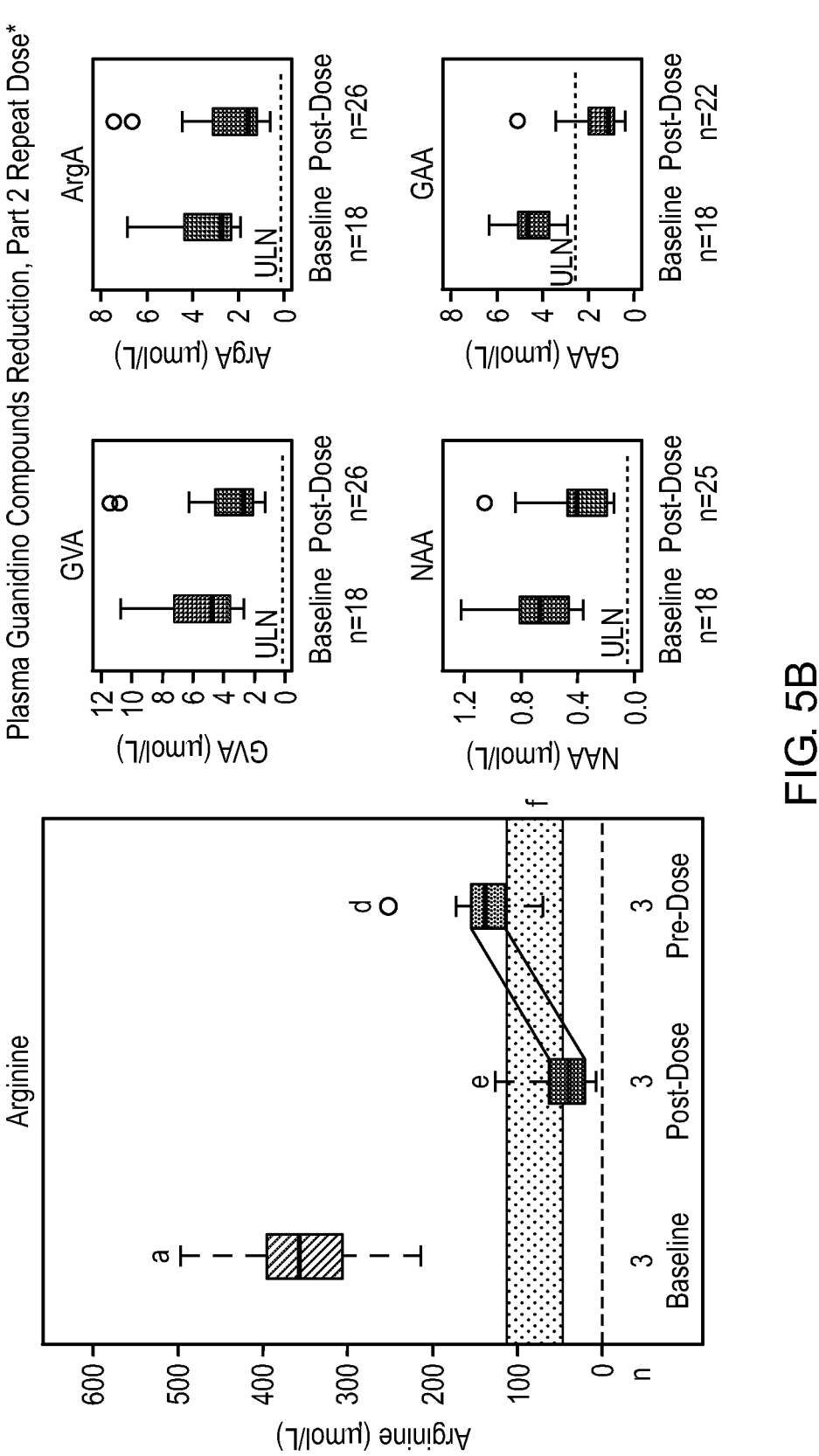
FIG. 5B depicts the effect of arginase treatment on the plasma level of arginine and GCs was examined in Part 2 of the clinical study, which includes a repeat dose. The data shown for Part 2 includes patients with all eight (8) doses administered according to the clinical protocol. For both FIGS. 5A and 5B, "a" indicates the baseline arginine level in patients, "b" indicates the post-dose nadir, "c", indicates the levels at 7 days post-dose, "d" indicates a pre-dose level of arginine, "e" indicates all post-dose, "f" indicates the normal range of plasma level for arginine in a healthy patient, 40 µmol/L to 115 µmol/L as described in Lüneburg, N. et al., (2011), and "n" represents the number of patients. Post-dose nadir is the lowest value following a Part 1 dose; "all post-dose" in Part 2 includes all post-dose values except the value immediately prior to the next dose.

FIGS. 5A and 5B show the effects of arginine and GCs. GAA was elevated in ARG1-D patients. GAA levels in these patients were lowered by treatment with pegzilarginase. The repeat dose graphs shown in FIG. 5B include patients who received all 8 doses in Part 2. The upper limit of normal (ULN) for GCs is based upon a study of GCs in healthy adults. Pegzilarginase is highly effective at lowering arginine levels into the normal range in a single dose and in the repeat dosing (FIG. 5B). GAA, which is elevated in ARG1-D patients, is also lowered by treatment with pegzilarginase. A time-dependent decrease in the concentration of GVA, ArgA, GAA, and NAA was observed after the IV QW (weekly) treatment with pegzilarginase. The decreases in GVA, ArgA, GAA, and NAA levels occurred within 24 hours of the first infusion, and reduction from baseline levels were maintained throughout the 8 weeks of dosing. Serum pegzilarginase levels were determined at multiple time points around dose 1 and dose 8.

Figure 6:
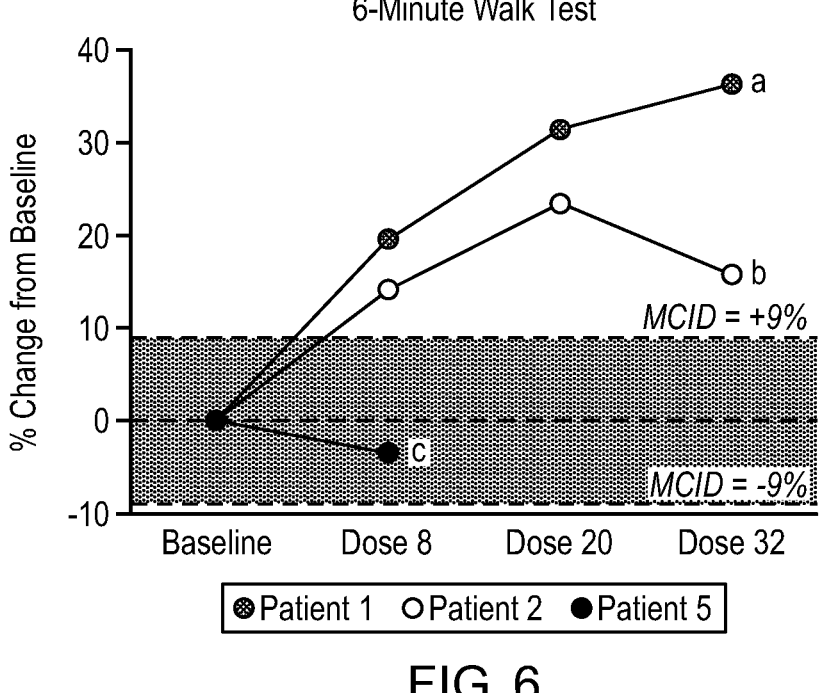
FIG. 6. The results of the 6-minute walk test for three patients, patients 1 ("a"), 2 ("b"), and 5 ("c"), at baseline, at dose 8, at dose 20, and at dose 32 (data not available for patient 5 ("c") at doses 20 and 32) are shown. Doses 8, 20, and 32 are from the start of repeat dose.

FIG. 6 provides that results of the 6-minute walk test for three patients (data not available for patient 5 ("c") at doses 20 and 32). Neuromotor results are provided in the table below. Dose 8, 20, and 32 are measured from the start of repeat dose (second dose). PROMIS is specifically the Physical Function Domain of PROMIS. Data in the table below for 6MWT (6 minute walk test), BBS (Berg Balance Scale), GMFM Part E, and PROMIS are presented as raw values for the baseline and change from baseline for other time points. The MCID for the 6MWT is defined from an analysis of Schrover et al., "Minimal clinically important difference for the 6-min walk test: literature review and application to Morquio A syndrome," *Orphanet. J. Rare Dis.*, 2017 Apr. 26; 12(1): 78; for BBS, the MCID is defined from an analysis of Downs et al., "The Berg Balance Scale," *J. Physiother.*, 2015 January; 61(1): 46; for GMFM, the MCID is defined from an analysis of Oeffinger et al., 2008, and for PROMIS, the MCID is based upon Physical Function having 0.5 standard deviations, or 5 points on the T-Score. The table below and FIG. 6 demonstrate improved neuromotor function for patients subsequent to administration with pegzilarginase. Neuromotor function may refer to muscle or nerve functions, and can be clinically assessed in a patient using, for example, PROMIS, 6MWT, BBS, and GMFM. Examples of neuromotor function include without limitation climbing steps, walking, spasticity, and alertness. For example, an afflicted patient may walk on tip toes instead of normally (heel to toe). Improved neuromotor function may refer to such a patient's ability to walk better or walking normally instead of on tip toes. Improved neuromotor function may refer to enhanced mobility such as no longer requiring the use of or requiring less use of a walking aid (e.g., a "walker" or cane). Improved neuromotor function may refer to improved posture, and/or improved communication/socialization.

TABLE 10

| Neuromotor function assessment. | | | | | | |
|---|---|---|---|---|---|---|
| Patient Age (years) | Physician/Assessor Observations | Time point | 6MWT (m) | BBS MCID +7 | GMFM Part E MCID varies | PROMIS T-Score MCID +5 |
| #1 25 | Improved step quality and confidence while walking Less resting spasticity | Baseline Dose 8 Dose 20 Dose 32 | 102 122 134 139 | 17/56 30 35 28 | 29/72 32 35 36 | 35.6 33.3 |
| | | | | | MCID: +1.8 | |
| #2 24 | No meaningful observations documented to date. | Baseline Dose 8 Dose 20 Dose 32 | 261 298 322 302 | 54/56 54 53 53 | 63/72 66 64 64 MCID: +4.0 | 40.4 48 |
| #5 19 | Improve posture and increased confidence while walking Patient noted to be more animated and alert | Baseline | 174 | 31/56 | 27/72 | 36.7 |
| | | Dose 8 | 168 | 30 | 29 MCID: +2.8 | 41.8 |

GAA has been linked to seizures in GAMT (guanidinoacetate methyltransferase) Deficiency patients (Stockler-Ipsiroglu et al., "Guanidinoacetate methyltransferase (GAMT) deficiency: outcomes in 48 individuals and recommendations for diagnosis, treatment and monitoring," *Mol. Genet. Metab.*, 2014; 111(1): 16-25). The results demonstrate that treatment with pegzilarginase lowered the GAA level in patients as well as reducing the plasma arginine and related GCs. The levels of one or more guanidino compounds such as GAA (see, e.g., FIG. 5B) is reduced or cleared within 24 to 48 hours post-administration of the arginase. The arginase, therefore, is useful as an acute treatment to reduce or clear toxic metabolites in a patient. Clinical improvements were observed with repeat dose administration of pegzilarginase after 8 weeks. Pegzilarginase was generally well tolerated by the patients. Most related AEs were mild and manageable with standard measures.

Treatment with pegzilarginase unexpectedly, and rapidly reduced symptoms of hyperargininemia in the ARG1-D patients. These improvements manifested at a biochemical level. Plasma levels of one or more of arginine and guanidino compounds can be reduced to a normal level based upon an initial and/or repeat administration of an arginase. In addition, administration of an arginase improved adaptive behavior and/or neuromotor functions of patients with ARG1-D. All patients in the study had and were receiving standard or conventional treatments for hyperargininemia during study. Such standard or conventional treatments involve diet restrictions to limit intake of protein that can increase arginine levels, and the use of nitrogen-scavenging drugs. Despite these standard treatments, all patients still had high arginine levels. Treatment with an arginase, rapidly and sustainably reduces plasma levels of one or more of arginine and other guanidino compounds. The effect of treatment with the arginase (e.g., pegzilarginase) was unexpectedly rapid, occurring within 24-48 hours post-administration. In contrast, a standard or conventional treatment for hyperargininemia may not show any improvement for two years (Marescau et al., 1990; Marescau et al., "The pathobiochemistry of uremia and hyperargininemia further demonstrates a metabolic relationship between urea and guanidinosuccinic acid," 1992 41(9): 1021-1024). Furthermore, patients treated with pegzilarginase can have a more liberal diet due to the reduction in arginine, and could thereby have more protein.

Figure 7:
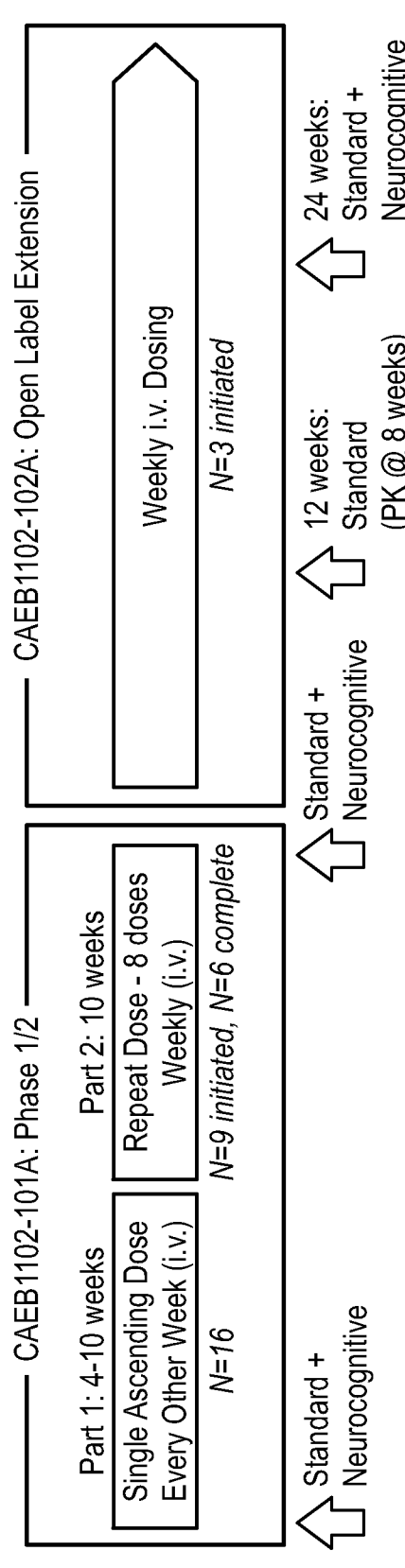
FIG. 7. Provides an overview of the phase 1/2 study and open-label extension.

Phase 2 Clinical Data Showing Improvements in ARG1-D Related Disease Manifestations Following Plasma Arginine Reductions with Arginine-Depleting Agent Continuing the open label phase 1/2 study from above with Parts 1 and 2, an open label extension was pursued. As illustrated in FIG. 7, phase 1/2 had 16 patients in Part 1 who received a single ascending dose of pegzilarginase, as described above, every other week intravenously for 4 to 10 weeks. In Part 2, a repeat dose (8 doses weekly) of pegzilarginase was administered intravenously for 10 weeks, as described earlier. There were nine patients who initiated part 2 and 6 patients who completed the repeat dose. In the open label extension, intravenous administration of pegzilarginase was initiated to three patients.

The table below shows the patient characteristics and indicates the disease burden of the patients in the study and open label extension. The median plasma arginine was based on computing the mean of all plasma arginine values prior to the first dose for each patient and determining the median of these values. The table shows that all 16 patients had elevated baseline plasma arginine. Seven of ten patients had deficits in both mobility and adaptive behavior. Median plasma arginine was based on the mean of all plasma arginine values prior to first dose for each patient. For other biochemical parameters, the assessment immediately prior to dosing was used. For laboratory assessments, abnormal is defined as being outside the reference range. For height centile, deficit was defined as ≤10% of normal as provided by CDC. For 6MWT, Berg Balance, GMFM Part E, and PROMIS are applied as described earlier. For Adaptive Behavior Assessment System, Third Edition (ABAS), deficit is defined as standard score<85 on Practical, Social, Conceptual, or Composite. MCID (see FIG. 9) for 6MWT was defined as a 9% change from baseline; for GMFM Part E, as a change of 1.8 to 4.0 points, depending on individual patient Gross Motor Function Classification System level; for BBS, as a 7 point change; for ABAS, as a change in General Adaptive Composite (GAC) Standard Score of 7.5 points; and for PROMIS, as a change of 5 points.

TABLE 11

| Baseline assessments performed for the patients in the phase 1/2 study. | | |
| --- | --- | --- |
| Characteristic/Assessment (N = 16) | Median (range) or n (%) | Deficit baseline (%) |
| Disease Characteristics and Medical History | | |
| Median Age (range) | 15 years (5-31) | |
| Female | 11 (69%) | |
| History of Spasticity (≥moderate) | 9 (56%) | |
| History of seizures | 7 (44%) | |
| History of Hyperammonemia | 7 (44%) | |
| Developmental Delay | 9 (56%) | |
| Ammonia Scavenger | 15 (94%) | |
| BASELINE ASSESSMENTS | | |
| Laboratory | | |
| Arginine (μmol/L, before first-dose assessment) | 389 (238 to 566) | 100% |
| Alanine transaminase (ALT) (U/L) | 34 (15 to 171) | 44% |
| Ammonia (μmol/L) | 38 (9 to 77) | 44% |
| Mobility | | |
| 6MWT (m), N = 15 | 349 (102 to 602) | 87% |
| PROMIS Physical Function/Mobility, N = 14 | 38 (28.3 to 57.1) | 57% |
| GMFM Part E (Score 0-72) | 65.5 (5 to 72) | 50% |
| Berg Balance (Score 0-56) | 52.5 (7 to 56) | 38% |
| Adaptive Behavior | | |
| ABAS, N = 10 | 79.5 (49 to 90) | 80% |
| GROWTH | | |
| Height (CDC Centile) | 4.8% (<0.1% to 56%) | 88% |

Figure 8:
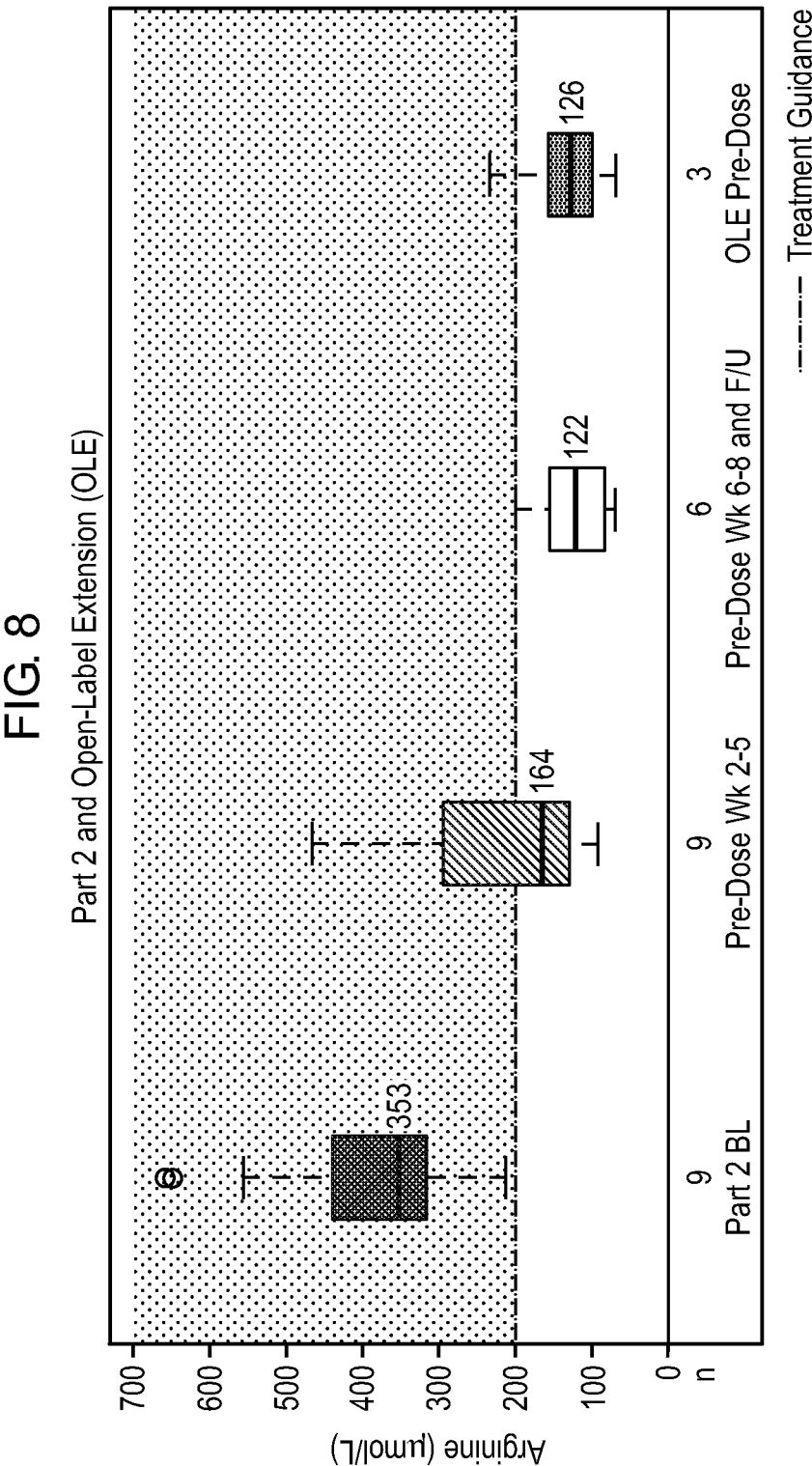
FIG. 8. A time-dependent improvement in plasma arginine with repeat dosing with pegzilarginase for Part 2 and open-label extension patients. "BL" is baseline; "F/U" is follow-up; "OLE" is open-label extension, and "n" is the number of patients at each time point. It is desirable to maintain arginine at ≤200 µmol/L in patient plasma. 100% (5/5) of patients who completed Part 2 have achieved consistent levels of reduced arginine that are below the recommended guideline. Arginine reduction was accompanied by sustained decreases in plasma GCs (GVA, ArgA, NAA, and GAA).

FIG. 8 shows a time-dependent improvement in plasma arginine with repeat dosing for Part 2 and open-label extension patients. BL is baseline; F/U is follow-up; and n is the number of patients at each time point. The median arginine levels for all patients are indicated for each time point. According to treatment guidelines described in Haberle et al., "Suggested guidelines for the diagnosis and management of urea cycle disorders," Orphanet. J. Rare Dis., 2012 7: 32, it is desirable to maintain plasma arginine levels at ≤200 μmol/L. FIG. 8 shows that 100% (6/6) of patients who completed Part 2 have achieved consistent levels of reduced arginine that are below the recommended guideline. A reduction in the plasma levels of arginine reduction was accompanied by marked and sustained decreases in plasma levels of GCs (GVA, ArgA, NAA, GAA).

Figure 9:
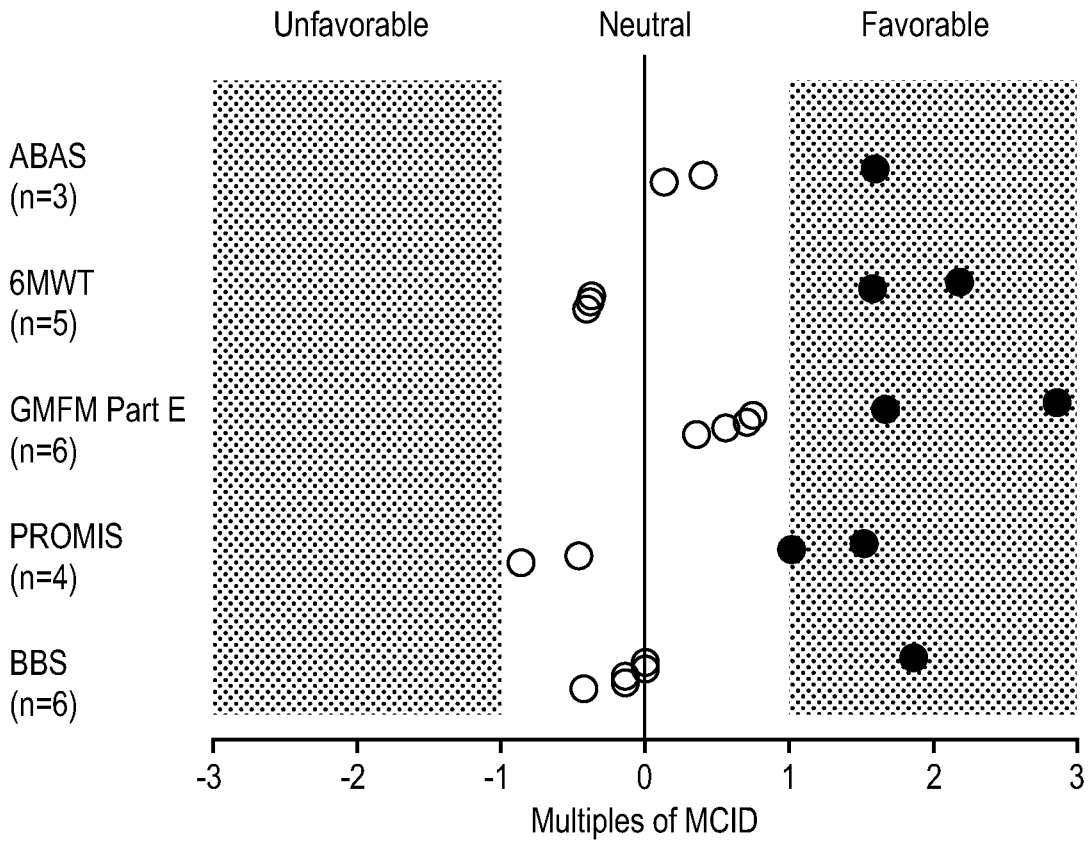
FIG. 9. Treatment with pegzilarginase improved clinical outcomes from the baseline after only 8 repeat doses. Each point in FIG. 9 represents one assessment for one patient. Favorable assessments are indicated with a solid circle "●", while neutral assessments are indicated with an unfilled circle "○".

Treatment with pegzilarginase also improved clinical outcomes from the baseline after 8 repeat doses, as illustrated in FIG. 9. Each point in FIG. 9 represents one assessment for one patient. Favorable assessments are indicated with a solid circle "●", while neutral assessments are indicated with an unfilled circle, "○". 67% (4/6) patients displayed improvement beyond MCID in tests for mobility and/or adaptive behavior after only 8 weeks of repeat dosing with pegzilarginase. The standards for these tests is described earlier for 6MWT, Berg Balance Scale, GMFM Part E, PROMIS, and ABAS. 33% of assessments favorably exceeded MCID, while none unfavorably exceeded MCID. ⅓ of ABAS assessments favorably exceeded MCID with ⅔ trending toward improvement at 8 weeks.

TABLE 12

| | Summarizes observations from some of the patients in the study by assessors. | |
|---|---|---|
| Patient | Observations from site/assessors | Time point |
| 1 | Improved step quality and confidence while walking<br>Less resting spasticity than baseline<br>Able to stand without support for 1 minute<br>Walks a few steps with support<br>Improved ability to squat and ability to pick up an object up from the floor | Part 2, dose 8 |
| 2 | Appeared more comfortable<br>More relaxed demeanor and willingness to talk<br>Standing on 1 leg is typically very difficult, able to accomplish on first try | Part 2 F/U |
| 5 | Improved posture and increased confidence while walking<br>Noted to be more animated and alert<br>Asking more complex questions | Part 1, dose 3 |
| 6 | Able to converse much better<br>Communication improved<br>Can walk properly, not on tip toes | Part 1, dose 1 (first two observations);<br>Part 1, dose 4 (third observation) |
| 7 | Increased appetite and activity<br>Walking around ½ mile 3-4 × weekly, taking the dog for a walk<br>Muscle development noted in calves<br>More talkative, goes to store<br>Walking ability has been improved<br>Seems more happy | Part 1, F/U |
| 9 | Leg cramps resolved<br>Walking with more speed and less labored | Part 1, dose 3 |

Pegzilarginase administration generally resulted in mild AEs, if any. 180 infusions of pegzilarginase were administered across all patients. Low-titer, treatment emergent ADAs were detected in 6/16 patients in Part 1. All patients in Part 2 had undetectable ADA levels by the fifth dose. Treatment-related AEs≥2 patients of at least moderate severity included hypersensitivity (4 events in 3 patients; 3 considered by investigators as serious adverse events (SAEs)), which was managed with infusion rate adjustment and medication such as administration of antihistamines, and in some cases corticosteroids.

Figure 10:
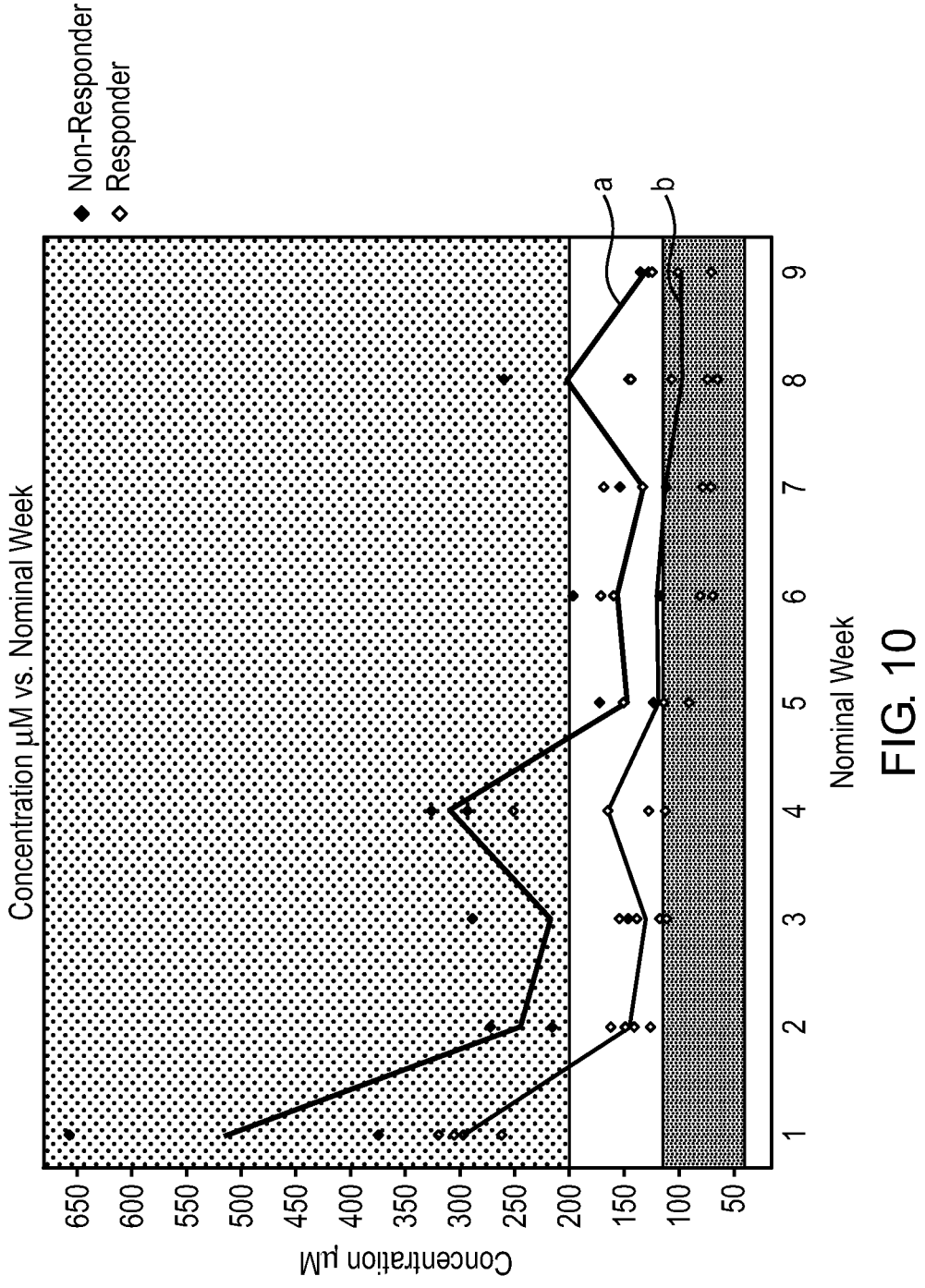
FIG. 10 shows arginine concentration over a nine week period for patients that responded to pegzilarginase treatment (responder) and those who did not respond to pegzilarginase treatment (non-responder) based upon the patient's MCID improvement. The range for arginine in plasma above medical guidelines is ≥200 µmol/L; the normal range for a human for arginine is 40 µmol/L to 115 µmol/L as described in Lüneburg, N. et al., (2011). MCID is determined as described below. A responder" can be an individual having >1 MCID; a non-responder can be an individual having <1 MCID. Non-responder data points are indicated by a closed diamond; responder data points are indicated with an open diamond. The average of the non-responder data points is

FIG. 10 shows an analysis of the mean arginine value by clinical response was undertaken for the patients participating in Part 2. The mean arginine levels of patients were found to be lower for patients who had a clinical response of >1 MCID improvement in the Neuromotor or Adaptive Behavior assessments (n=4) than patients whose improvements were <1 MCID improvement in the Neuromotor or Adaptive Behavior assessments (n=2).

In conclusion, the progressive nature of this disease, despite standardized disease management approaches utilizing severe dietary protein restriction and use of ammonia scavengers to only address disease symptoms, highlights the significant unmet medical need for pharmacological therapy that will lower arginine levels beyond those achievable with current standard disease management and thus provide the potential to slow or halt the progression of neuromotor, neurocognitive, and/or adaptive behavior deterioration observed in ARG1-D patients. Pegzilarginase, an engineered human arginase 1, has produced direct evidence of marked and sustained reductions in plasma arginine and related GC levels in patients with ARG1-D accompanied by improvements in neuromotor function and/or adaptive behavior in some patients.

Improvements from the administration of pegzilarginase for ARG1-D patients that were observed in the phase 1/2 arm of the study described earlier persisted in the open-label extension. Pegzilarginase was highly effective in sustainably lowering elevated plasma arginine, which is believed to underlie the pathology of ARG1-D symptoms. Plasma arginine reductions were accompanied by improvements in mobility and adaptive behavior after only 8 weeks of repeat dosing. Pegzilarginase was well tolerated by patients. Most treatment-related AEs were mild; hypersensitivity reactions were manageable with standard measures and all patients continued study treatment. Comprehensive baseline profiling of patients with ARG1-D demonstrated quantifiable deficits in mobility and/or adaptive behavior in 94% (15/16) patients.

Method for Analysis of α-K-δ-GVA, (R,S)-ArgA, Homoarginine HCl, and Na Acetyl-L-Arginine in $K_2$EDTA Human Plasma by LC-MS/MS.

| Analyte/Metabolite Names: | α-K-δ-GVA (GVA) |
|---|---|
| | (R,S)-ArgA (ArgA) |
| | Homoarginine HCl (HArg) |
| | Na Acetyl-L-Arginine (NAArg) |
| | Guanidinoacetic acid (GAA) |
| Internal Standard Names: | a-K-d-GVA-$^{13}C_6$ HCl (GVA-$^{13}C_6$) |
| | $^{13}C_6$-(R,S)-ArgA (ArgA-$^{13}C_6$) |
| | L-Homoarginine-d4 Dihydrochloride (HArg-d4) |
| | Na Acetyl-L-Arginine-$^{13}C_6$ (NAArg-$^{13}C_6$) |
| | Guanidinoacetic-[$^{13}C_2$]acid (GAA-[$^{13}C_2$]) |

-continued

| Species/Matrix: | Treated Human Plasma |
|---|---|
| Anticoagulant : | K₂EDTA |
| Sample Volume: | 0.050 mL |
| Curve Ranges: | 25.0 to 5000 nM (GVA, ArgA) |
| | 200 to 40,000 nM (HArg) |
| | 50.0 to 10,000 (NAArg) |
| | 3,000 to 100,000 (GAA) |
| Regression Type: | GVA: Linear, $1/x^2$ |
| | ArgA: Linear, $1/x^2$ |
| | NAArg: Quad, $1/x^2$ |
| | GAA: Quad, $1/x^2$ |
| Response: Peak Area Ratio: | GVA/GVA-$^{13}$C$_6$ |
| | ArgA/ ArgA-$^{13}$C$_6$ |
| | HArg/ HArg-d4 |
| | NAArg/ NAArg-$^{13}$C$_6$ |
| | GAA/ GAA-[$^{13}$C$_2$]) |
| Extraction Type: | Protein Precipitation |
| Instrumentation/Detection: | UHPLC-MS/MS (API 5500, ESI+) |
| Run Time: | 5.50 minutes |
| Sample Preparation Temperature: | Wet Ice |
| Sample Storage Temperature: | −70° C. |
| Special Storage/Treatment Requirements: | QC samples are prepared in both acidified and non-acidified plasma treated with pegzilarginase (AEB1102), nor-NOHA (N-hydroxy-nor-L-arginine) inhibitor, and mannitol. |

Reference Materials and Matrix used are as follows:
GVA (EAG Laboratories)
ArgA (EAG Laboratories)
HArg (Tokyo Chemical Industry CO, Part No. H1172, Chemical Abstracts Service (CAS) No. 483-01-8)
NAArg (Sigma-Aldrich, Part No. A3133, CAS No. 155-84-0)
GAA (Sigma-Aldrich, Part No. G11608)
GVA-$^{13}$C$_6$ (EAG Laboratories)
ArgA-$^{13}$C$_6$ (EAG Laboratories)
HArg-d$_4$ (Santa Cruz Biotechnology, Part No. sc-280882, CAS No. 1332075-41-8)
NAArg-$^{13}$C$_6$ (Aeglea BioTherapeutics)
GAA-$^{13}$C$_2$ (Santa Cruz Biotechnology, Part No. sc-211572 S)
AEB1102 Co-ArgI-PEG drug substance (5.1 mg/mL) (pegzilarginase) (Aeglea BioTherapeutics)
K₂EDTA human plasma (Bioreclamation)
K₂EDTA human whole blood (Bioreclamation)

Commercial reagents used are as follows:

| ACN | acetonitrile, Omnisolv, EMD |
|---|---|
| C₃H₆O | acetone, Sigma-Aldrich |
| FA | formic acid, Omnisolv, EMD |
| GLA | glacial acetic acid, Acros Organics |
| 1N HCl | 1N hydrochloric acid, Fisher Scientific |
| IPA | isopropyl alcohol, Omnisolv, EMD |
| C₆H₁₄O₆ | mannitol, Sigma-Aldrich |
| MeOH | methanol, Omnisolv, EMD |
| MQ | Milli-Q purified water or deionized water |
| NH₄HCO₂ | Ammonium formate, Sigma-Aldrich |
| Nor-NOHA | Nor-NOHA, Cayman Chemical |
| PBS | phosphate buffered saline (1× solution), Fisher Scientific |
| PFHx | perfluorohexanoic acid |
| TCA | trichloroacetic acid |

Treated Human Plasma [THP]. Add 0.059 mL of AEB1102 to 20.0 mL of K2EDTA human plasma. Store in polypropylene vials (PPV) at approximately −70° C. The expiration is that of the plasma used.

Treated Human Lipemic Plasma [TLP]. Add 0.059 mL of pegzilarginase to 20.0 mL of K2EDTA lipemic human plasma. Store in PPV at approximately −70° C. The expiration is that of the plasma used.

Treated Human Whole Blood [THB]. Add 0.059 mL of pegzilarginase to 20.0 mL of K2EDTA human whole blood. Store in PPV at approximately 4° C. The expiration is that of the whole blood used.

1 mg/mL Nor-NOHA [NOHA]

Dissolve the entire contents of a 5 mg vial of nor-NOHA with 5.00 mL of MQ. Store in PPV at approximately −70° C. for up to 1 month.

10% Mannitol Solution (w/v) [MT1]

Weigh approximately 1.00 g of mannitol and dissolve with 10 mL MQ. Stir to dissolve. Store at room temperature for up to 1 month.

Non-Acidified Matrix [NM1]

Centrifuge 20 mL of K₂EDTA human plasma for 5 minutes at 3500 rcf. Add mL AEB1102 to the plasma using a pipette. Incubate the plasma at 37° C. for approximately 3 hours. Add 0.180 mL Nor-NOHA to the plasma vial. Add 0.200 mL of MT1 to the treated plasma in order to reach a 0.1% (v/v) of mannitol (this step can be performed just prior to use of plasma). Mix well. Store in PPV at approximately −70° C. for up to the expiration date of the plasma component.

Acidified Matrix [AM1]

Centrifuge 20 mL of K2EDTA human plasma for 5 minutes at 3500 rcf (relative centrifugal force). Add 0.059 mL AEB1102 to the plasma using a pipette. Incubate the plasma at 37° C. for approximately 3 hours. Add 0.400 mL GLA to the plasma vial. Add mL Nor-NOHA to the plasma vial. Add 0.200 mL of MT1 to the treated plasma in order to reach a 0.1% (v/v) of mannitol (this step can be performed just prior to use of plasma). Mix well. Store in PPV at approximately −70° C. for up to the expiration date of the plasma component.

10% (w/v) TCA [BAC-359]. Weigh out approximately 50 g TCA into a solvent bottle. Add 500 mL MQ using a graduated cylinder. Stir to dissolve. Solution can be stored at room temperature for up to 1 month. This solution is used as a protein precipitation solution. This solution is chilled on ice prior to use in sample extraction.

0.1% FA and 0.05% PFHx in MQ [BAC-360]. Measure 1000 mL of MQ using a graduated cylinder and add to a solvent storage bottle. Add 1 mL FA and 0.5 mL PFHx using a pipette. Mix thoroughly. Solution can be stored at room temperature for up to 1 month. This solution is used as mobile phase A (MPA). This solution must be made in a 1-L Teflon container.

0.1% FA and 0.05% PFHx in ACN [BAC-361]. Measure 1000 mL of ACN using a graduated cylinder and add to a solvent storage bottle. Add 1 mL FA and 0.5 mL PFHx using a pipette. Mix thoroughly. This solution can be stored at room temperature for up to 1 month. This solution is used as mobile phase B (MPB). This solution must be made in a 1-L Teflon container.

80:20:0.3 (v/v/v) MeOH:MQ:FA [BAC-409]

Combine 800 mL MeOH (methanol) and 200 mL MQ in a solvent storage bottle using graduated cylinders. Add 3.00 mL of FA using a pipette. Mix thoroughly. Store at room temperature for up to 1 month. This solution can be used as mobile phase A (MPA).

100 mM Ammonium Formate in MQ [BAC-409]

Measure 1000 mL of MQ using a graduated cylinder. Weigh approximately 6.306 g of ammonium formate into a tared weigh boat. Transfer the ammonium formate to a solvent storage bottle with rinses of the MQ. Transfer the remaining MQ to the bottle. Stir to dissolve. Store at room temperature for up to one month. This solution can be used to prepare mobile phase B (MPB).

70:30 (v/v) 100 mM Ammonium Formate:MeOH [BAC-410]

Combine 700 mL BAC-408 and 300 mL MeOH in a solvent storage bottle using graduated cylinders. Mix thoroughly. Store at room temperature for up to the expiration date of BAC-408. This solution can be used as mobile phase B (MPB).

1000:1 (v/v) MQ:FA [BAC-001].

Add 1000 mL MQ to a solvent bottle using a graduated cylinder. Add 1 mL FA using a pipette. Mix thoroughly. This solution can be stored at room temperature for up to 1 month. This solution can be used for R0 solution.

40:10:50:0.05 (v/v/v/v) IPA:Acetone:CAN:FA [BAC-083]

Combine 400 mL IPA, 100 mL acetone, and 500 mL ACN using a graduated cylinder and transfer to an appropriately-sized solvent storage bottle. Stir to mix. Using a pipette, transfer 0.500 mL FA to the bottle. Mix thoroughly. Store at room temperature for up to 1 month. Alternatively, a purchased solution can be used instead of a prepared solution. If a purchased solution is used, store the solution at room temperature according to standard procedures. This solution can be used for R3.

50:25:25 (v/v/v) IPA:ACN:MeOH [BAC-011]. Combine 500 mL IPA, 250 mL ACN, and 250 mL MeOH in a solvent bottle using graduated cylinders. Mix thoroughly. Solution can be stored at room temperature for up to 1 month. This solution is used as strong needle wash.

PREPARATION OF STOCK SOLUTIONS. Stock solutions are prepared in duplicate and compared prior to use. Quantities prepared may be altered provided proportionality and final concentration are maintained and documented.

GVA Stock Solution (10,000 μM) 15011. Weigh an amount of GVA (MW 173.17) equivalent to 3 mg after applying the correction factor to an amber glass vial. Dissolve with MQ and dilute to 10,000 μM. Mix thoroughly. Divide the solution into 0.075-mL aliquots and store the solution in PPV at approximately −70° C. Prior to use, stocks are thawed on wet ice.

ArgA Stock Solution (10,000 μM) [S02]. Weigh an amount of ArgA (MW 175.19) equivalent to 3 mg after applying the correction factor to an amber glass vial. Dissolve with MQ and dilute to 10,000 μM. Mix thoroughly. Sonicate the stock solution for approximately 10 minutes. Divide the solution into 0.075-mL aliquots and store the solution in PPV at approximately −70° C. Prior to use, stocks are thawed on wet ice.

HArg Stock Solution (40,000 μM) [S03]. Weigh an amount of HArg (MW 224.69) equivalent to 15 mg after applying the correction factor to an amber glass vial. Dissolve with MQ and dilute to 40,000 μM. Mix thoroughly. Divide the solution into 0.100-mL aliquots and store the solution in PPV at approximately −70° C. Prior to use, stocks are thawed on wet ice NAArg Stock Solution (20,000 μM) [S04]. Weigh an amount of NAArg (MW 216.24) equivalent to 6 mg after applying the correction factor to an amber glass vial. Dissolve with MQ and dilute to 20,000 μM. Mix thoroughly. Divide the solution into 0.075-mL aliquots and store the solution in PPV at approximately −70° C. Prior to use, stocks are thawed on wet ice.

GAA Stock Solution (40,000 μM) [S05]

Weigh an amount of GAA (MW 117.11) equivalent to 14 mg after applying the correction factor to an amber glass vial. Dissolve with [BAC-009] and dilute to 40,000 μM. Mix thoroughly. Divide the solution into 0.150-mL aliquots and store the solution protected from light (PFL) in PPV at approximately −70° C. Prior to use, stocks are thawed on wet ice.

PREPARATION OF Internal Standard (IS) SOLUTIONS. Quantities prepared may be altered provided proportionality and final concentration are maintained and documented.

GVA-$^{13}$C6 IS Stock Solution (4,150 μM) [I01]. Weigh an amount of GVA-$^{13}$C6 (MW 215.65) equivalent to 3 mg after applying the correction factor to an amber glass vial. Dissolve with MQ and dilute to 4150 μM. Mix thoroughly. Divide the solution into 0.050-mL aliquots and store the solution in PPV at approximately −70° C. Prior to use, stocks are thawed on wet ice.

ArgA-$^{13}$C6 IS Stock Solution (5,000 μM) [I02]. Weigh an amount of ArgA-$^{13}$C6 (MW 181.14) equivalent to 3 mg after applying the correction factor to an amber glass vial. Dissolve with MQ and dilute to 5,000 μM. Mix thoroughly. Divide the solution into aliquots and store the solution in PPV at approximately −70° C. Prior to use, stocks are thawed on wet ice.

HArg-d4 IS Stock Solution (5,000 μM) [I03]. Weigh an amount of HArg-d4 (MW 265.17) equivalent to 3 mg after applying the correction factor to an amber glass vial. Dissolve with MQ and dilute to 5000 μM. Mix thoroughly. Divide the solution into 0.050-mL aliquots and store the solution in PPV at approximately −70° C. Prior to use, stocks are thawed on wet ice.

NAArg-$^{13}$C6 IS Stock Solution (5,000 μM) [I04]. Weigh an amount of NAArg-$^{13}$C6 (MW 222.19) equivalent to 3 mg after applying the correction factor to an amber glass vial. Dissolve with MQ and dilute to 5,000 μM. Mix thoroughly. Divide the solution into aliquots and store the solution in PPV at approximately −70° C. Prior to use, stocks are thawed on wet ice.

GAA-13C2 IS Stock Solution (5,000 μM) [I05]

Weigh an amount of GAA-$^{13}$C$_2$ (MW 119.09) equivalent to 3 mg after applying the correction factor to an amber glass vial. Dissolve with [BAC-009] and dilute to 5,000 μM. Mix thoroughly. Divide the solution into 0.050-mL aliquots and store the solution PFL in PPV at approximately −70° C. Prior to use, stocks are thawed on wet ice.

Heavy IS Working Solution (2.075 μM I01; 2.50 μM I02, I04) [H106]

Combine 0.020 mL each of [I01], [I02] and [I04] with 39.940 mL [1 N HCl] in a PPV using a pipette. Mix thoroughly. Prepare the solution on wet ice. Discard solution after use.

IS Working Solution (5,000 nM) [I05]. Combine 0.020 mL each [I01], [I02], [I04], and [I05] and 39.920 mL [1 N HCl] in a PPV using a pipette. Mix thoroughly. Prepare the solution on wet ice. Discard the solution after use.

Preparation of Stock Comparison Solutions.

Prepare comparison solutions in PPV on wet ice using a pipette as shown in the table below. Mix thoroughly. Store refrigerated. Stock comparison solutions used to establish stability should be assessed within the established processed sample stability window. Quantities prepared may be altered provided proportionality and final concentration are maintained and documented.

| Solution ID | Source Solution ID | Source Solution Concentration (μM) | Source Solution Volume (mL) | Diluent Solution Used (mL) | Diluent Volume (mL) | Final Volume (mL) | Final Concentration (μM) |
|---|---|---|---|---|---|---|---|
| DS1 | I06 | *2.50 | 8.000 | BAC-359 | 32.000 | 40.000 | *0.500 |
| DS2 | HI06 | *2.50 | 4.000 | BAC-359 | 16.000 | 20.000 | *0.500 |
| DS3 | S01 | 10,000 | 0.010 | DS1 | 1.990 | 2.000 | 50.0 |
| SC1 | DS3 | 50.0 | 0.020 | DS1 | 1.980 | 2.000 | 0.500 |
| DS4 | S02 | 10,000 | 0.010 | DS1 | 1.990 | 2.000 | 50.0 |
| SC2 | DS4 | 50.0 | 0.020 | DS1 | 1.980 | 2.000 | 0.500 |
| DS5 | S04 | 20,000 | 0.010 | DS1 | 1.990 | 2.000 | 100 |
| SC4 | DS5 | 100 | 0.010 | DS1 | 1.990 | 2.000 | 0.500 |
| DS6 | S05 | 40,000 | 0.010 | DS1 | 1.990 | 2.000 | 200 |
| SC5 | DS6 | 200 | 0.010 | DS1 | 3.990 | 4.000 | 0.500 |
| DS7 | I05 | 5,000 | 0.020 | DS2 | 1.980 | 2.000 | 50.0 |
| SC6 | DS7 | 50.0 | 0.020 | DS2 | 1.980 | 2.000 | 0.500 |

SC6 may be referred to as SST for short-term stock comparisons or as SLT for long-term stock comparisons.
SC6 can be used to compare I05 stock solution preparations.
(*) when only one concentration is listed, GVA-$^{13}C_6$ concentrations are 0.83x the value shown.

Sample Extraction.

1. Transfer 0.050 mL of each calibration, quality control (QC), blank, and experimental sample into a 96-well plate on wet ice. Diluted samples must be diluted with 1×PBS with the appropriate dilution factor prior to sample processing.
2. Add 0.100 mL [1 N HCl] to each matrix blank sample.
3. Add 0.100 mL [I05] to each calibration, QC, blank with IS, and experimental sample. Do not add [I06] to GQC (GAA LLOQ (lower limit of quantification) (QC) samples, if present.
4. Vortex-mix 5 minutes at 1600 rpm.
5. Add 0.400 mL ice cold [BAC-359] to each sample.
6. Vortex-mix 5 minutes at 1000 rpm.
7. Centrifuge 5 minutes at 3500 rcf.
8. Transfer 0.300 mL of supernatant to a clean 96-well plate using TomTec or multichannel pipette.
9. Centrifuge 5 minutes at 3500 rcf.
10. Store processed samples at approximately 4° C. in the sample compartment of the LC instrument or in the refrigerator until analysis.

| Ultra High Performance Liquid Chromatography (UHPLC) Set up. | |
|---|---|
| UHPLC: | Shimadzu Nexera ® equipped with an autosampler |

44

-continued

| Ultra High Performance Liquid Chromatography (UHPLC) Set up. | |
|---|---|
| Column: | Imtakt Intrada Amino Acid 50 × 2 mm (PN: WAA22) |
| Column Temperature: | 40° C. |
| Run Time: | 5.50 minutes |
| Autosampler Temperature: | 4° C. |
| Recommended Injection Volume: | 2 to 8 μL |
| Mobile Phase: | A: 80:20:0.3 (v/v/v) MeOH:MQ:FA [BAC-409] |
| | B: 70:30 (v/v) 100 mM Ammonium Formate:MeOH [BAC-410] |
| R0 Rinse Solution: | 1000:1 (v/v) MQ:FA [BAC-001] |
| R3 Rinse Solution: | 40:10:50:0.05 (v/v/v/v) IPa: Acetone: ACN:FA [BAC-083] |

| Time (minutes) | Flow Rate (mL/minute) | Mobile Phase A (%) | Mobile Phase B (%) |
|---|---|---|---|
| Initial | 0.400 | 95 | 5 |
| 1.00 | 0.400 | 95 | 5 |
| 3.00 | 0.400 | 55 | 45 |
| 4.00 | 0.400 | 0 | 100 |
| 5.00 | 0.400 | 0 | 100 |
| 5.10 | 0.400 | 95 | 5 |
| 5.50 | 0.400 | 95 | 5 |

Mass Spectrometer Parameters. Parameters, except for Mass Spectrometer, Interface, and Scan Mode may be modified to obtain optimum performance. Exact mass transitions may vary slightly from instrument to instrument because of unit resolution of quadrupole mass spectrometers.

Mass Spectrometer: Applied Biosystems/MDS Sciex API 5500™

Interface: Turbo Spray, positive-ion mode

Scan Mode: Multiple reaction monitoring (MRM)

Curtain Gas (CUR): 25 psi

Gas Setting (GS1): 40 psi

Gas Setting (GS2): 40 psi

Ionization Voltage (IS): 5500 v

Temperature (TEM): 500° C.

Collision Gas Setting (CAD): medium or 8 psi

Entrance Potential (EP): 10 v

Exit Potential (CXP) 10 v

| Analyte | Parent Ion | Daughter Ion | Dwell Time (msec) | Collision Energy (CE) (v) | De-clustering Potential (DP) (v) |
|---|---|---|---|---|---|
| GVA | 174.0 | 96.0 | 50 | 30 | 45 |
| ArgA | 176.0 | 130.0 | 50 | 23 | 38 |
| HArg | 189.0 | 144.0 | 50 | 24 | 38 |
| NAArg | 217.0 | 70.0 | 50 | 44 | 50 |
| GAA | 118.1 | 75.8 | 50 | 25 | 100 |
| GVA-13C6 | 180.1 | 119.1 | 50 | 22 | 50 |
| ArgA-13C6 | 182.0 | 135.0 | 50 | 23 | 38 |
| HArg-d4 | 193.0 | 148.0 | 50 | 24 | 38 |
| NAARG-13C6 | 223.2 | 163.1 | 50 | 25 | 60 |
| GAA-13C2 | 120.1 | 78.0 | 50 | 25 | 100 |

Direct Binding ELISA for Detection of Antibodies Against PEG in Human Serum

A. Reagents/Buffers

Diluent Buffer/Assay Buffer (4% Bovine Gamma Globulin (BGG) in 1×PBS)

Assay diluent was prepared by adding 4 g of BGG to 100 mL of 1×PBS. The solution was filtered through a 0.22 NM filter and stored at 2-8° C. for up to 2 weeks. The volumes were scaled as needed.

Competition Buffer (Assay buffer+100 µg/mL PEG)

Competition buffer was prepared by adding 100 µg of PEG, per 1 milliliter of assay buffer. Competition buffer was made fresh on the day of the assay. The volumes were scaled as needed.

Stop Solution (1 M $H_3PO_4$)

21.4 mL of 85% (11.7 M) $H_3PO_4$ was added to 228.6 mL of dI (deionized) $H_2O$, mixed well and stored in the acid cabinet for up to 1 year. The volumes were scaled as needed.

Additional Reagents (See Tables Below)

| Reagent | Source | Cat Number | Batch/Lot Number |
|---|---|---|---|
| Mono-Pegylated BSA (MPEG 5 kDa) | Life Diagnostics | PBSA-02 | C-H0212A |
| Anti-PEG SPC (statistical process control) | Life Diagnostics | 9B5-6-25-7 | C-C1912A |
| SPC High Positive Control (mouse) (HPC-m 1000 ng/mL) | BioAgilytix | N/A | RP06Jun16kml01 |
| SPC Low Positive Control (LPC-m, 200 ng/ml) | BioAgilytix | N/A | RP06Jun16kml02 |
| Negative Control (NC, BRH1095944) | BioAgilytix | N/A | RP06Jun16kml03 |
| *High Positive Control (human) HPC-h BRH1182029 | An individual sample from Bioreclamation shown during development to have a high signal and to be highly inhibited by PEG | HMSRM | RP08Jul16JHJ01 (BRH1182029) |
| *Low Positive Control (human) LPC-h | 1:1 dilution of above in p-NHS | N/A | RP08Jul16JHJ02 |
| Pooled Normal Human Serum (p-NHS) | Bioreclamation | HMSRM | BRH1095944 |
| AEB1102 (aka, Co-Arg1 PEG) | Aeglea/KBI BioPharma | N/A | 15-0390 |
| Goat anti-Mouse IgG-Fc-HRP | Jackson Immunoresearch | 115-035-008 | 125494 |
| Rabbit anti-Human IgG/A/M-HRP | Jackson Immunoresearch | 309-035-064 | 120556 |

| Reagent | Source | Cat Number | Batch/Lot Number |
|---|---|---|---|
| Carbonate Coating Buffer | BioWorld | 40320016-1 | L16020109JC |
| Diluent Buffer/Assay Buffer (4% BGG in 1X PBS) | BioAgilytix | N/A | RP08Jul16JHJ04, RP13Jul16MB01, RP11Jul16JHJ02, RP18Jul16JHJ01 |
| Bovine Gamma Globulin | Millipore | 82-041 | 1269 |
| Wash Buffer (1X PBS) | BioAgilytix | N/A | RP11Jul16JHJ01, RP12Jul16MBM01, RP 13Jul16JHJ01, RP18Jul 16JHJ02, RP08Jul 16JHJ03 |

-continued

| Reagent | Source | Cat Number | Batch/Lot Number |
|---|---|---|---|
| Polypropylene Plates | Costar | 3365 | 09516000 |
| Nunc Immuno Starwell C8 Maxisorp Plates | Thermo | 441653 | 125663 |
| TMB Microwell Proxidase kit | KPL | 50-76-00 | 10158819 |
| Stop Solution (1M H$_3$PO$_4$) | BioAgilytix | N/A | RP08Jul16MBM01, RP26May16kml03, RP18Jul16MBM01 |
| Human IgG | Jackson Immunoresearch | 009-000-003 | 126258 |
| Human IgM | Jackson Immunoresearch | 009-000-012 | 124517 |

B. Screening Assay Procedure

Wells of a Starwell C8 Maxisorp (a 96-well format plate) were coated with 100 μL of 2 μg/mL BSA mPEG 5K (5,000 Daltons), or 500 ng/mL human IgG, or 500 ng/mL Human IgM in carbonate coating buffer (these controls were excluded from post-cut point runs) according to a plate map. The plate(s) were sealed, shaken briefly at ~450 rpm to ensure distribution across the wells, and incubated for approximately 1 hr at 37° C. After the incubation, wells were washed 3 times with 1×PBS. The washer program contained an overflow with aspiration setting, and a 10 second shake after each dispense (Program 29_Wash_Shake) to ensure complete washing of the star-well plates. This program was used for all of the wash steps in this procedure.

After washing, the plate(s) were inverted and tapped dry on absorbent paper. Then 300 μL of Diluent Buffer was added to all wells of the plate(s). The Diluent Buffer contains 4% BGG so also considered the "Blocking Buffer." The plate(s) were covered and incubated for a minimum of 1 hour, but no more than 3 hrs, at room temperature with shaking (~450 rpm).

After the blocking incubation period, the plate(s) were washed, inverted and tapped dry on absorbent paper. Controls and samples diluted to the minimum required dilution (MRD) of 50-fold in Diluent Buffer were added to the plate in duplicate (100 μL/well) according to the plate map. The plate(s) were then sealed and incubated for approximately 1 hour at room temperature with shaking (~450 rpm).

The plate(s) were washed, inverted and tapped dry on absorbent paper, and 100 μL of detection antibodies were added to the appropriate wells following the plate map. The mouse anti-PEG antibody was detected using goat anti-Mouse IgG-Fc-HRP that was diluted 1:5,000, and anti-human antibodies were detected using rabbit anti-human IgG/A/M that was diluted 1:30,000 in diluent buffer and added to the appropriate wells. The plate(s) were sealed and incubated at room temperature for approximately 1 hour with shaking (~450 rpm). The plate(s) were washed, inverted and tapped dry on absorbent paper, followed by addition of 100 μL per well of TMB substrate. The plate(s) were covered and incubated for approximately 10-20 minutes at room temperature with shaking (~450 rpm). The reaction was stopped by adding 100 μL of stop solution per well. The plate(s) were shaken briefly to ensure C. Confirmatory Assay Procedure According to the plate map below, wells of a Starwell C8 Maxisorp plate were coated with 100 μL of 2 μg/mL BSA-mPEG 5K, or 500 ng/mL human IgG, or 500 ng/mL human IgM in carbonate coating buffer (these controls were excluded from post-cut point runs). The plate(s) were sealed, shaken briefly at ~450 rpm to ensure distribution across the wells, and incubated for approximately 1 hr at 37° C.

After the incubation, wells were washed 3 times with (1×PBS) using Program 29_Wash_Shake, to ensure complete washing of the Starwell plates. This program was used for all of the wash steps in this procedure. After washing, the plate(s) were inverted and tapped dry on absorbent paper. Then 300 μL of Diluent Buffer was added to all wells of the plate(s) as a blocking step. The plate(s) were covered and incubated for a minimum of 1 hour, but no more than 3 hrs, at room temperature with shaking (~450 rpm).

While the Starwell plate(s) were being blocked, samples and controls were diluted to the MRD of 50-fold in Diluent Buffer and in Competition Buffer containing PEG at 100 μg/mL in a polypropylene plate. The diluted samples and controls were incubated at room temperature for approximately 1 hour with shaking (~450 rpm).

After the blocking incubation period, the star-well plate(s) were washed, inverted, and tapped dry on absorbent paper. Controls and samples pre-incubated with and without PEG, were added to the plate in duplicate (100 μL/well) according to the plate map. The plate(s) were then sealed and incubated for approximately 1 hour at room temperature with shaking (~450 rpm).

After washing, the plate(s) were inverted and tapped dry on absorbent paper and 100 μL of detection antibodies were added to the appropriate wells following the plate map. The mouse anti-PEG antibody was detected using (goat anti-Mouse IgG-Fc-HRP) that was diluted 1:5,000, and the anti-human antibodies were detected using (rabbit anti-human IgG/A/M that was) diluted 1:30,000 in diluent buffer and added to the appropriate wells. The plate(s) were sealed and incubated at room temperature for approximately 1 hour with shaking (~450 rpm). The plate(s) were washed, inverted and tapped dry on absorbent paper, followed by addition of 100 μL per well of TMB substrate. The plate(s) were covered and incubated for approximately 10-20 minutes at room temperature with shaking (~450 rpm). The reaction was stopped by adding 100 μL of stop solution per well. The plate(s) were shaken briefly to ensure proper mixing and then read on a Synergy 2 plate reader at 450 (detection) 620 (background).

D. Titer Method Procedure

The titer assay followed the same procedure as the screening assay. Samples to be titered were subjected to a minimum of seven 2-fold serial dilutions in a negative pooled human serum. Normal human pools were screened during qualification and the one with the lowest background was selected for use as the negative pool in the validation. These titer dilutions were diluted to the minimum required dilution of 50-fold using diluent buffer and added to the plate in duplicate (100 μL/well) according to the plate map.

E. Method Validation

Validation of the method included assessment of specificity, assay sensitivity, selectivity/matrix interference, drug tolerance, prozone (hook) effect, titration assay linearity, intra- and inter-assay precision, short-term and freeze and thaw stability, and establishment of screening, confirmatory, and titration cut points.

Two sets of controls were used for assay validation. One set was prepared using the mouse anti-PEG surrogate positive control spiked into pooled normal human serum (NC) to yield a high (HPC-m) and low (LPC-m) signal in the assay. The second set was prepared using a human sample with high anti-PEG responses in screening assay and high inhibition in the confirmatory assay. This sample would be consistent with an expected pre-existing anti-PEG sample. The human anti-PEG low control was prepared by diluting the identified high human sample into negative control serum to generate samples that result in a low (LPC-h) signal in the assay. The undiluted high human sample was used as HPC-h. Both sets of controls were included in each run where applicable. Controls should show signal proportional to their levels, i.e., high is greater than low, and low is greater than the cut point. Immunoglobulin controls (human IgG and human IgM coated on the plate) were also included in the cut point runs to verify the performance of the detection antibody cocktail.

F. Cut Point Analysis

Mouse Anti-PEG Screening Cut Point. For evaluation of data using the mouse anti-PEG SPC, a screening cut point was set using 2× the Standard deviation of the mean of all the negative control samples generated during validation (n=55 plates). This calculation resulted in a correction factor of 0.01467 which was added to the mean of the NC on each plate to generate a cut point specific for the mouse anti-PEG SPC samples.

Human Screening Assay Cut Point. The screening assay cut point was established using 98 individual Normal human serum samples. Six determinations were made for each sample by 3 analysts over a minimum of 7 runs. The data was evaluated using SAS JMP® software (version 12 or later), statistical outliers were eliminated, variance was determined and a cut point was established. For the determinations of statistical outliers, responses were normalized by dividing the mean signal for the sample by the mean of the anti-human NC samples for each plate.

G. Cut Point Determinations

Human Anti-PEG Screening Cut Point. Parametric and nonparametric screening floating cut point factors were determined using the normalized values. First, a parametric method with Tukey's biweight procedure was used to calculate robust estimates of the mean and standard deviation (SD) of the ratios following exclusion of outliers. The parametric floating cut point factor at the 5% false positive error rate was then determined by multiplying the SD value by the 95th quantile of the t-distribution (with degrees of freedom equal to the number of ratio values minus 1) and adding the product to the mean value. The nonparametric 5% error rate cut point factor was determined by calculation of the empirical percentile for the ratio values.

Human Confirmatory Cut Point. Confirmatory cut point values were established by the procedure recommended by Shankar G, et al at the 1% false positive error rates. The cut point values were determined by assigning a lower limit of specific inhibition using 14 samples excluded from the screen cut point assignment as biological outliers. These samples consistently had the higher % inhibition values, than samples that would be screened as negative. The percentage of the change from the unspiked samples was calculated for each sample using the following equation:

$$\% \text{Inhibition} = \left(1 - \frac{\text{Signal of Sample with } PEG}{\text{Signal of Sample Alone}}\right) \times 100$$

Parametric confirmatory cut point was determined by first calculating Tukey's biweight estimates of the mean and SD of all % inhibition values retained in the analysis. The cut point values were then computed by multiplying the SD value by a factor equal to the 1st quantiles of the t-distribution, respectively (with degrees of freedom equal to the number of inhibition values minus 1) and subtracting the product to the mean value. Nonparametric cut point values were also determined based on the empirical 1st percentile.

G. Specificity

The addition of high levels of human IgG did no impact the signal generated in the assay compared to an unspiked sample.

H. PEG Tolerance

Assay interference was assessed by performing 2-fold serial dilutions of PEG, starting with a concentration of 100 μg/mL, in presence of concentrations of anti-PEG surrogate positive control equivalent to HPC-m and LPC-m, and of the human anti-PEG HPC-h and LPC-h. A zero spike control consisting of each control without PEG was also run. This was performed in duplicate over a minimum of 2 runs by a minimum of 2 analysts. The human specific screening cut point was used to determine the tolerance in these assay runs. The HPC-m, HPC-h, and LPC-h were tolerant to all concentrations of PEG tested up to 100 μg/mL.

I. Drug Tolerance of Pegzilarginase

Assay interference was assessed by performing 2-fold serial dilutions of pegzilarginase, starting with a concentration of 150 μg/mL, in presence of concentrations of anti-PEG surrogate positive control equivalent to HPC-m and LPC-m, and of the human anti-PEG HPC-h and LPC-h. A zero spike control consisting of each control without PEG was also run. The evaluation of drug tolerance was performed using the anti-human specific cut point. In one run the HPC-m was tolerant to 9.38 μg/mL and in the second run up to 37.5 μg/mL for a mean drug tolerance of 23.4 μg/mL. In one run the LPC-m was not tolerant to Co-Arg1 PEG and in the second run was tolerant to 2.34 μg/mL. In one run the HPC-h was tolerant to 9.38 μg/mL and in the second run up to 18.8 μg/mL for a mean drug tolerance of 14.1 μg/mL. In one run the LPC-h was tolerant to 4.69 μg/mL and in the second run to 9.38 μg/mL for a mean drug tolerance of 7.04 μg/mL.

Neuromotor and Neurocognitive Testing Methods

A physical exam is completed with assessments of neurological and neuromotor function including, but not limited to, 6MWT, GMFM, Berg Balance Scale, the Modified Ashworth Scale, and the Purdue Pegboard Test. Assessments may be conducted over more than one day. The assessments may be recorded at baseline and at subsequent time points thereafter.

The 6MWT has been widely used in clinical studies to globally assess the cardiovascular, pulmonary, and neuromuscular systems in numerous disease conditions. It measure the distance a patient can walk on a flat surface in 6 minutes. The American Thoracic Society (ATS) published a standardized methodology (see, ATS Statement Guidelines for the Six-Minute Walk; *Am. J. Respir. Crit. Care Med.,* 166: 111-117, 2002) for performing the test, which is well-tolerated and simple to administer. This procedure was followed for the 6MWT. Modifications of the methodology may be allowed to account for the disease state of the patient as well as logistic considerations of the testing location, with approval from the sponsor. Non-ambulatory patients did not have the 6MWT administered. Results of the 6MWT are recorded as distance completed in meters and percent change from baseline.

Berg Balance Scale measures balance in patients with impairment of balance function by assessing performance in certain functional tasks. There are 14 tasks that evaluate certain aspects of balance, such as sitting to standing, transfers, turning, and standing on one foot. Additionally, most tasks require the subject to maintain the position for a specific time.

GMFM is a clinical measure designed to evaluate changes in gross motor function looking at a range of activities such as lying, rolling, walking, running, and jumping. A 4-point scoring system is used for each item of the GMFM to determine the degree to which a person can initiate and complete a movement, covering five dimensions (A through E): A: lying and rolling, B: sitting, C: crawling and kneeling, D: standing, and E: walking, running, and jumping.

The Modified Ashworth Scale was developed to assess the spasticity of patients with central nervous system (CNS) lesions and is used to measure the resistance to passive movement about a joint due to spasticity. The scale is well tolerated and easy to perform. The scale cannot differentiate between spasticity and soft tissue stiffness. The scale utilizes a scoring scale of 0 (no spasticity) to 4 (total rigidity) with 6 scoring choices as indicated the table below:

| Score | Modified Ashworth |
|---|---|
| 0 | No increase in tone |
| 1 | Slight increase in tone manifested by a catch and release or by minimal resistance at the end of the range of motion (ROM) when moved in flexion or extension |
| 1+ | Slight increase in tone manifested by a catch, followed by a minimal resistance throughout the remainder (less than half) of the ROM |
| 2 | More marked increase in tone through most of the ROM, but affected parts easily moved |
| 3 | Considerable increase in tone; passive movement difficult |
| 4 | Limb rigid in flexion or extension |

The Purdue Pegboard Test is a test of manipulative dexterity and bimanual coordination measuring performance speed in a fine motor task utilizing both sides of the body (Tiffin et al., 1948). The test involves two different abilities: (1) gross movements of arms, hands, and fingers, and (2) fine motor extremity, also called "fingerprint" dexterity. Poor pegboard performance is a sign of deficits in complex, visually-guided or coordinated movements that are likely mediated by circuits involving the basal ganglia.

The table below shows additional neurocognitive, developmental, and quality of life (QOL) assessments that can be performed on patients undergoing treatment to assess improvement over time.

| Domain Assessed | Test Name | Description | Age Range | Approximate Time Required |
|---|---|---|---|---|
| Intelligence | Wechsler Adult Intelligence IV | Verbal and Performance intelligent quotients (IQs) are yielded and Full Scale IQ can be measured. Processing speed and memory are also measured. Shortened version of Full Scale IQ without processing speed and working memory called the General Ability Index (GAI) may be used. | 16 years and older | 30 to 40 minutes |
| | Wechsler Adult Intelligence V | Verbal and Performance IQs are yielded and Full Scale IQ can be measured. Processing speed and memory are also measured. Shortened version of Full Scale IQ without processing speed and working memory (the GAI) may be used. | 6 to 16 years | 45 to 65 minutes |
| | Wechsler Preschool and Primary Scale of Intelligence IV | Verbal and Performance IQs are yielded as well as Full Scale IQ. Processing speed and memory are also measured. Shortened version of Full Scale IQ without processing speed and working memory (the GAI) may be used. | 3 to 6 years | 30 to 40 minutes |
| | Bayley Scales of Infant Development III | Developmental test of cognitive ability for ages 2 to 3.5 years. Cognitive Scale and Mental Developmental Index will be included as an endpoint. | 2 to 3.5 years | 40 minutes |

-continued

| Domain Assessed | Test Name | Description | Age Range | Approximate Time Required |
|---|---|---|---|---|
| | | Mental Development Index is the score. Motor component will be included. Language scales should also be given, but will be exploratory only. This will be the only direct measurement in children younger than 4 years of age | | |
| Memory | Rey Auditory Verbal Learning Test (RAVLT) | A list of 15 unrelated words is read aloud. The number of words recalled after each of 3 trials and a 30-minute delay is recorded. | 6 years and older | 40 to 45 minutes |
| | Atlantis Subtest on Kauffman Assessment Battery for Children (KABC) II | A set of pictures are paired with nonsense words; child must recognize picture paired with word on both learning and delayed response trials. | 3 to 8 years | 20 minutes |
| Attention | Test of Variables of Attention (TOVA) version 9 | Test requires the child/adult to respond with a button or key on a keyboard to a designated stimulus that is flashed on the screen and not to respond to other stimuli. The speed, accuracy, and consistency are measured. | 6 years to adult | 22 minutes |
| Development | Gender- and age-specific growth charts from the CDC | Stature-for-age and weight-for-age charts will be collected, and weight-for-stature will additionally be collected for patients 2 to 5 years old. Age-appropriate head circumference measures will be collected. | ≥2 to <18 years | varies |
| | | Patient or Parent Reported Outcomes | | |
| Adaptive Behavior | Vineland Adaptive Behavior Scales II | Parent observational measure by interview format will be used. Includes composite score, communication, daily living skills, socialization, and motor skills. | All ages | 30 to 60 minutes |
| Quality of Life | PROMIS Parent Proxy Profile v2.0; PROMIS Pediatric Profile v2.0; PROMIS-29 v2.0[a] | Adult and child self-rating of QOL; parent proxy rating of QOL | | 15 minutes |
| | PedsQL Measurement Model for the Pediatric Quality of Life Inventory[a] | Rating of QOL | 2 to 18 years | 5 to 10 minutes |
| | 36-Item Short Form Health Survey (SF-36) | Eight scaled scores: vitality, physical functioning, bodily pain, general health perceptions, physical functioning, emotional functioning, social functioning, and mental health. Higher scores indicate better health. | 18 years or greater | 10 minutes |

| Domain Assessed | Test Name | Description | Age Range | Approximate Time Required |
|---|---|---|---|---|
| | Short Form Zarit Burden Interview (ZBI-12) | Parent/caregiver self-rating of QOL. | All ages | 30 minutes |

<sup>a</sup>PROMIS (for patients that began the phase 1/2 study utilizing the PROMIS assessment) or PedsQL Measurement Model for the Pediatric Quality of Life Inventory (for patients that did not being the phase 1/2 study utilizing the PROMIS assessment).

REFERENCES LIST

ATS Statement Guidelines for the Six-Minute Walk, *Am. J. Respir. Crit. Care Med.,* 166: 111-117, 2002

Burrage et al., "Human recombinant arginase enzyme reduces plasma arginine in mouse models of arginase deficiency," *Hum. Mol. Genetics* 24(22): 6417-27 (2015)

Carvalho, D. R., et al., "Clinical features and neurologic progression of hyperargininemia," *Pediatr. Neurol.,* 46(6): 369-74 (2012)

Cheng et al., *Cancer Res.* 67: 309-17, 2007

Deignan et al., "Increased plasma and tissue guanidine compounds in a mouse model of hyperargininemia,"*Mol. Genet. Metab.* 93: 172-178, 2008

Dillon et al., "Biochemical characterization of the arginine degrading enzymes arginase and arginine deiminase and their effect on nitric oxide production,"*Med. Sci. Monit.,* 8(7): BR248-253 (2002)

Downs et al., "The Berg Balance Scale," *J. Physiother.,"* 2015 61(1):46

Enright et al., "Reference equations for the six-minute walk in healthy adults," *Am. J. Respir. Crit. Care Med.,* 1998 158(5 Pt 1): 1384-1387

Geiger et al., "Six-minute walk test in children and adolescents," *J. Pediatr.,* 2007, 150(4): 395-399

Häberle et al., "Suggested guidelines for the diagnosis and management of urea cycle disorders," *Orphanet. J. Rare Dis.,* 2012 7: 32

Harris et al., *Clin. Pharmacokinet.* 40(7): 539-51, 2001

Lambert et al., "Hyperargininemia: intellectual and motor improvement related to changes in biochemical data," *J. Pediatr.,* 1991, 118(3): 420-4

Lopez et al., *FEBS J.* 272: 4540-48, 2005

Lüneburg, N. et al., "Reference intervals for plasma L-arginine and the L-arginine: asymmetric dimethylarginine ratio in the Framingham Offspring Cohort." *J. Nutr.* 141(12): 2186-2190 (2011).

Marescau et al. "Guanidino compound analysis as a complementary diagnostic parameter for hyperargininemia: Follow-up of guanidino compound levels during therapy," *Pediatric. Res.* 27(3): 297-303 (1990)

Marescau et al., "The pathobiochemistry of uremia and hyperargininemia further demonstrates a metabolic relationship between urea and guanidinosuccinic acid," 1992 41(9): 1021-1024

Oeffinger et al., "Outcome tools used for ambulatory children with cerebral palsy: responsiveness and minimum clinically important differences," *Dev. Med. Chile Neurol.,* 2008; 50(12): 918-925

Prasad et al., "Argininemia: a treatable genetic cause of progressive spastic diplegia simulating cerebral palsy—case reports and literature review" *J. Child Neurol.* 12: 301-309, 1997

Remington, *The Science and Practice of Pharmacy,* 19th ed., Gennaro, ed., Mack Publishing Co., Easton, PA 1995

Savoca et al., *Cancer Biochem. Biophys.* 7: 261-268, 1984

Schrover et al., "Minimal clinically important difference for the 6-min walk test: literature review and application to Morquio A syndrome," *Orphanet. J. Rare Dis.,* 2017 12(1):78

Schlune et al., "Hyperargininemia due to arginase 1 deficiency: the original patients and their natural history, and a review of the literature," *Amino Acids* 47: 1751-1762, 2015

Segawa et al., "A long-term survival case of arginase deficiency with severe multicystic white matter and compound mutations," *Brain Dev.* 33: 45-48, 2011

Stockler-Ipsiroglu et al., "Guanidinoacetate methyltransferase (GAMT) deficiency: outcomes in 48 individuals and recommendations for diagnosis, treatment and monitoring," *Mol. Genet. Metab.,* 111(1): 16-25, 2014

Uchino, T., et al., "Molecular basis of phenotypic variation in patients with argininemia," *Hum. Genet.* 96(3): 255-60 (1995)

Wu, G. et al., "Arginine metabolism: nitric oxide and beyond," *Biochem. J.,* 336 (Pt 1), 1-17, 1998

Wyse et al., "In vitro stimulation of oxidative stress in cerebral cortex of rats by the guanidino compounds accumulating in hyperargininemia," *Brain Res.* 2001, 923(1-2): 50-7 And U.S. Patent Publications: U.S. Pub. 20170240922; U.S. Pub. 20170283830; U.S. Pub. 20170224843; U.S. Pub. 20170191078; U.S. Pub. 20160095884; U.S. Pat. Nos. 8,398,968; 8,440,184; U.S. Pub. 20160095884; and U.S. Pub. 20140154797.

What is claimed is:

1. A method for reducing a plasma level of at least one compound selected from the group consisting of: arginine, N-α-acetylarginine (NAArg), argininic acid (ArgA), α-keto-δ-guanidinovaleric acid (GVA), guanidinoacetic acid (GAA), to a normal level in a subject with Arginase 1 (ARG1) deficiency (ARG1-D) comprising administering to the subject a composition comprising a therapeutically effective amount of a pegylated arginase, wherein the pegylated arginase is administered intravenously initially at a dosage of about 0.1 mg/kg, and weekly thereafter either subcutaneously or intravenously at a dosage of about 0.01 mg/kg to about 1.00 mg/kg.

2. The method of claim 1, wherein the pegylated arginase is administered intravenously initially at a dosage of about 0.1 mg/kg, and weekly thereafter either subcutaneously or intravenously at a dosage of about 0.01 mg/kg to about 0.50 mg/kg.

3. The method of claim 2, wherein the pegylated arginase is administered intravenously initially at a dosage of about 0.1 mg/kg, and weekly thereafter either subcutaneously or intravenously at a dosage of about 0.01 mg/kg to about 0.25 mg/kg.

4. The method of any one of claims 1-3, wherein the pegylated arginase is pegzilarginase.

5. The method of claim 1, wherein a plasma level of at least one compound selected from the group consisting of: ArgA, NAArg, GVA, GAA, and arginine, is reduced to a normal level in the subject in less than 3 days after initial administration of the pegylated arginase.

6. The method of claim 1, wherein a plasma level of at least one compound selected from the group consisting of: ArgA, NAArg, GVA, GAA, and arginine, is reduced to a normal level in the subject in less than 2 days after initial administration of the pegylated arginase.

7. The method of claim 1, wherein a plasma level of at least one compound selected from the group consisting of: ArgA, NAArg, GVA, GAA, and arginine, is reduced to a normal level in the subject in less than 1 day after initial administration of the pegylated arginase.

8. The method of claim 1, wherein the dosage of the pegylated arginase administered to the subject is sufficient to reduce by at least 2 fold a plasma level of at least one compound selected from the group consisting of: ArgA, NAArg, GVA, GAA, and arginine, wherein the plasma level is assayed about 24 to 48 hours after administration of the pegylated arginase.

9. A method for reducing a plasma level of at least one compound selected from the group consisting of: arginine, N-α-acetylarginine (NAArg), argininic acid (ArgA), α-keto-δ-guanidinovaleric acid (GVA), guanidinoacetic acid (GAA), to a normal level in a subject with Arginase 1 (ARG1) deficiency (ARG1-D) comprising administering to the subject a composition comprising a therapeutically effective amount of a pegylated arginase, wherein the pegylated arginase is administered subcutaneously initially at a dosage of about 0.1 mg/kg, and weekly thereafter either subcutaneously or intravenously at a dosage of about 0.01 mg/kg to about 1.00 mg/kg.

10. The method of claim 9, wherein the pegylated arginase is administered subcutaneously initially at a dosage of about 0.1 mg/kg, and weekly thereafter either subcutaneously or intravenously at a dosage of about 0.01 mg/kg to about 0.50 mg/kg.

11. The method of claim 10, wherein the pegylated arginase is administered subcutaneously initially at a dosage of about 0.1 mg/kg, and weekly thereafter either subcutaneously or intravenously at a dosage of about 0.01 mg/kg to about 0.25 mg/kg.

12. The method of any one of claims 9-11, wherein the pegylated arginase is pegzilarginase.

13. The method of claim 9, wherein a plasma level of at least one compound selected from the group consisting of: ArgA, NAArg, GVA, GAA, and arginine, is reduced to a normal level in the subject in less than 3 days after initial administration of the pegylated arginase.

14. The method of claim 9, wherein a plasma level of at least one compound selected from the group consisting of: ArgA, NAArg, GVA, GAA, and arginine, is reduced to a normal level in the subject in less than 2 days after initial administration of the pegylated arginase.

15. The method of claim 9, wherein a plasma level of at least one compound selected from the group consisting of: ArgA, NAArg, GVA, GAA, and arginine, is reduced to a normal level in the subject in less than 1 day after initial administration of the pegylated arginase.

16. The method of claim 9, wherein the dosage of the pegylated arginase administered to the subject is sufficient to reduce by at least 2 fold a plasma level of at least one compound selected from the group consisting of: ArgA, NAArg, GVA, GAA, and arginine, wherein the plasma level is assayed about 24 to 48 hours after administration of the pegylated arginase.

17. The method of claim 1, wherein the subject has a minimal clinically important difference (MCID) of greater than 1 after 9 days of treatment.

18. The method of claim 17, wherein the plasma level of arginine is correlated with the MCID.

19. The method of claim 1, wherein the pegylated arginase has the sequence of SEQ ID NO: 13.

20. The method of claim 19, wherein the pegylated arginase lacks the N-terminal methionine.

21. The method of claim 9, wherein the pegylated arginase has the sequence of SEQ ID NO: 13.

22. The method of claim 21, wherein the pegylated arginase lacks the N-terminal methionine.

* * * * *

SEQUENCE LISTING

```
Sequence total quantity: 14
SEQ ID NO: 1            moltype = AA  length = 354
FEATURE                 Location/Qualifiers
source                  1..354
                        mol_type = protein
                        organism = Homo sapiens
SEQUENCE: 1
MSLRGSLSRL LQTRVHSILK KSVHSVAVIG APFSQGQKRK GVEHGPAAIR EAGLMKRLSS  60
LGCHLKDFGD LSFTPVPKDD LYNNLIVNPR SVGLANQELA EVVSRAVSDG YSCVTLGGDH  120
```

-continued
***

```
SLAIGTISGH ARHCPDLCVV WVDAHADINT PLTTSSGNLH GQPVSFLLRE LQDKVPQLPG  180
FSWIKPCISS ASIVYIGLRD VDPPEHFILK NYDIQYFSMR DIDRLGIQKV MERTFDLLIG  240
KRQRPIHLSF DIDAFDPTLA PATGTPVVGG LTYREGMYIA EEIHNTGLLS ALDLVEVNPQ  300
LATSEEEAKT TANLAVDVIA SSFGQTREGG HIVYDQLPTP SSPDESENQA RVRI        354

SEQ ID NO: 2              moltype = AA  length = 322
FEATURE                   Location/Qualifiers
source                    1..322
                          mol_type = protein
                          organism = Homo sapiens
SEQUENCE: 2
MSAKSRTIGI IGAPFSKGQP RGGVEEGPTV LRKAGLLEKL KEQECDVKDY GDLPFADIPN  60
DSPFQIVKNP RSVGKASEQL AGKVAEVKKN GRISLVLGGD HSLAIGSISG HARVHPDLGV  120
IWVDAHTDIN TPLTTTSGNL HGQPVSFLLK ELKGKIPDVP GFSWVTPCIS AKDIVYIGLR  180
DVDPGEHYIL KTLGIKYFSM TEVDRLGIGK VMEETLSYLL GRKKRPIHLS FDVDGLDPSF  240
TPATGTPVVG GLTYREGLYI TEEIYKTGLL SGLDIMEVNP SLGKTPEEVT RTVNTAVAIT  300
LACFGLAREG NHKPIDYLNP PK                                          322

SEQ ID NO: 3              moltype =   length =
SEQUENCE: 3
000

SEQ ID NO: 4              moltype =   length =
SEQUENCE: 4
000

SEQ ID NO: 5              moltype =   length =
SEQUENCE: 5
000

SEQ ID NO: 6              moltype =   length =
SEQUENCE: 6
000

SEQ ID NO: 7              moltype =   length =
SEQUENCE: 7
000

SEQ ID NO: 8              moltype =   length =
SEQUENCE: 8
000

SEQ ID NO: 9              moltype =   length =
SEQUENCE: 9
000

SEQ ID NO: 10             moltype =   length =
SEQUENCE: 10
000

SEQ ID NO: 11             moltype =   length =
SEQUENCE: 11
000

SEQ ID NO: 12             moltype =   length =
SEQUENCE: 12
000

SEQ ID NO: 13             moltype = AA  length = 322
FEATURE                   Location/Qualifiers
VARIANT                   1
                          note = M or may be absent
source                    1..322
                          mol_type = protein
                          organism = Homo sapiens
SEQUENCE: 13
XSAKSRTIGI IGAPFSKGQP RGGVEEGPTV LRKAGLLEKL KEQECDVKDY GDLPFADIPN  60
DSPFQIVKNP RSVGKASEQL AGKVAEVKKN GRISLVLGGD HSLAIGSISG HARVHPDLGV  120
IWVDAHTDIN TPLTTTSGNL HGQPVSFLLK ELKGKIPDVP GFSWVTPCIS AKDIVYIGLR  180
DVDPGEHYIL KTLGIKYFSM TEVDRLGIGK VMEETLSYLL GRKKRPIHLS FDVDGLDPSF  240
TPATGTPVVG GLTYREGLYI TEEIYKTGLL SGLDIMEVNP SLGKTPEEVT RTVNTAVAIT  300
LACFGLAREG NHKPIDYLNP PK                                          322

SEQ ID NO: 14             moltype = AA  length = 333
FEATURE                   Location/Qualifiers
source                    1..333
                          mol_type = protein
                          organism = Homo sapiens
SEQUENCE: 14
```

-continued

```
SVHSVAVIGA PFSQGQKRKG VEHGPAAIRE AGLMKRLSSL GCHLKDFGDL SFTPVPKDDL    60
YNNLIVNPRS VGLANQELAE VVSRAVSDGY SCVTLGGDHS LAIGTISGHA RHCPDLCVVW   120
VDAHADINTP LTTSSGNLHG QPVSFLLREL QDKVPQLPGF SWIKPCISSA SIVYIGLRDV   180
DPPEHFILKN YDIQYFSMRD IDRLGIQKVM ERTFDLLIGK RQRPIHLSFD IDAFDPTLAP   240
ATGTPVVGGL TYREGMYIAE EIHNTGLLSA LDLVEVNPQL ATSEEEAKTT ANLAVDVIAS   300
SFGQTREGGH IVYDQLPTPS SPDESENQAR VRI                               333
```